United States Patent
Manabe et al.

(10) Patent No.: US 9,938,462 B2
(45) Date of Patent: *Apr. 10, 2018

(54) LIQUID-CRYSTALLINE MEDIA, COMPONENTS FOR HIGH-FREQUENCY TECHNOLOGY, AND MESOGENIC COMPOUNDS

(71) Applicant: MERCK PATENT GMBH, Darmstadt (DE)

(72) Inventors: Atsutaka Manabe, Bensheim (DE); Dagmar Klass, Darmstadt (DE); Renate Seeger, Riedstadt (DE); Michael Wittek, Erzhausen (DE); Matthias Bremer, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/654,629

(22) PCT Filed: Dec. 2, 2013

(86) PCT No.: PCT/EP2013/003628
§ 371 (c)(1),
(2) Date: Jun. 22, 2015

(87) PCT Pub. No.: WO2014/094973
PCT Pub. Date: Jun. 26, 2014

(65) Prior Publication Data
US 2015/0322344 A1 Nov. 12, 2015

(30) Foreign Application Priority Data
Dec. 21, 2012 (EP) .................... 12008528

(51) Int. Cl.
| | | |
|---|---|---|
| G02F 1/1333 | (2006.01) | |
| C09K 19/18 | (2006.01) | |
| C07D 239/26 | (2006.01) | |
| C09K 19/32 | (2006.01) | |
| C09K 19/34 | (2006.01) | |

(52) U.S. Cl.
CPC .......... C09K 19/18 (2013.01); C07D 239/26 (2013.01); C09K 19/322 (2013.01); C09K 19/3458 (2013.01); C09K 2019/188 (2013.01); C09K 2219/11 (2013.01)

(58) Field of Classification Search
CPC .. C09K 19/18; C09K 19/3458; C09K 19/322; C09K 2019/11; C09K 2019/188; G02F 1/1333; C07D 239/26
USPC .......... 252/299.01, 299.6, 299.61; 428/1.1
See application file for complete search history.

(56) References Cited

U.S. PATENT DOCUMENTS

| | | | |
|---|---|---|---|
| 5,454,975 A | * | 10/1995 | Reiffenrath .......... C07D 239/26 252/299.61 |
| 7,361,288 B2 | | 4/2008 | Lussem et al. |
| 7,563,492 B2 | | 7/2009 | Yanai |

(Continued)

FOREIGN PATENT DOCUMENTS

| | | |
|---|---|---|
| CN | 102140350 A | 8/2011 |
| CN | 104685025 A | 6/2015 |

(Continued)

OTHER PUBLICATIONS

International Search Report for PCT/EP2013/003628 dated Feb. 18, 2014.
(Continued)

*Primary Examiner* — Geraldina Visconti
(74) *Attorney, Agent, or Firm* — Millen White Zelano & Branigan

(57) ABSTRACT

The present invention relates to a liquid-crystal medium which comprises a component A which consists of one or more compounds selected from the group of the formulae I-M and I-U

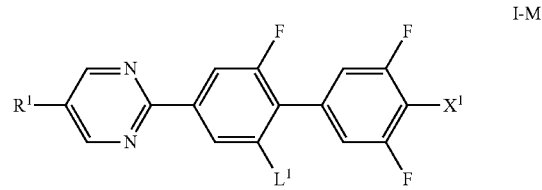

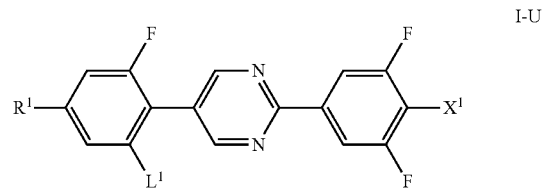

in which the parameters have the respective meanings given in the claims or in the text, and to the corresponding, novel mesogenic compounds and to the preparation thereof. The present invention likewise relates to the use of these liquid-crystal media, in particular in components for high-frequency technology, and to components of this type which contain media according to the invention, and to the production and use of these components. The components according to the invention are suitable, in particular, as phase shifters in the microwave and millimeter wave region, for microwave and millimeter wave array antennae and very particularly for so-called tuneable "reflectarrays".

15 Claims, No Drawings

(56) References Cited

U.S. PATENT DOCUMENTS

| | | | |
|---|---|---|---|
| 8,221,854 B2 * | 7/2012 | Czanta | ............... C09K 19/3444 252/299.61 |
| 8,262,930 B2 | 9/2012 | Shu et al. | |
| 2005/0067605 A1 | 3/2005 | Lussem et al. | |
| 2007/0108409 A1 | 5/2007 | Yanai et al. | |
| 2010/0127213 A1 | 5/2010 | Czanta et al. | |
| 2011/0019119 A1 | 1/2011 | Shu et al. | |
| 2015/0247089 A1 * | 9/2015 | Wittek | ............... C09K 19/0275 252/299.61 |
| 2016/0002533 A1 | 1/2016 | Manabe | |

FOREIGN PATENT DOCUMENTS

| | | |
|---|---|---|
| DE | 4327749 A1 | 2/1995 |
| DE | 102004029429 A1 | 2/2005 |
| DE | 102011119900 A1 | 7/2012 |
| EP | 1788064 A1 | 5/2007 |
| EP | 1785466 B1 | 3/2009 |
| EP | 1788064 B1 | 3/2009 |
| JP | 2005120208 A | 5/2005 |
| JP | 2007161995 A | 6/2007 |
| WO | 2004029697 A1 | 4/2004 |
| WO | 2009115226 A1 | 9/2006 |
| WO | 2009115226 A1 | 9/2009 |

OTHER PUBLICATIONS

English Abstract for JP2005120208, Publication Date: May 12, 2005.

English Abstract for DE102011119900, Publication Date: Jul. 26, 2012.

Search Report for corresponding CN application 201380066310 dated Aug. 18, 2016.

English Machine translation for WO2004029697, Publication Date: Apr. 8, 2004 to Merck.

English translation for DE4327749, Publication Date: Feb. 23, 1995 to Merck.

English translation of CN102140350A, publication date Aug. 3, 2011 to Beijing Bayi Space LCD.

Search Report for corresponding JP application 2015-548265 dated Dec. 1, 2017.

* cited by examiner

LIQUID-CRYSTALLINE MEDIA, COMPONENTS FOR HIGH-FREQUENCY TECHNOLOGY, AND MESOGENIC COMPOUNDS

AREA OF THE INVENTION

The present invention relates to liquid-crystalline media, in particular for high-frequency technology, especially components for high-frequency devices, in particular antennas, especially for the gigahertz region and the terahertz region, which are operated in the microwave or millimeter wave region. These components use particular liquid-crystalline, chemical compounds or liquid-crystalline media composed thereof for, for example, the phase shifting of microwaves for tuneable phased-array antennas or for tuneable cells of microwave antennas based on "reflectarrays". In addition, the present invention relates to novel mesogenic compounds.

Prior Art and Problem to be Solved

Liquid-crystalline media have long been utilised in electro-optical displays (liquid crystal displays—LCDs) in order to display information.

Compounds of the Formulae

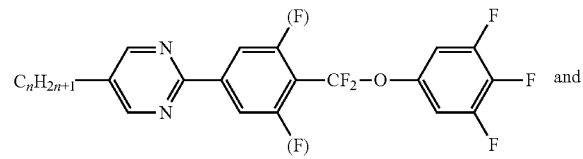

and

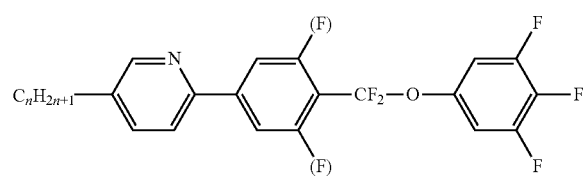

are e.g. proposed for liquid crystalline media for IPS displays in WO 2008/128623 A1.

Bistolan compounds, also known as triphenyldiacetylenes, having an additional alkyl substitution on the central phenylene ring are adequately known to the person skilled in the art.

For example, Wu, S.-T., Hsu, C.-S. and Shyu, K.-F., Appl. Phys. Lett., 74 (3), (1999), pages 344-346, discloses various liquid-crystalline bistolan compounds containing a lateral methyl group, of the formula

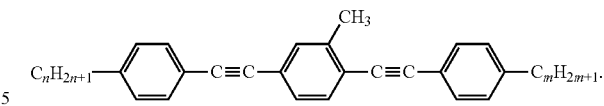

Besides liquid-crystalline bistolan compounds of this type containing a lateral methyl group, Hsu, C. S., Shyu, K. F., Chuang, Y. Y. and Wu, S.-T., Liq. Cryst., 27 (2), (2000), pages 283-287, also discloses corresponding compounds containing a lateral ethyl group and proposes the use thereof, inter alia, in liquid crystal optically phased arrays.

Dabrowski, R., Kula, P., Gauza, S., Dziadiszek, J., Urban, S. and Wu, S.-T., IDRC 08, (2008), pages 35-38, mentions dielectrically neutral bistolan compounds with and without a lateral methyl group on the central ring besides the strongly dielectrically positive isothiocyanatobistolan compounds of the formula

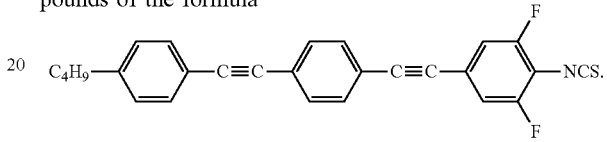

Compounds containing three C—C triple bonds, such as, for example, the compound

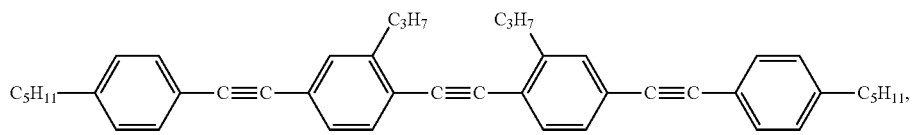

are mentioned in JP 2003-207631 A) and are proposed for use in optical films, polarisers and in liquid crystals of the light-scattering type.

However, liquid-crystalline media have recently also been proposed for use in components for microwave technology, as described, for example, in DE 10 2004 029 429 A and in JP 2005-120208 (A).

An industrially valuable application of liquid-crystalline media in high-frequency technology is based on their property that their dielectric properties can be controlled, particularly for the gigahertz region and the terahertz region, by a variable voltage. This enables the construction of tuneable antennas which contain no moving parts (Gaebler, A., Moessinger, A., Goelden, F., et al., "Liquid Crystal-Reconfigurable Antenna Concepts for Space Applications at Microwave and Millimeter Waves", International Journal of Antennas and Propagation, Volume 2009, Article ID 876989, (2009), pages 1-7, DOI: 10.1155/2009/876989).

Penirschke, A., Müller, S., Scheele, P., Weil, C., Wittek, M., Hock, C. and Jakoby, R.: "Cavity Perturbation Method for Characterisation of Liquid Crystals up to 35 GHz", 34$^{th}$ European Microwave Conference—Amsterdam, pp. 545-548, describe, inter alia, the properties of the known single liquid-crystalline substance K15 (also called 4-n-pentyl-4'-cyanobiphenyl or PP-5-N, Merck KGaA, Germany) at a frequency of 9 GHz.

DE 10 2004 029 429 A describes the use of liquid-crystal media in microwave technology, inter alia in phase shifters. DE 10 2004 029 429 A has already investigated liquid-crystalline media with respect to their properties in the corresponding frequency range.

For use in high-frequency technology, liquid-crystalline media having particular, hitherto rather unusual, unconventional properties, or combinations of properties, are required.

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (likewise Merck KGaA, Germany).

DE 10 2004 029 429 A describes the use of liquid-crystal media in microwave technology, inter alia in phase shifters. DE 10 2004 029 429 A has already investigated liquid-crystalline media with respect to their properties in the corresponding frequency range. In addition, it mentions liquid-crystalline media which comprise compounds of the formulae

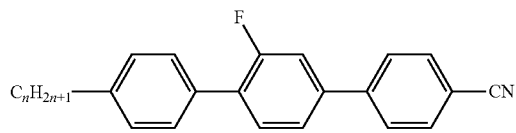

besides compounds of the formulae

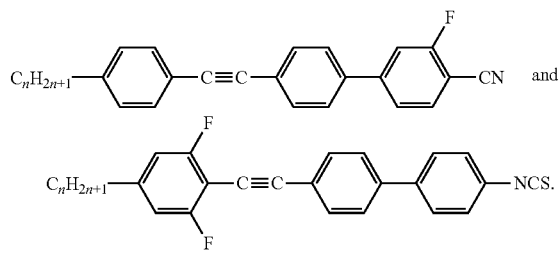

Liquid-crystal media which comprise, for example, compounds of the formula

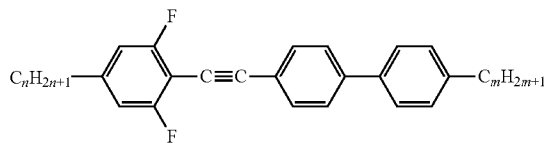

are proposed for use in components for high-frequency technology, for example, in A. Lapanik, "Single compounds and mixtures for microwave applications, Dielectric, microwave studies on selected systems", dissertation, Technical University of Darmstadt, 2009, (D17), A. Lapanik, F. Golden, S. Müller, A. Penirschke, R. Jakoby and W. Haase, *Frequenz*, in print, "Highly birefringent nematic mixtures at room temperature for microwave applications", A. Lapanik, F. Golden, S. Müller, R. Jakoby and W. Haase, *Journal of Optical Engineering*, submitted for publication, and in the following, hitherto unpublished patent applications: DE 10 2009 051 892.4, DE 10 2010 025 572.6, DE 10 201 0 045 370.6 and DE 10 2010 051 508.0.

However, the compositions known to date are afflicted with serious disadvantages. Besides other deficiencies, most of them result in disadvantageously high losses and/or inadequate phase shift or inadequate material quality ($\eta$).

Novel liquid-crystalline media having improved properties are thus necessary. In particular, the loss in the microwave region and/or millimeter wave region must be reduced and the material quality improved.

In addition, there is a demand for an improvement in the low-temperature behaviour of the liquid-crystalline media and thus also of the components. Both an improvement in the operating properties and also in the shelf life are necessary here.

Thus, there is a considerable demand for liquid-crystalline media having suitable properties for corresponding practical applications.

PRESENT INVENTION

Surprisingly, it has now been found that it is possible to achieve components for high-frequency technology which do not have the disadvantages of the prior-art materials, or at least only do so to a considerably reduced extent, if selected liquid-crystalline media are employed.

PRESENT INVENTION

Surprisingly, it now has been found that mesogenic media comprising a first component, component A, consisting of one or more compounds of selected from the group of formulae I-M and I-U

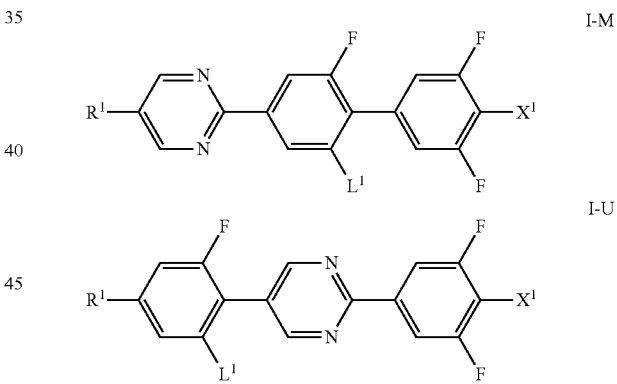

wherein $R^1$ is alkyl, which is straight chain or branched, preferably has 1 to 20 C-atoms, is unsubstituted, mono- or poly-substituted by F, Cl or CN, preferably by F, and in which one or more $CH_2$ groups are optionally replaced, in each case independently from one another, by —O—, —S—, —$NR^{01}$—, —$SiR^{01}R^{02}$—, —CO—, —COO—, —OCO—, —OCO—O—, —S—CO—, —CO—S—, —$CY^{01}$=$CY^{02}$— or —C≡C— in such a manner that O and/or S atoms are not linked directly to one another, preferably n-alkyl or n-alkoxy with 1 to 9 C-atoms, preferably with 2 to 5 C-atoms, alkenyl, alkenyloxy or alkoxyalkyl with 2 to 9 C-atoms, preferably with 2 to 5 C-atoms or halogenated alkyl, halogenated alkenyl or halogenated alkoxy with preferably up to 9 C-atoms, preferably mono fluorinated, di-fluorinated or oligofluorinated alkyl, alkenyl or alkoxy with preferably up to 9

C-atoms, most preferably n-alkyl, n-alkoxy, alkenyl, alkenyloxy or alkoxyalkyl with preferably up to 9 C-atoms, $L^1$ is H or F, preferably F, $X^1$ is F, CN or $CF_3$, preferably F or CN, most preferably CN, $Y^{01}$ and $Y^{02}$ are, independently of each other, F, Cl or CN, and alternatively one of them may be H, and $R^{01}$ and $R^{02}$ are, independently of each other, H or alkyl with 1 to 12 C-atoms, amongst which chiral compounds are encompassed, too, allow to realize media with an acceptably high clearing point and/or a rather high stability of the voltage holding ratio against temperature and/or UV-load and in particular against the latter.

The present invention further relates in a preferred embodiment to liquid-crystalline media, which additionally to the compounds of formulae I-M and/or I-U comprise one or more compounds of the formula I,

in which

denotes

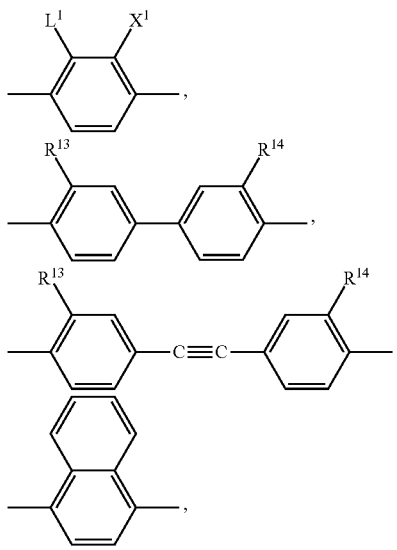

preferably

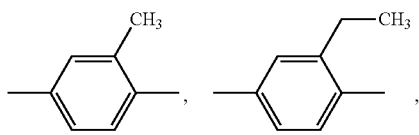

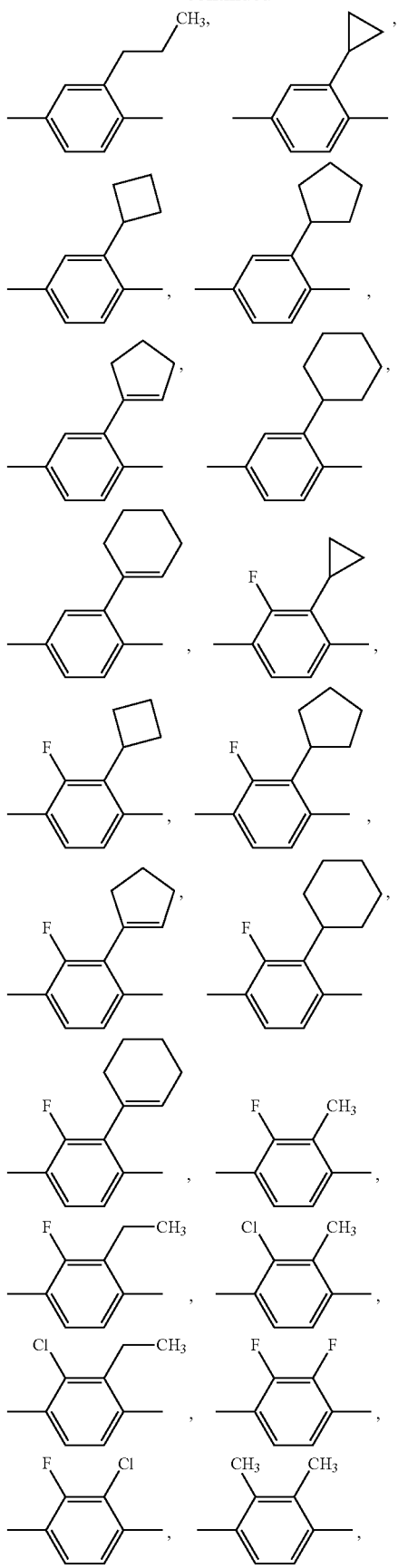

-continued

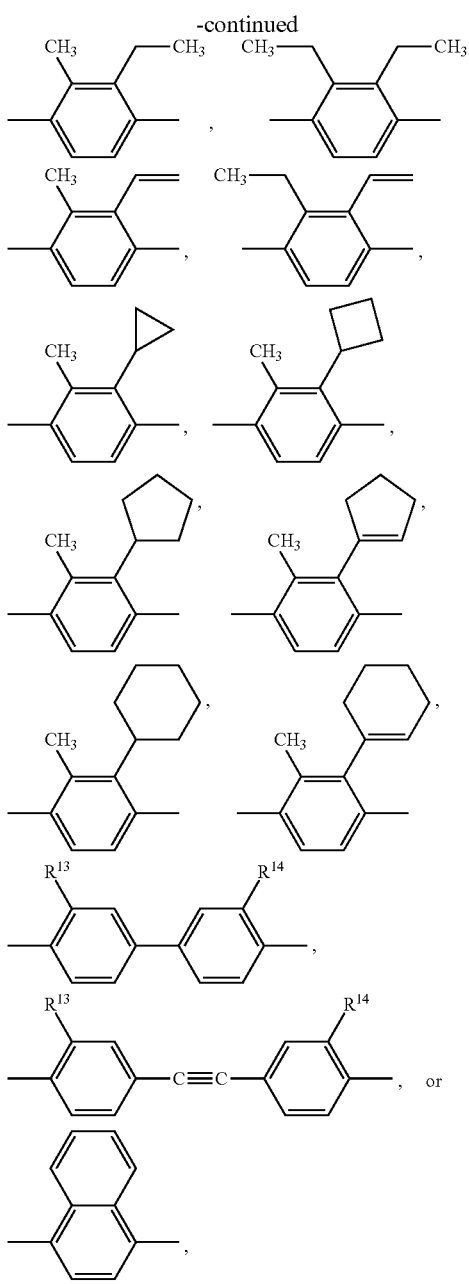

particularly preferably

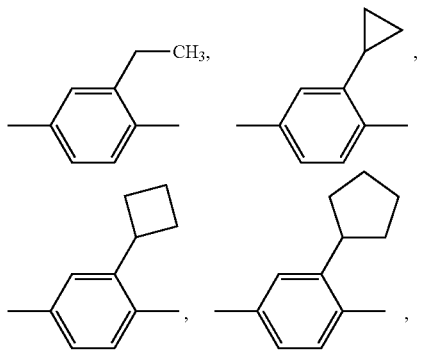

-continued

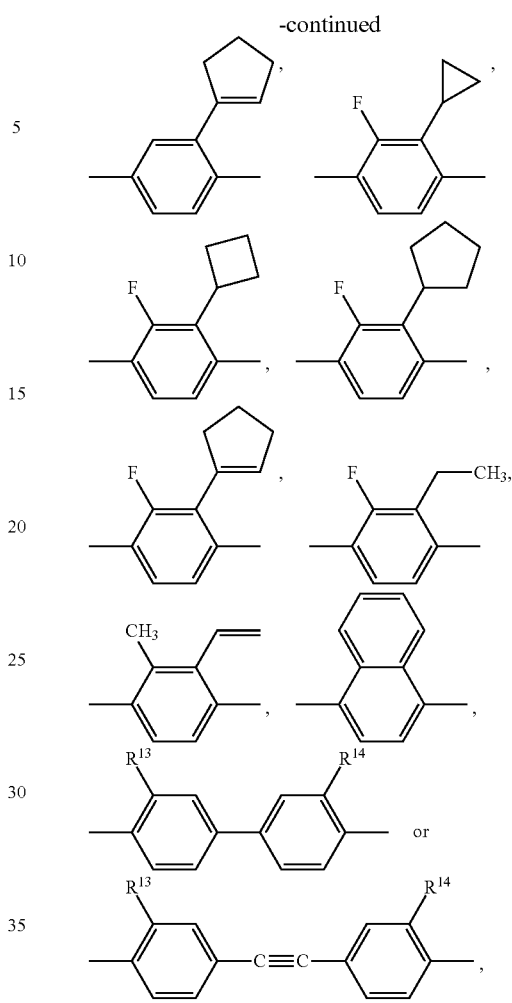

$L^1$ denotes alkyl having 1 to 6 C atoms, cycloalkyl having 3 to 6 C atoms or cycloalkenyl having 4 to 6 C atoms, preferably $CH_3$, $C_2H_5$, n-$C_3H_7$ (—$(CH_2)_2CH_3$), i-$C_3H_7$ (—$CH(CH_3)_2$), cyclopropyl, cyclobutyl, cyclohexyl, cyclopent-1-enyl or cyclohex-1-enyl, and particularly preferably $CH_3$, $C_2H_5$, cyclopropyl or cyclobutyl, $X^1$ denotes H, alkyl having 1 to 3 C atoms or halogen, preferably H, F or Cl, and particularly preferably H or F and very particularly preferably F, $R^{11}$ to $R^{14}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of $R^{13}$ and $R^{14}$ or both also denote H, preferably $R^{11}$ and $R^{12}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably $R^{11}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably $R^{12}$ denotes unfluorinated alkyl or unfluorinated alkoxy, each having 1 to 7 C atoms, and preferably $R^{13}$ and $R^{14}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of $R^{13}$ and $R^{14}$ denotes n-alkyl, particularly preferably methyl, ethyl or n-propyl, and the other denotes H or n-alkyl, particularly preferably H, methyl, ethyl or n-propyl.

The liquid-crystal media according to the invention are eminently suitable for use in components for high-frequency technology or for the microwave region and/or millimeter wave region of the electromagnetic spectrum. The present invention relates to this use of the media and to these components.

In a first preferred embodiment of the present invention, the component for high-frequency technology contains a liquid-crystal medium which comprises a component A which consists of one, two or more compounds of the formula I-M and/or I-U.

In accordance with a further preferred embodiment of the present invention, the component for high-frequency technology contains a liquid-crystalline medium comprising a first component, component A, which consists of one or more compounds of the above-mentioned formulae I-M and/or I-U, and one or more further components selected from the group of components B to F defined below, a component, component B, consisting of one or more compounds of formula I, a strongly dielectrically positive component, component C, which has a dielectric anisotropy of 10.0 or more, a strongly dielectrically negative component, component D, which has a dielectric anisotropy of −5.0 or less, a further component, component E, which has a dielectric anisotropy in the range from more than −5.0 to less than 10.0 and consists of compounds having seven or more, preferably eight or more, five- or six-membered rings, and a further component, component F, which likewise has a dielectric anisotropy in the range from more than −5.0 to less than 10.0 and consists of compounds having up to six five- or six-membered rings.

Typical examples of five-membered rings are

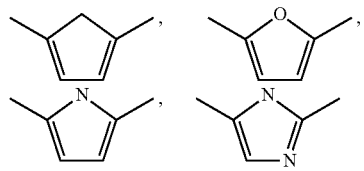

and others.

Typical examples of six-membered rings are

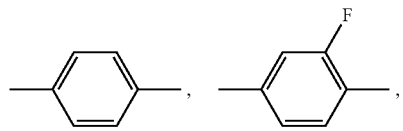

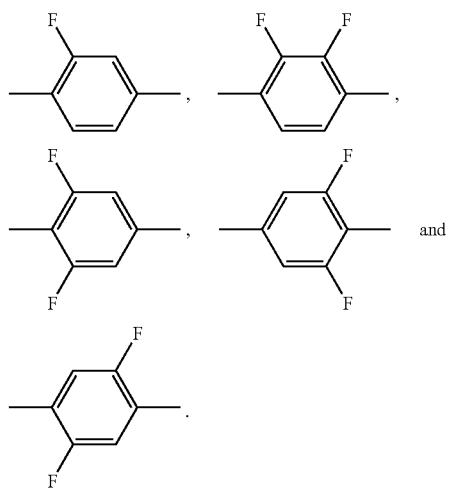

The five- and six-membered rings also include saturated and partially saturated rings, as well as heterocyclic rings.

For the purposes of the present application, condensed ring systems which consist of two of these rings, i.e. two five-membered rings, one five-membered ring or two six-membered rings, such as, for example,

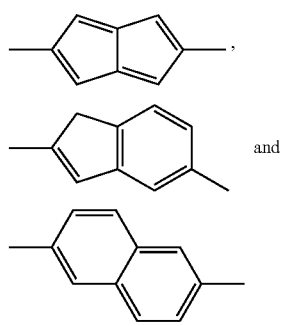

are counted as one of these five- or six-membered rings on assignment of the compounds to components B or E.

Correspondingly, condensed ring systems which consist of a combination of three or more of these rings which are incorporated into the molecule in the longitudinal direction, such as, for example,

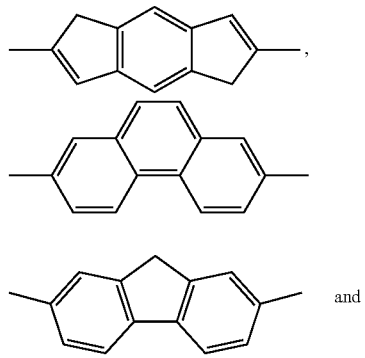

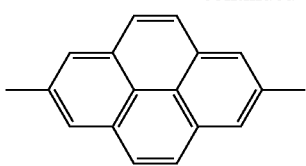

are counted as two of these five- or six-membered rings.

By contrast, condensed ring systems which are incorporated into the molecule in the transverse direction, such as, for example,

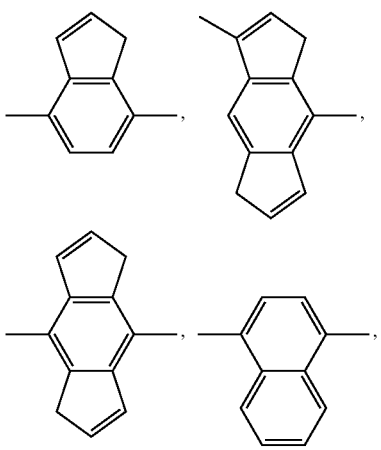

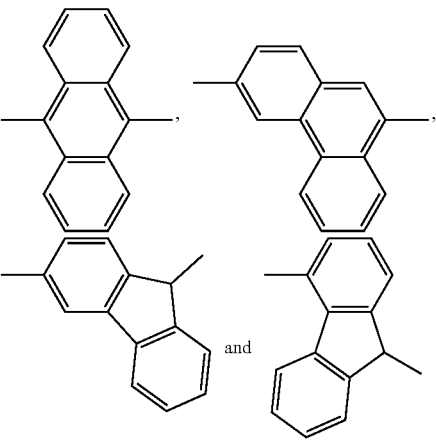

are counted as one of these five- or six-membered rings.

The present invention likewise relates to the directly preceding liquid-crystalline media and to those described below, and to the use thereof in electro-optical displays and in particular in components for high-frequency technology.

In a preferred embodiment of the present invention, the liquid-crystal medium comprises one or more compounds of the formula I, preferably selected from the group of the compounds of the formulae I-1 to I-4, preferably of the formulae I-1 and/or I-2 and/or I-3 and/or I-4, preferably of the formulae I-1 and I-2, these compounds more preferably predominantly consist thereof, even more preferably essentially consist thereof and very particularly preferably completely consist thereof:

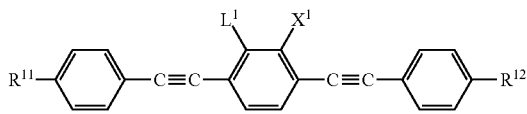  I-1

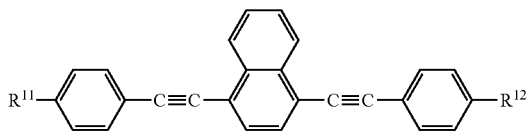  I-2

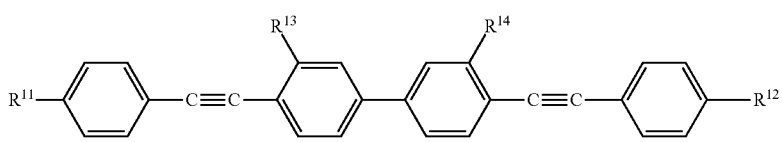  I-3

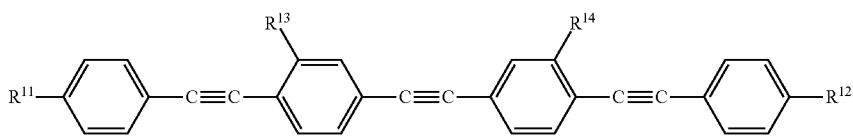  I-4

-continued

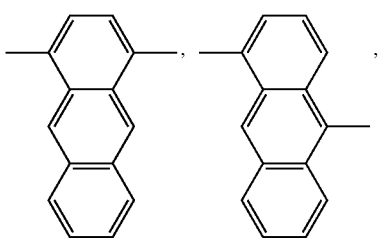

in which $L^1$ denotes alkyl having 1 to 6 C atoms, alkenyl having 2 to 6 C atoms, cycloalkyl having 3 to 6 C atoms or cycloalkenyl having 4 to 6 C atoms, preferably $CH_3$, $C_2H_5$, n-$C_3H_7$ (—$(CH_2)_2CH_3$), i-$C_3H_7$ (—$CH(CH_3)_2$), —CH=$CH_2$, cyclopropyl, cyclobutyl, cyclopentyl, cyclohexyl, cyclopent-1-enyl or cyclohex-1-enyl, and particularly preferably $CH_3$, $C_2H_5$, cyclopropyl or cyclobutyl, $X^1$ denotes H, alkyl having 1 to 3 C atoms or halogen, preferably H, F or Cl, and particularly preferably H or $CH_3$, even more preferably H or F and very particularly preferably F, and the other parameters have the respective meanings indicated above for formula I, and preferably $R^{11}$ denotes unfluorinated alkyl having 1 to 7 C atoms, and
$R^{12}$ denotes unfluorinated alkyl having 1 to 7 C atoms or unfluorinated alkoxy having 1 to 7 C atoms.

In a particularly preferred embodiment of the present invention, the liquid-crystal medium comprises one or more compounds of the formula I-1, preferably selected from the group of the compounds of the formulae I-1a-1 to I-1a-12 and I-1b-1 to I-1b-12

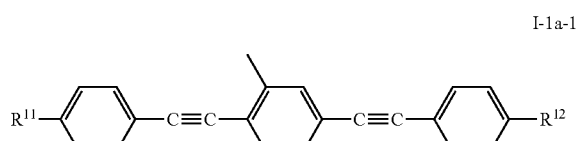
I-1a-1

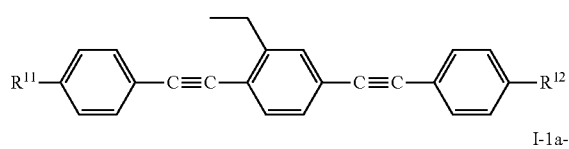
I-1a-2

I-1a-3

I-1a-4

I-1a-5

I-1a-6

I-1a-7

I-1a-8

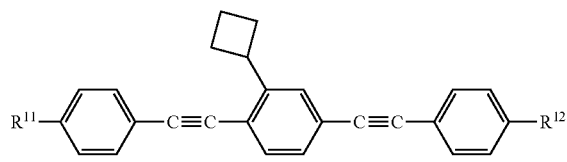

I-1a-9

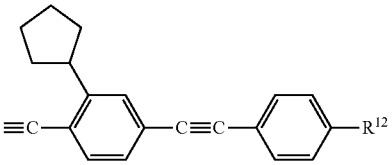
I-1a-10

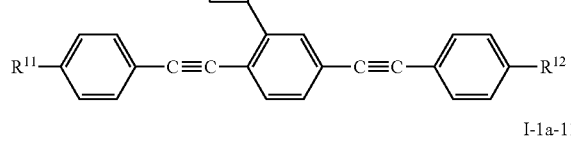
I-1a-11

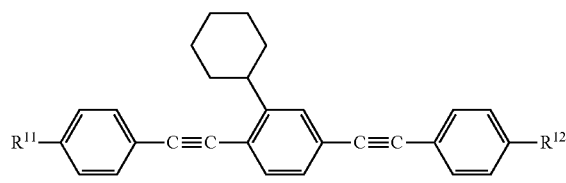
I-1a-12

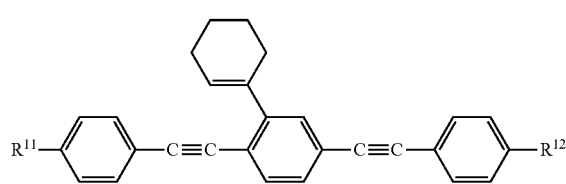
I-1b-1

I-1b-2

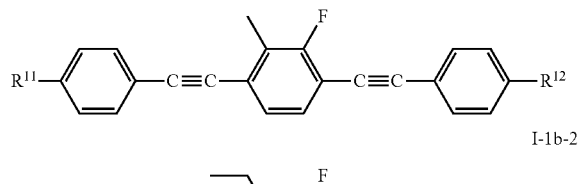
I-1b-3

I-1b-4

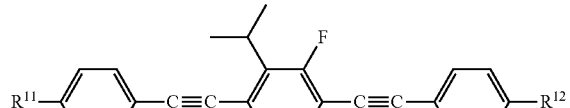
I-1b-5

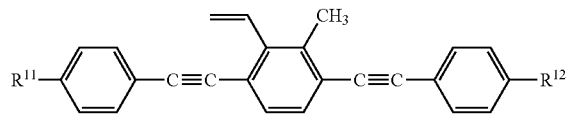

-continued

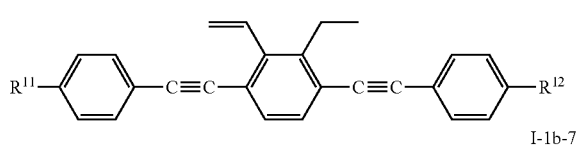
I-1b-6

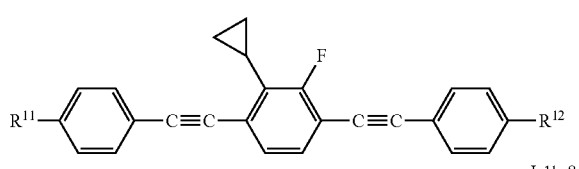
I-1b-7

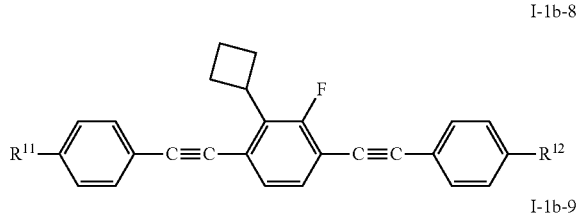
I-1b-8

I-1b-9

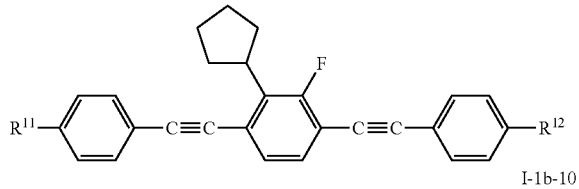
I-1b-10

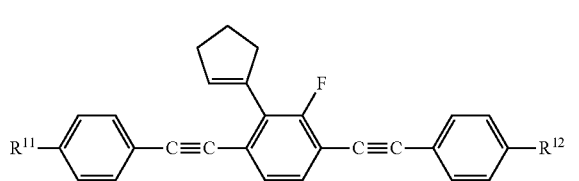
I-1b-11

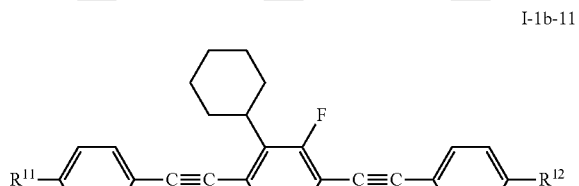
I-1b-12

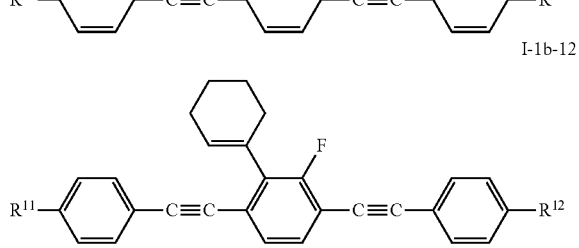

in which the parameters have the meanings as given above under formula I-1, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a very particularly preferred embodiment of the present invention, the liquid-crystal medium, or component B of the liquid-crystal medium, comprises one or more compounds of the formula I, preferably selected from the group of the compounds of the formulae I-1a-2, I-1a-5, I-1a-7, I-1a-8, I-1a-9, I-1a-10, I-1b-5, I-1b-7, I-1b-8, I-1b-9, I-1b-10, where the parameters have the meaning given above, and particularly preferably $R^{11}$ and $R^{12}$, independently of one another, denote unfluorinated alkyl having 1 to 7 C atoms or unfluorinated alkoxy having 1 to 6 C atoms, particularly preferably one of $R^{11}$ and $R^{12}$ denotes alkyl and the other denotes alkyl or alkoxy, and very particularly preferably $R^{11}$ and $R^{12}$ have different meanings from one another.

In a preferred embodiment of the present invention, the liquid-crystal medium, or component B of the liquid-crystal medium, comprises one or more compounds of the formula I-2, in which preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention, the liquid-crystal medium, or component B of the liquid-crystal medium, comprises one or more compounds of the formula I-3, preferably selected from the group of the compounds of the formulae I-3a-1 to I-3a-3 and I-3b-1 to I-3b-3, preferably I-3a-2, I-3b-2,

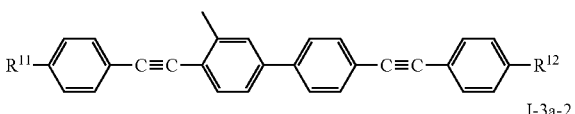
I-3a-1

I-3a-2

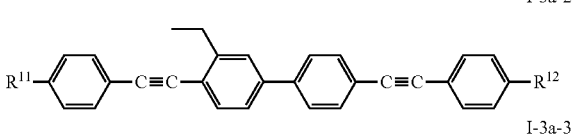
I-3a-3

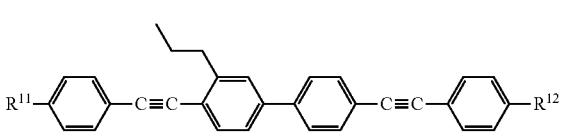
I-3b-1

I-3b-2

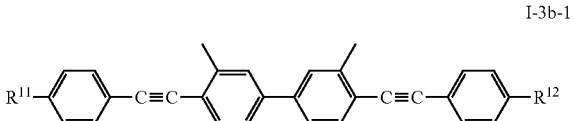
I-3b-3

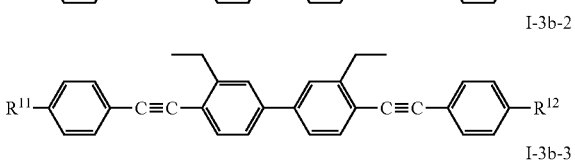

in which the parameters have the meanings given above under formula I-3, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

In a preferred embodiment of the present invention, the liquid-crystal medium, or component B of the liquid-crystal medium, comprises one or more compounds of the formula I-4, preferably selected from the group of the compounds of the formulae I-4a-1 to I-4a-3 and I-4b-1 to I-4b-3, preferably I-4b-2,

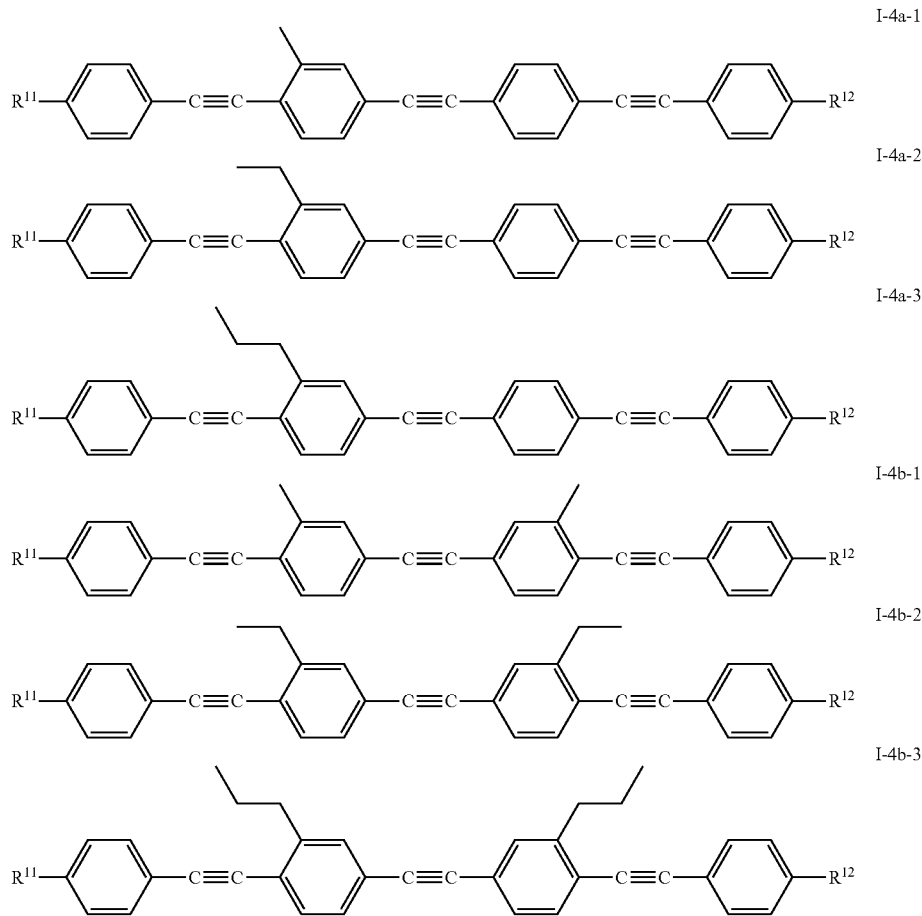

in which the parameters have the meanings given above under formula I-4, and preferably $R^{11}$ and $R^{12}$, independently of one another, denote an alkyl radical having 2 to 7 C atoms, for example a propyl or hexyl radical, or each denote a propyl, butyl, pentyl or hexyl radical.

The compounds of the formula I-1a can advantageously be prepared as evident from the following illustrative synthesis (Scheme 1-4):

Scheme 1. Illustrative synthesis of the compounds of the formula I (symmetrical).

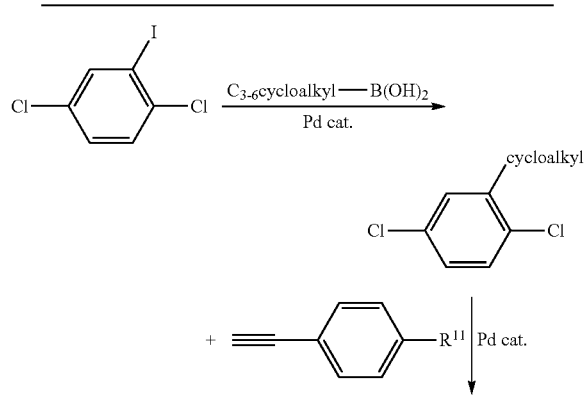

Scheme 2. Illustrative synthesis of the compounds of the formula I (symmertrical).

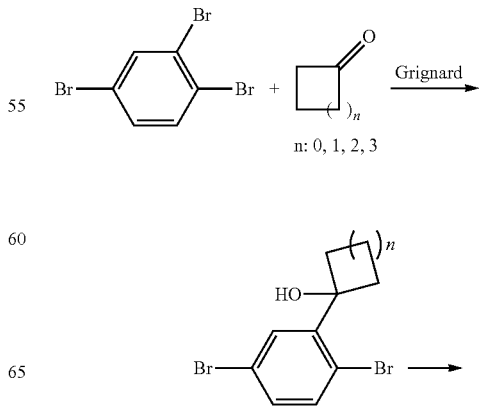

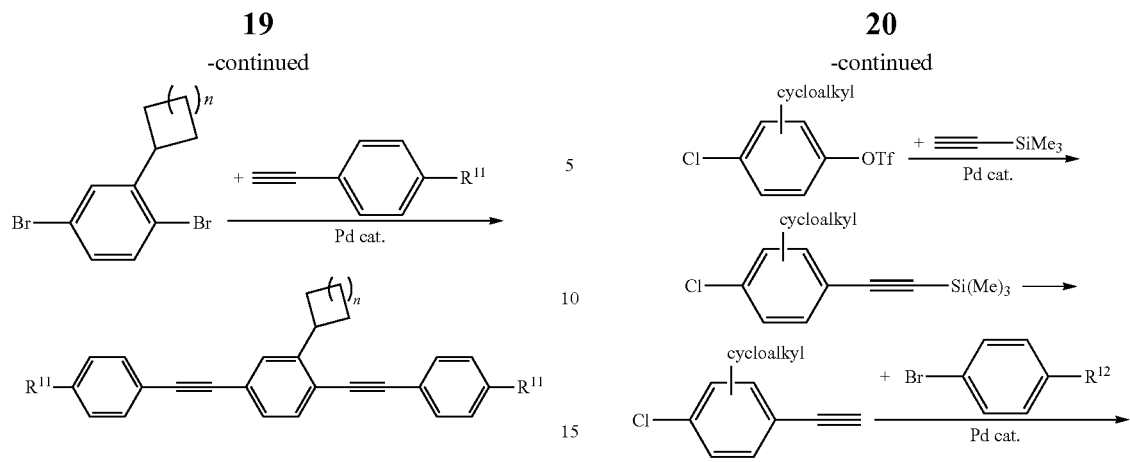

Scheme 3. Illustrative synthesis of the compounds of the formula I (asymmetrical).

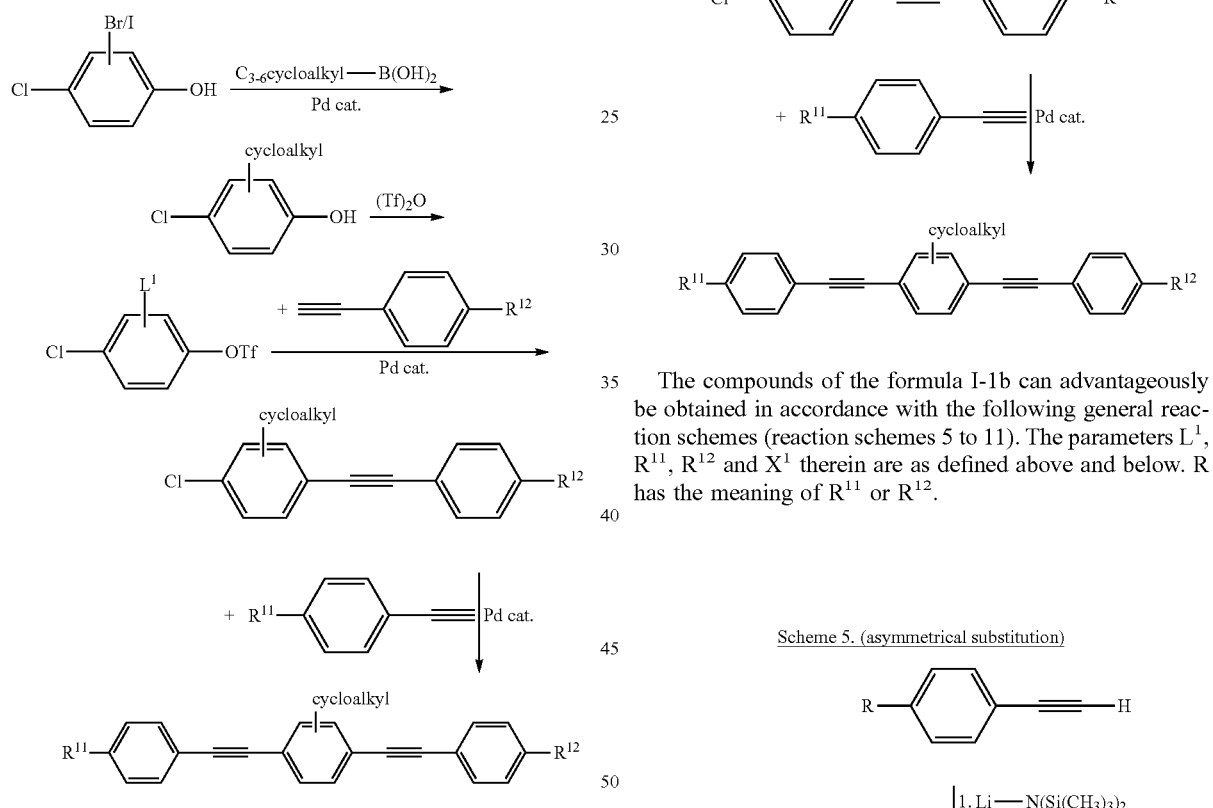

Scheme 4. Illustrative synthesis of the compounds of the formula I (asymmetrical).

The compounds of the formula I-1b can advantageously be obtained in accordance with the following general reaction schemes (reaction schemes 5 to 11). The parameters $L^1$, $R^{11}$, $R^{12}$ and $X^1$ therein are as defined above and below. R has the meaning of $R^{11}$ or $R^{12}$.

Scheme 5. (asymmetrical substitution)

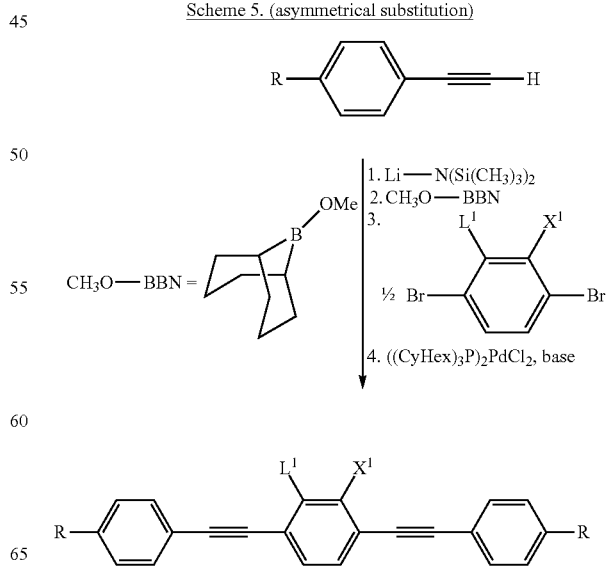

Scheme 6. (asymmetrical substitution)
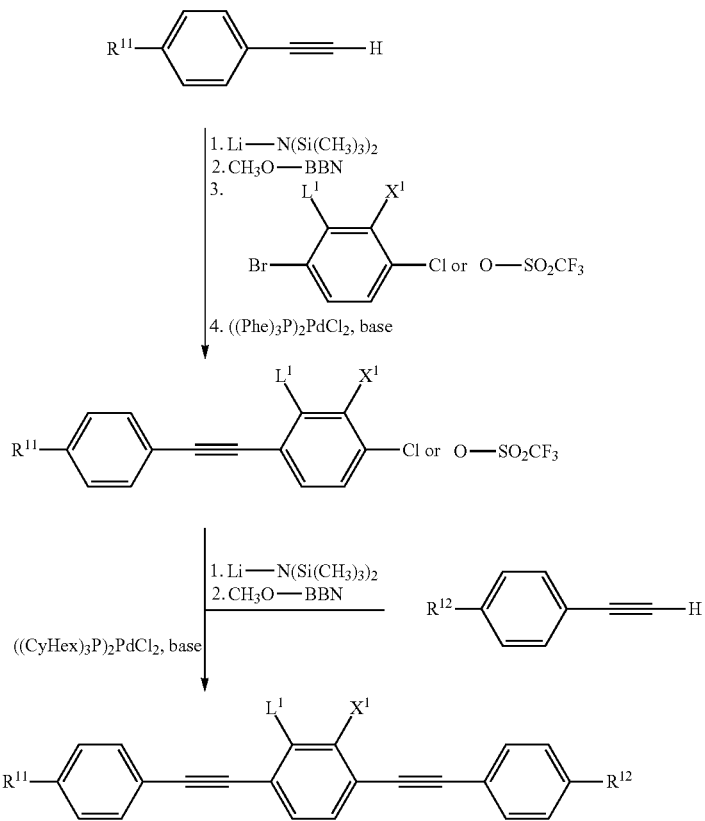
Schemes 7 to 11 show the synthesis of variously substituted central rings. The phenylalkynyl radicals here can be generalised to any desired substituted phenylalkynyl radicals.
Scheme 7.
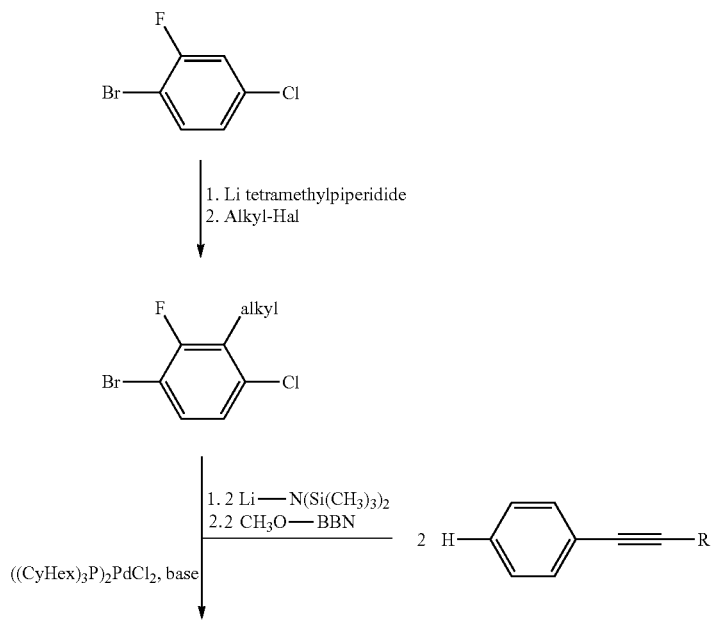

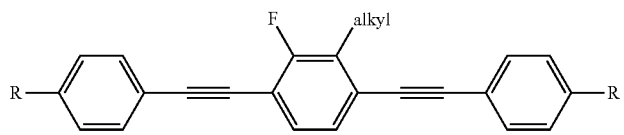
Scheme 8.
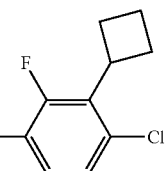
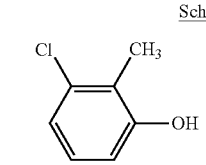
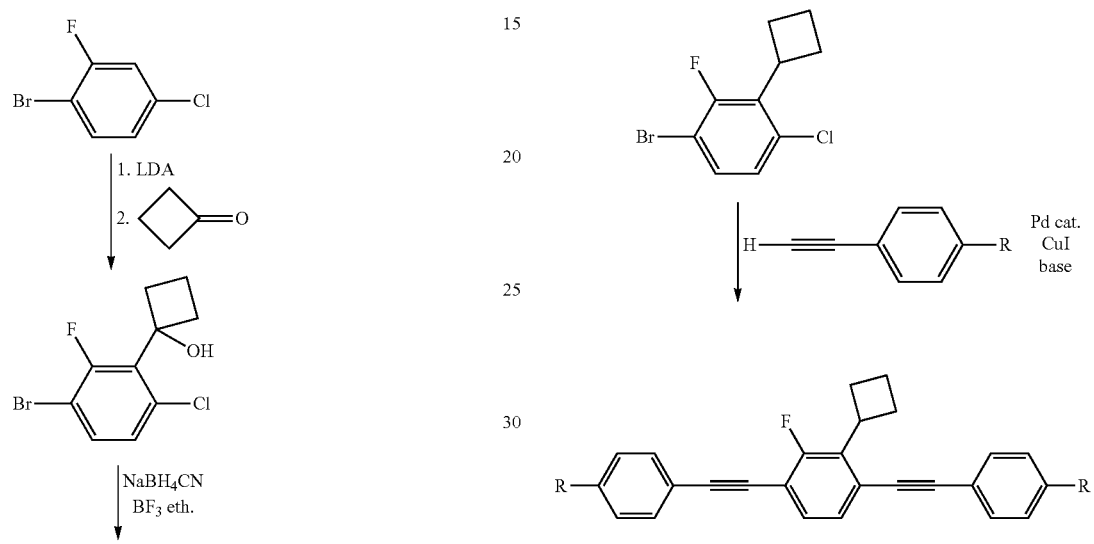
Scheme 9.
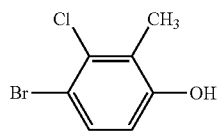
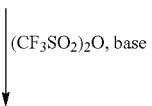

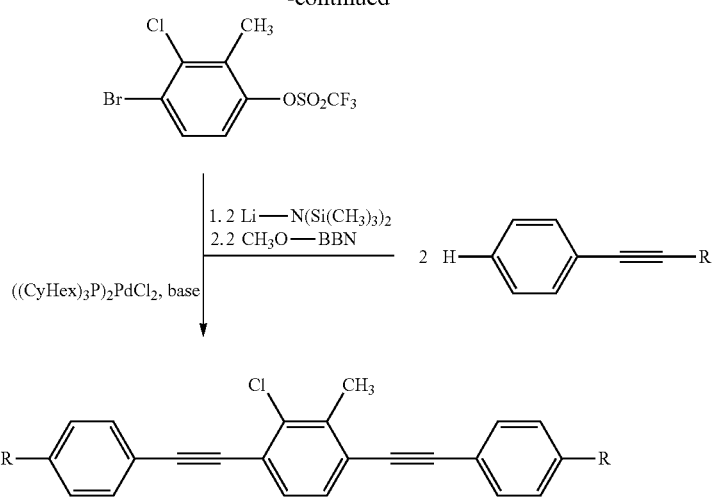
Scheme 10.
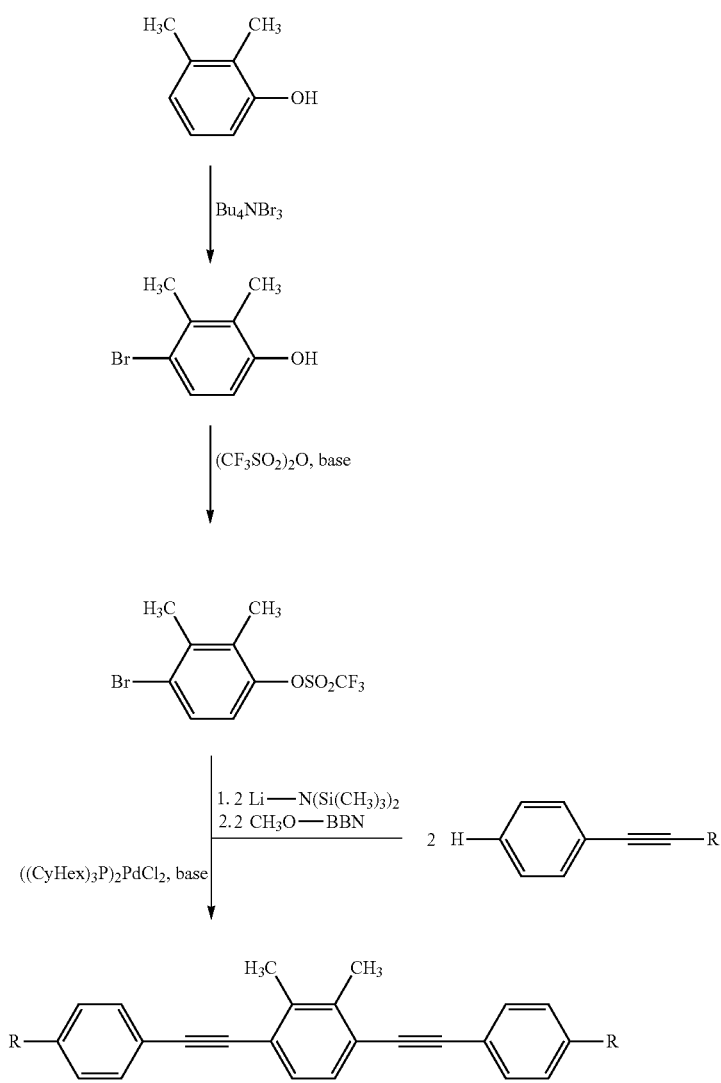

Scheme 11.
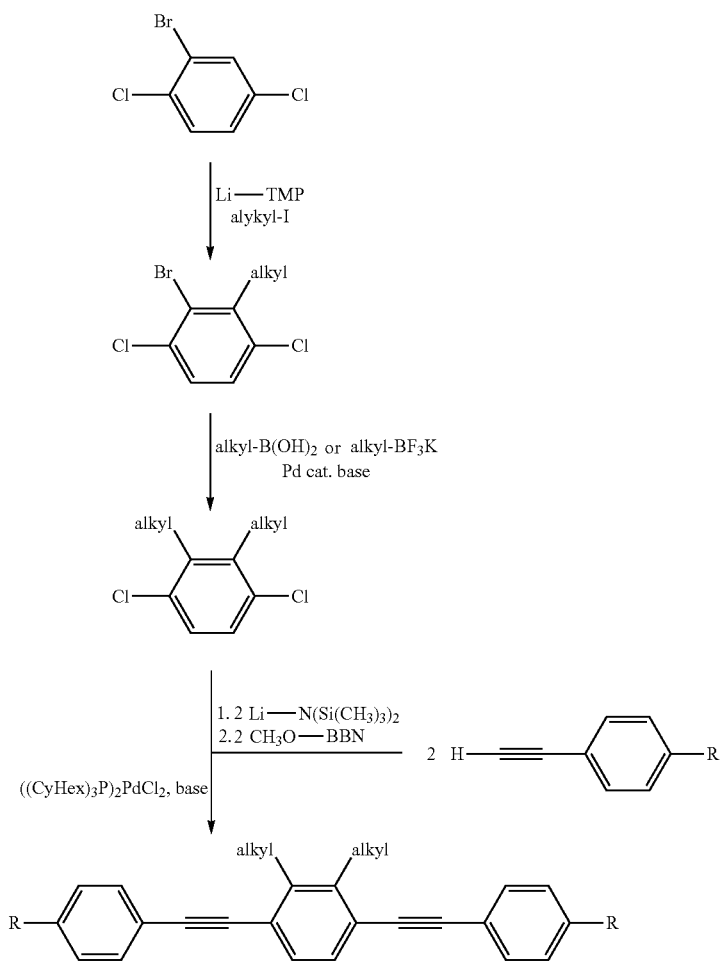
The compounds of the formula I-2 can advantageously be prepared as evident from the following illustrative synthesis (Scheme 12):
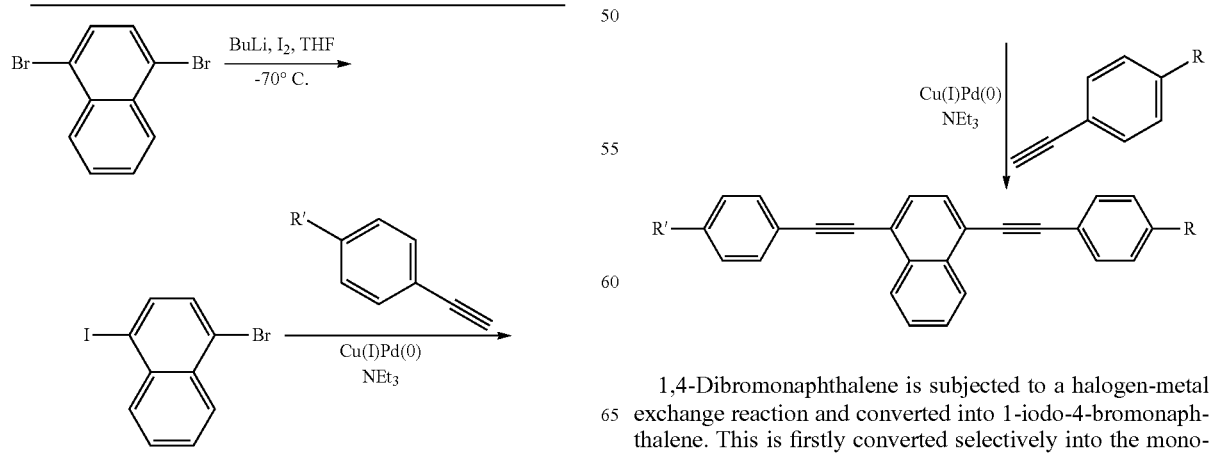
1,4-Dibromonaphthalene is subjected to a halogen-metal exchange reaction and converted into 1-iodo-4-bromonaphthalene. This is firstly converted selectively into the monofunctionalised acetylene-bridged compound in a Sonogashira coupling, followed by a second Sonogashira reaction, in which the target compounds of the formula I having two acetylene bridges are obtained. If the two groups R are identical, coupling to two equivalents of the acetylene compound can be carried out immediately instead of the iodination.

The compounds of the formulae I-3 and I-4 can advantageously be obtained in accordance with the following general reaction scheme (Reaction Scheme 13).

component A, component B, component C and component E and/or F, or
component A, component B and component D, or
component A, component B, component C and component D, or
component A, component B, component D and component E and/or F.

These media according to the invention preferably comprise a component C and no component D or vice versa.

Scheme 13. Illustrative synthesis of the compounds of the formulae I-3 and I-4, in which R has the meaning of $R^{11}$ or $R^{12}$ (symmetrical).

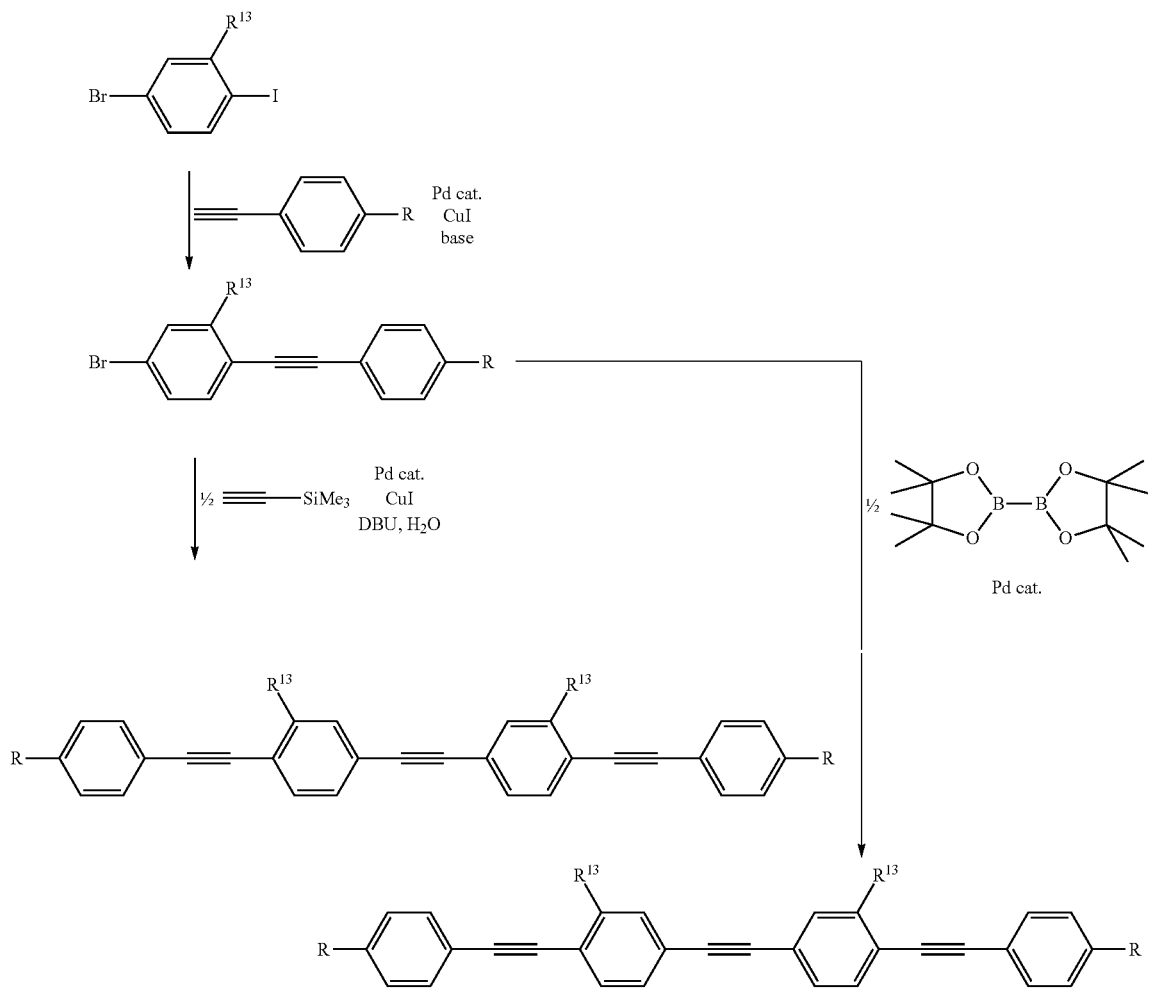

Besides component B, these media according to the invention preferably comprise a component selected from the two components C and C and optionally additionally component E and/or component F.

These media according to the invention preferably comprise two, three or four, particularly preferably two or three, components selected from the group of components A to F. These media preferably comprise
   component A and component B, or
   component A and component C, or
   component A, component C and component E and/or F, or
   component A and component D, or
   component A, component C and component D, or
   component A, component D and component E and/or F, or
   component A, component B and component C, or The strongly dielectrically positive component, component C, preferably has a dielectric anisotropy of 20.0 or more, more preferably 25.0 or more, particularly preferably 30.0 or more and very particularly preferably 40.0 or more.

The strongly dielectrically negative component, component D, preferably has a dielectric anisotropy of −7.0 or less, more preferably −8.0 or less, particularly preferably −10.0 or less and very particularly preferably −15.0 or less.

In a preferred embodiment of the present invention, component C comprises one or more compounds selected from the group of the compounds of the formulae IIA and IIB:

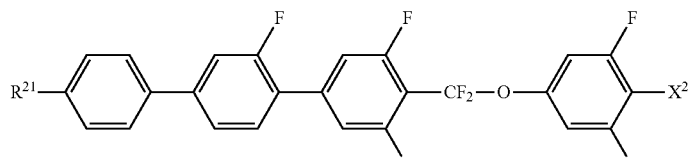

IIA

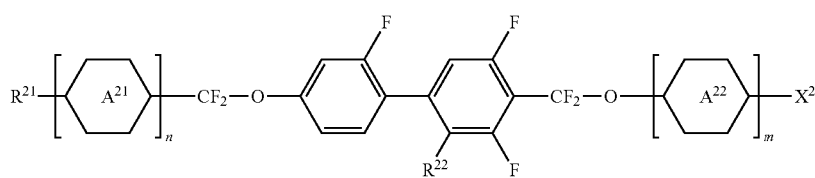

IIB $R^{21}$ denotes unfluorinated alkyl or unfluorinated alkoxy, each having 1 to 15 C atoms, or unfluorinated alkenyl, unfluorinated alkenyloxy or unfluorinated alkoxyalkyl, each having 2 to 15 C atoms, preferably alkyl, particularly preferably n-alkyl, $R^{22}$ denotes H, unfluorinated alkyl or unfluorinated alkoxy, each having 1 to 5, preferably 1 to 3, particularly preferably 3, C atoms,

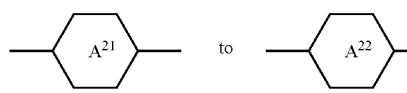 to 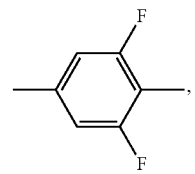, independently of one another and, if they occur more than once, these also in each case independently of one another, denote

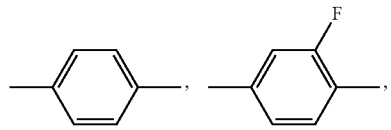

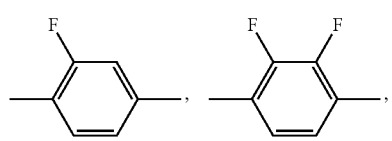

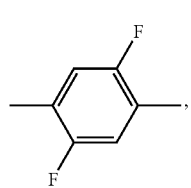

preferably

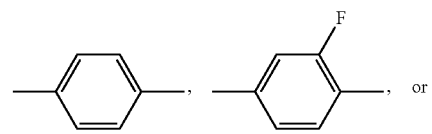

n and m, independently of one another, denote 1 or 2, preferably (n+m) denotes 3 or 4, and particularly preferably n denotes 2, $X^2$ denotes F, Cl, —$CF_3$ or —$OCF_3$, preferably F or Cl, particularly preferably F, $Y^2$ denotes F, Cl, —$CF_3$, —$OCF_3$ or CN, preferably CN, and $Z^2$ denotes H or F.

Preferred compounds of the formula IIA are the compounds of the corresponding sub-formula IIA-1

IIA-1

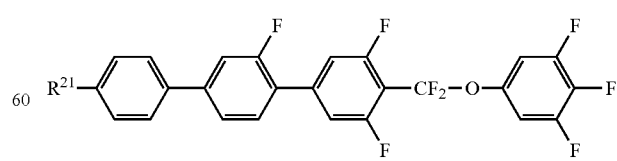

in which $R^{21}$ has the meaning given above.

Preferred compounds of the formula IIB are the compounds of the corresponding sub-formulae IIB-1 and IIB-2:

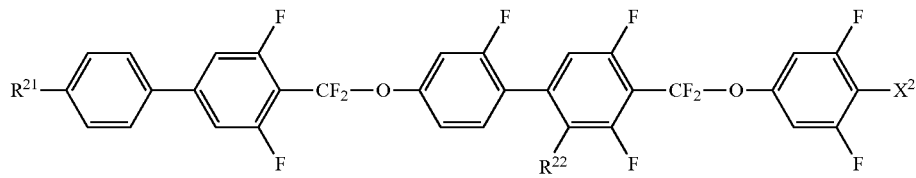

IIB-1

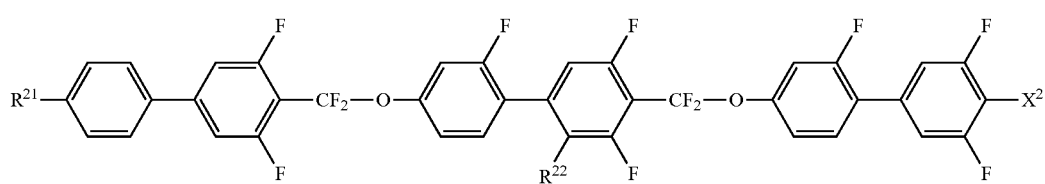

IIB-2 in which $R^{21}$, $R^{22}$ and $X^2$ have the respective meanings given above.

In a preferred embodiment of the present invention, component C comprises one or more compounds selected from the group of the compounds of the formulae IIIA and IIIB:

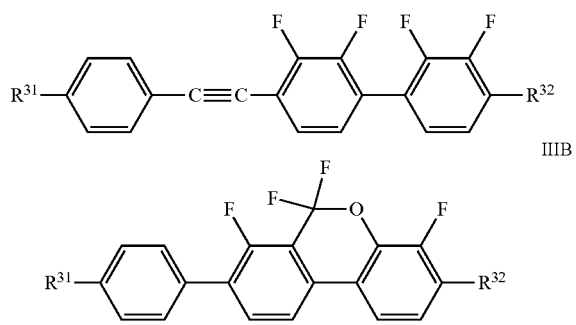

IIIA

IIIB in which $R^{31}$ and $R^{32}$, independently of one another, have the meanings indicated above for $R^{21}$ under formula IIA, and preferably $R^{31}$ denotes $C_nH_{2n+1}$ or $CH_2$=CH—$(CH_2)_Z$ and $R^{32}$ denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{31}$ and $R^{32}$) here are, in particular, ($C_nH_{2n+1}$ and $C_mH_{2m+1}$) and ($C_nH_{2n+1}$ and O—$C_mH_{2m+1}$).

Preferred compounds of the formula IIIB are the compounds of the sub-formulae IIIB-1 and IIIB-2:

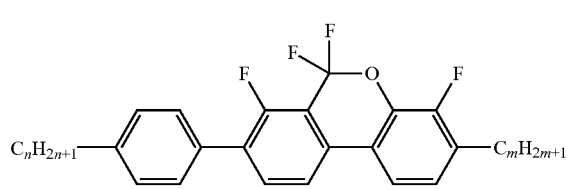

IIIB-1

-continued

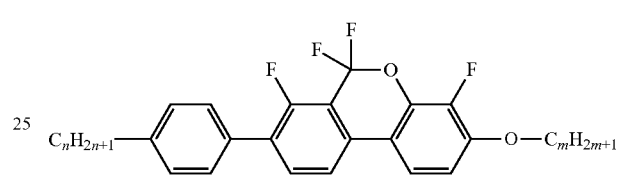

IIIB-2 in which n and m each have the meanings given above for formula IIIB and preferably, independently of one another, denote an integer in the range from 1 to 7.

In a preferred embodiment of the present invention, component E comprises one or more compounds of the following formula IV:

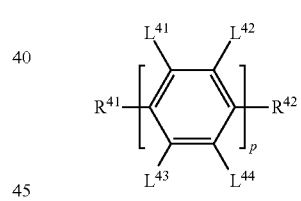

IV in which $R^{41}$ and $R^{42}$, independently of one another, have one of the meanings indicated above for $R^{11}$ under formula I, $L^{41}$ to $L^{44}$ on each appearance, in each case independently of one another, denote H, alkyl having 1 to 5 C atoms, F or Cl, and p denotes an integer in the range from 7 to 14, preferably from 8 to 12 and particularly preferably from 9 to 10, and preferably at least two of the substituents $L^{41}$ to $L^{44}$ present have a meaning other than H, and $R^{41}$ denotes $C_nH_{2n+1}$ or $CH_2$=CH—$(CH_2)_Z$, and $R^{42}$ denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

In a preferred embodiment of the present application, the liquid-crystal medium additionally comprises a further component, component F, which preferably consists of one or more compounds selected from the group of the compounds of the formulae V to IX:

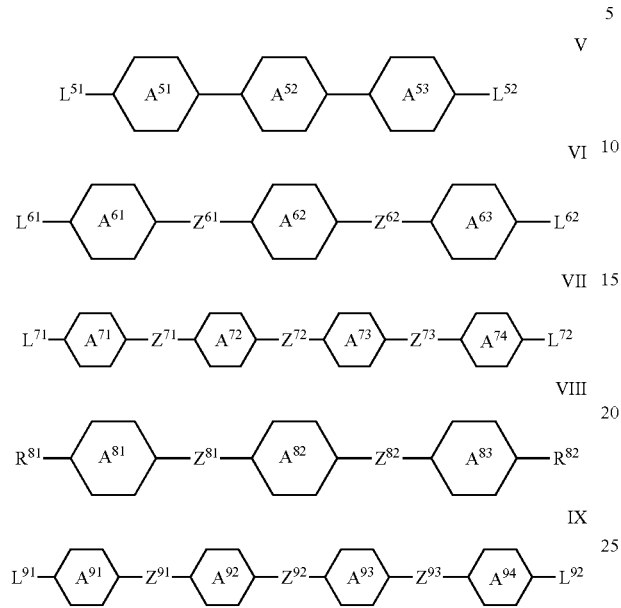

in which $L^{51}$ denotes $R^{51}$ or $X^{51}$, $L^{52}$ denotes $R^{52}$ or $X^{52}$, $R^{51}$ and $R^{52}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{51}$ and $X^{52}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and

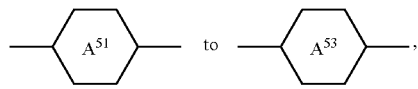

independently of one another, denote

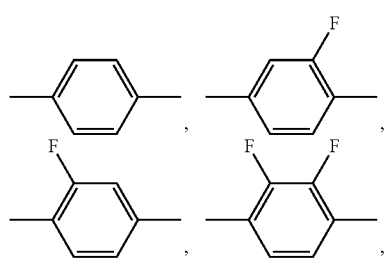

preferably

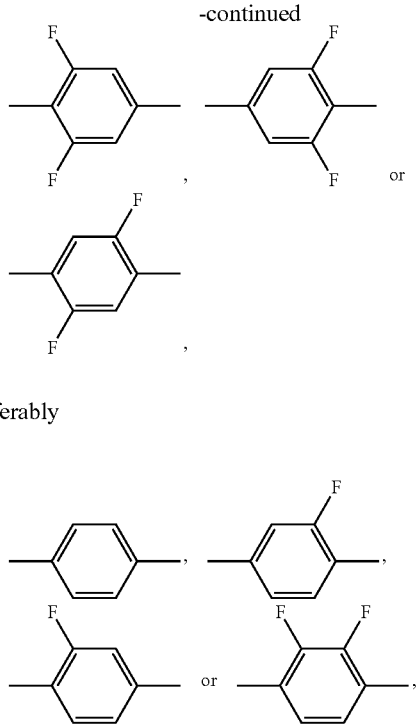

$L^{61}$ denotes $R^{61}$ and, in the case where $Z^{61}$ and/or $Z^{62}$ denote trans-CH=CH— or trans-CF=CF—, alternatively also denotes $X^{61}$, $L^{62}$ denotes $R^{62}$ and, in the case where $Z^{61}$ and/or $Z^{62}$ denote trans-CH=CH— or trans-CF=CF—, alternatively also denotes $X^{62}$, $R^{61}$ and $R^{62}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{61}$ and $X^{62}$, independently of one another, denote F or Cl, —CN, —NCS, —SF$_5$, fluorinated alkyl or alkoxy having 1 to 7 C atoms or fluorinated alkenyl, alkenyloxy or alkoxyalkyl having 2 to 7 C atoms, preferably —NCS, one of $Z^{61}$ and $Z^{62}$ denotes trans-CH=CH—, trans-CF=CF— or —C≡C— and the other, independently thereof, denotes trans-CH=CH—, trans-CF=CF— or a single bond, preferably one of them denotes —C≡C— or trans-CH=CH— and the other denotes a single bond, and

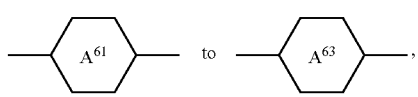

independently of one another, denote

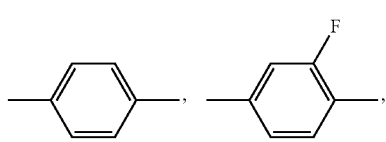

-continued

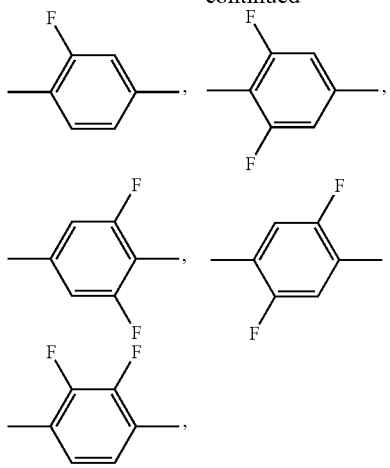

preferably

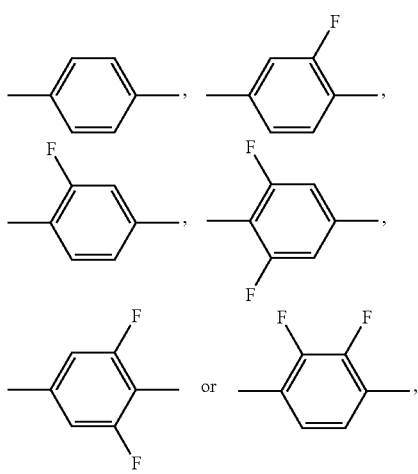

L$^{71}$ denotes R$^{71}$ or X$^{71}$,
L$^{72}$ denotes R$^{72}$ or X$^{72}$,
R$^{71}$ and R$^{72}$, independently of one another, denote H, unfluorinated alkyl or unfluorinated alkoxy having 1 to 17, preferably 3 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl,
X$^{71}$ and X$^{72}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and
Z$^{71}$ to Z$^{73}$, independently of one another, denote trans-CH═CH—, trans-CF═CF—, —C≡C— or a single bond, preferably one or more of them denote a single bond, particularly preferably all denote a single bond and —◯A$^{71}$◯— to —◯A$^{74}$◯—, independently of one another, denote

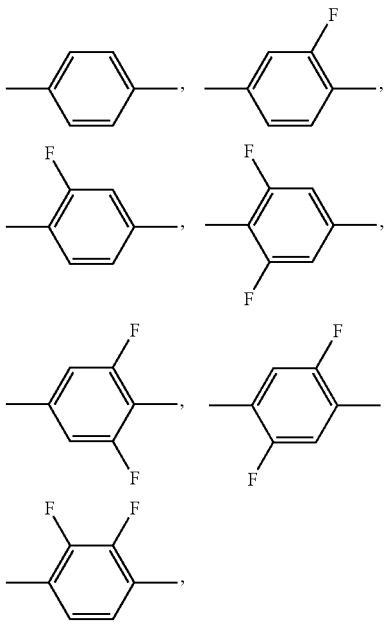

preferably

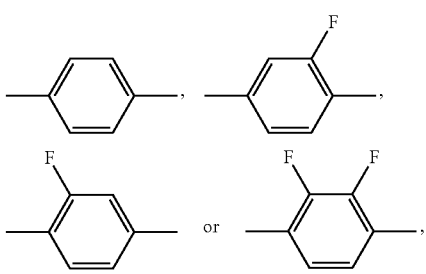

R$^{81}$ and R$^{82}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl,
one of
Z$^{81}$ and Z$^{82}$ denotes trans-CH═CH—, trans-CF═CF— or —C≡C— and the other, independently thereof, denotes trans-CH═CH—, trans-CF═CF— or a single bond, preferably one of them denotes —C≡C— or trans-CH═CH— and the other denotes a single bond, and

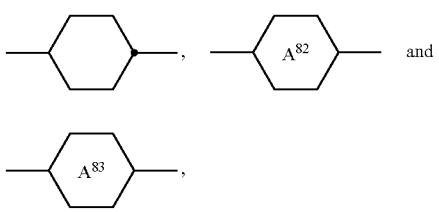

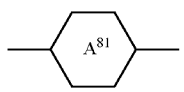

denotes
independently of one another, denote

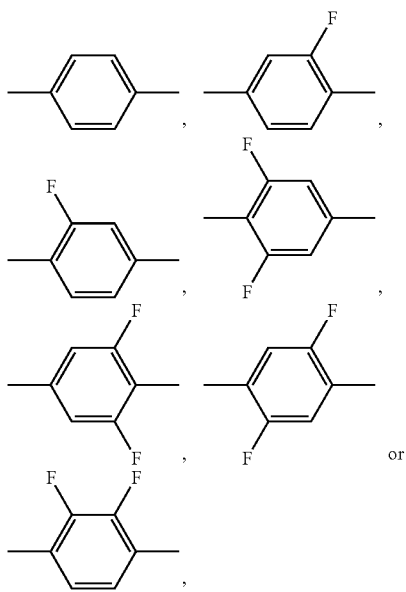

L$^{91}$ denotes R$^{91}$ or X$^{91}$,
L$^{92}$ denotes R$^{92}$ or X$^{92}$,
R$^{91}$ and R$^{92}$, independently of one another, denote H, unfluorinated alkyl or alkoxy having 1 to 15, preferably 3 to 10, C atoms or unfluorinated alkenyl, alkenyloxy or alkoxyalkyl having 2 to 15, preferably 3 to 10, C atoms, preferably unfluorinated alkyl or alkenyl,
X$^{91}$ and X$^{92}$, independently of one another, denote H, F, Cl, —CN, —NCS, —SF$_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and
Z$^{91}$ to Z$^{93}$, independently of one another, denote trans-CH=CH—, trans-CF=CF—, —C≡C— or a single bond, preferably one or more of them denotes a single bond, and particularly preferably all denote a single bond,

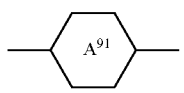

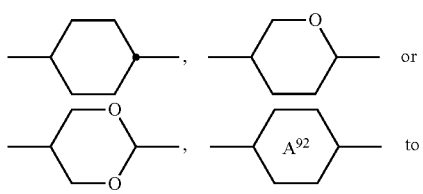

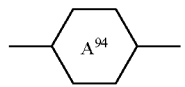

denotes
independently of one another, denote

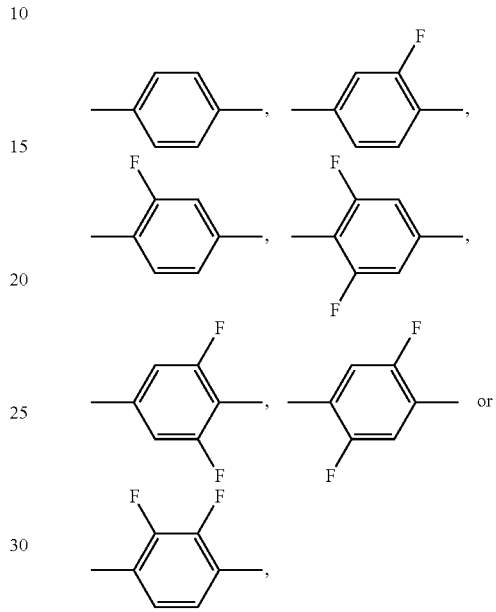

and where compounds of the formula IIIA are excluded from the compounds of the formula VI.

In a preferred embodiment of the present invention, the liquid-crystal medium comprises, more preferably predominantly consists of, even more preferably essentially consists of and very particularly preferably completely consists of one or more compounds of the formula V, preferably selected from the group of the compounds of the formulae V-1 to V-3, preferably of the formulae V-1 and/or V-2 and/or V-3, preferably of the formulae V-1 and V-2:

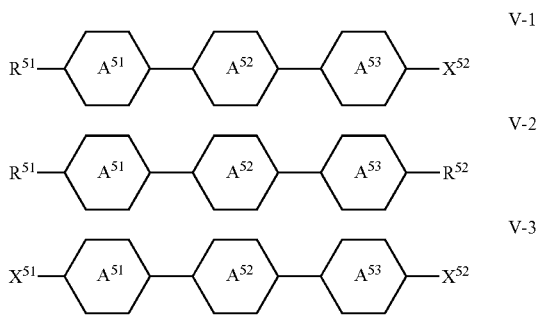

in which the parameters have the respective meanings indicated above for formula V and preferably
R$^{51}$ denotes unfluorinated alkyl having 1 to 7 C atoms or unfluorinated alkenyl having 2 to 7 C atoms,
R$^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —OCF$_3$, —CF$_3$, —CN, —NCS or —SF$_5$, preferably F, Cl, —OCF$_3$ or —CN.

The compounds of the formula V-1 are preferably selected from the group of the compounds of the formulae V-1a to V-1d, more preferably these compounds of the formula V predominantly consist, even more preferably essentially consist and very particularly preferably completely consist thereof:

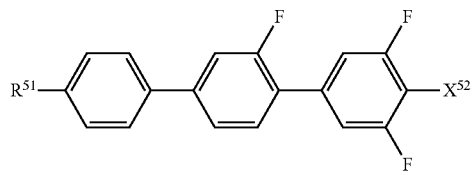

V-1a

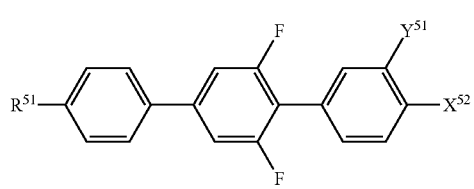

V-1b

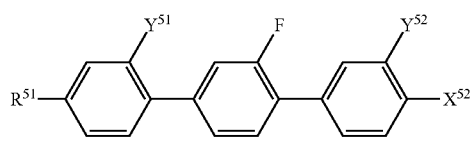

V-1c

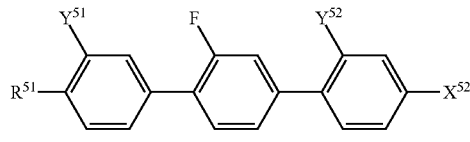

V-1d in which the parameters have the respective meanings indicated above for formula V-1 and in which $Y^{51}$ and $Y^{52}$, in each case independently of one another, denote H or F, and preferably $R^{51}$ denotes alkyl or alkenyl, and $X^{51}$ denotes F, Cl or —OCF$_3$.

The compounds of the formula V-2 are preferably selected from the group of the compounds of the formulae V-2a to V-2e and/or from the group of the compounds of the formulae V-2f and V-2g, more preferably these compounds of the formula V predominantly consist, even more preferably essentially consist and very particularly preferably completely consist thereof:

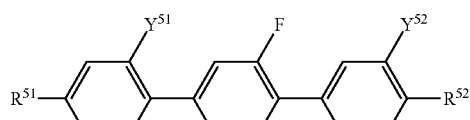

V-2a

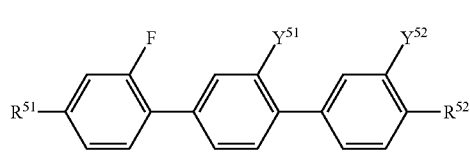

V-2b

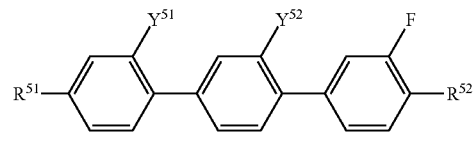

V-2c

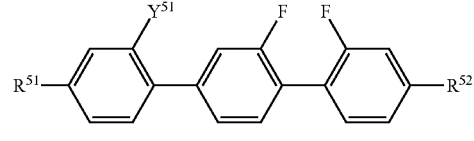

V-2d

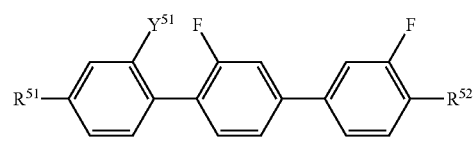

V-2e

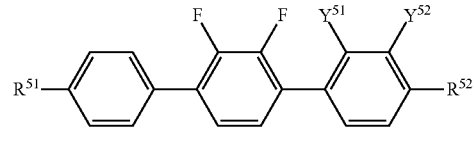

V-2f

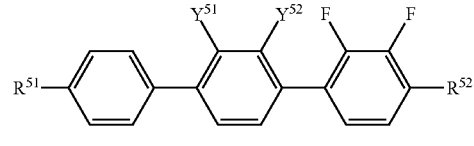

V-2g where in each case the compounds of the formula V-2a are excluded from the compounds of the formulae V-2b and V-2c, the compounds of the formula V-2b are excluded from the compounds of the formula V-2c and the compounds of the formula V-2e are excluded from the compounds of the formula V-2f, and in which the parameters have the respective meanings indicated above for formula V-1 and in which $Y^{51}$ and $Y^{52}$, in each case independently of one another, denote H or F, and preferably $R^{51}$ denotes alkyl or alkenyl, $X^{51}$ denotes F, Cl or —OCF$_3$, and preferably one of $Y^{51}$ and $Y^{52}$ denotes H and the other denotes H or F, preferably likewise denotes H.

The compounds of the formula V-3 are preferably compounds of the formula V-3a:

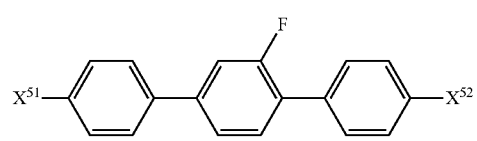

V-3a in which the parameters have the respective meanings indicated above for formula V-1 and in which preferably $X^{51}$ denotes F, Cl, preferably F, $X^{52}$ denotes F, Cl or —OCF$_3$, preferably —OCF$_3$.

In an even more preferred embodiment of the present invention, the compounds of the formula V are selected from the group of the compounds V-1a to V-1d, preferably selected from the group of the compounds V-1c and V-1d, more preferably these compounds of the formula V predominantly consist, even more preferably essentially consist and very particularly preferably completely consist thereof:

The compounds of the formula V-1a are preferably selected from the group of the compounds of the formulae V-1a-1 and V-1a-2, more preferably these compounds of the formula V predominantly consist, even more preferably essentially consist and very particularly preferably completely consist thereof:

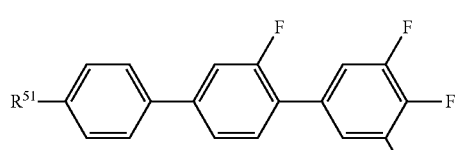

V-1a-1

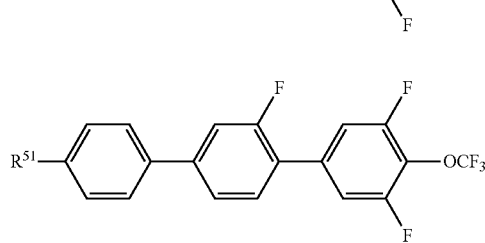

V-1a-2 in which
$R^{51}$ has the meaning indicated above and preferably denotes $C_nH_{2n+1}$, in which
n denotes an integer in the range from 0 to 7, preferably in the range from 1 to 5 and particularly preferably 3 or 7.

The compounds of the formula V-1b are preferably compounds of the formula V-1b-1:

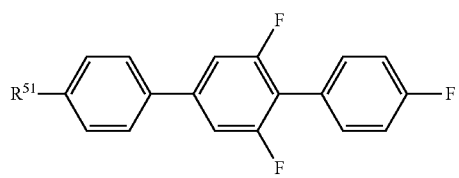

V-1b-1 in which
$R^{51}$ has the meaning indicated above and preferably denotes $C_nH_{2n+1}$, in which
n denotes an integer in the range from 0 to 15, preferably in the range from 1 to 7 and particularly preferably 1 to 5.

The compounds of the formula V-1c are preferably selected from the group of the compounds of the formulae V-1c-1 to V-1c-4, preferably selected from the group of the compounds of the formulae V-1c-1 and V-1c-2, more preferably these compounds of the formula V predominantly consist, even more preferably essentially consist and very particularly preferably completely consist thereof:

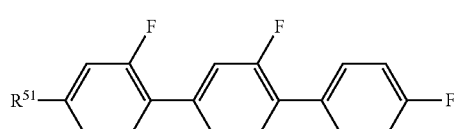

V-1c-1

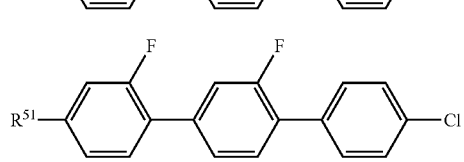

V-1c-2

-continued

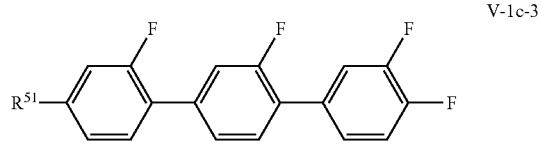

V-1c-3

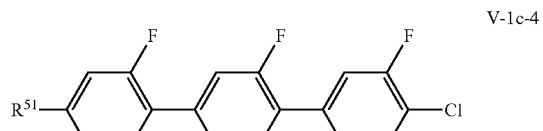

V-1c-4 in which
$R^{51}$ has the meaning indicated above and preferably denotes $C_nH_{2n+1}$, in which
n denotes an integer in the range from 0 to 15, preferably in the range from 1 to 7 and particularly preferably 1 to 5.

The compounds of the formula V-1d are preferably selected from the group of the compounds of the formulae V-1 d-1 and V-1 d-2, preferably the compound of the formula V-1 d-2, more preferably these compounds of the formula V predominantly consist, even more preferably essentially consist and very particularly preferably completely consist thereof:

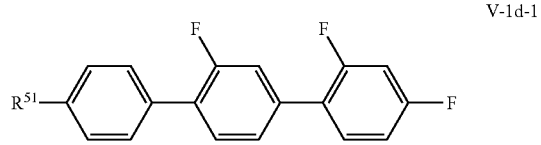

V-1d-1

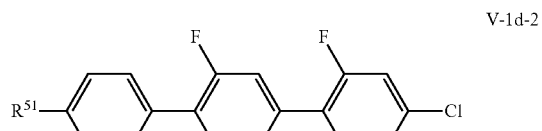

V-1d-2 in which
$R^{51}$ has the meaning indicated above and preferably denotes $C_nH_{2n+1}$, in which
n denotes an integer in the range from 0 to 15, preferably in the range from 1 to 7 and particularly preferably 1 to 5.

The compounds of the formula V-2a are preferably selected from the group of the compounds of the formulae V-2a-1 and V-2a-2, preferably the compounds of the formula V-2a-1, more preferably these compounds of the formula V predominantly consist, even more preferably essentially consist and very particularly preferably completely consist thereof:

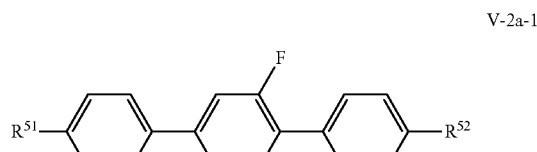

V-2a-1

-continued

V-2a-2

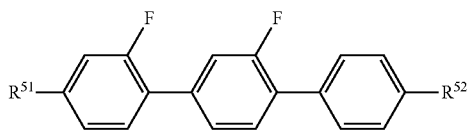

in which
R$^{51}$ has the meaning indicated above and preferably denotes C$_n$H$_{2n+1}$ or CH$_2$=CH—(CH$_2$)$_Z$, and
R$^{52}$ has the meaning indicated above and preferably denotes C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

Preferred combinations of (R$^{51}$ and R$^{52}$), in particular in the case of formula V-2a-1, are (C$_n$H$_{2n+1}$ and C$_m$H$_{2m+1}$), (C$_n$H$_{2n+1}$ and O—C$_m$H$_{2m+1}$), (CH$_2$=CH—(CH$_2$)$_Z$ and C$_m$H$_{2m+1}$), (CH$_2$=CH—(CH$_2$)$_Z$ and O—C$_m$H$_{2m+1}$) and (C$_n$H$_{2n+1}$ and (CH$_2$)$_Z$—CH=CH$_2$).

Preferred compounds of the formula V-2b are the compounds of the formula V-2b-1:

V-2b-1

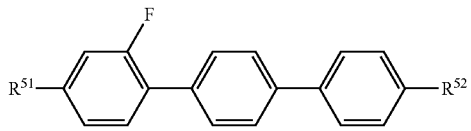

in which
R$^{51}$ has the meaning indicated above and preferably denotes C$_n$H$_{2n+1}$ or CH$_2$=CH—(CH$_2$)$_Z$, and
R$^{52}$ has the meaning indicated above and preferably denotes C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2c are the compounds of the formula V-2c-1:

V-2c-1

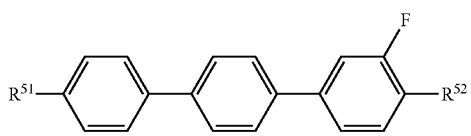

in which
R$^{51}$ has the meaning indicated above and preferably denotes C$_n$H$_{2n+1}$ or CH$_2$=CH—(CH$_2$)$_Z$, and
R$^{52}$ has the meaning indicated above and preferably denotes C$_m$H$_{2m+1}$ or O—C$_m$H$_{2m+1}$ or (CH$_2$)$_Z$—CH=CH$_2$, and in which n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2d are the compounds of the formula V-2d-1:

V-2d-1

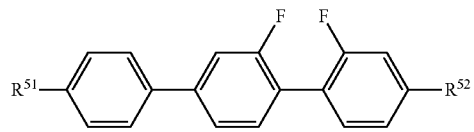

in which
R$^{51}$ has the meaning indicated above and preferably denotes C$_n$H$_{2n+1}$ or CH$_2$=CH—(CH$_2$)$_Z$, and
R$^{52}$ has the meaning indicated above and preferably denotes C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and C$_m$H$_{2m+1}$).

Preferred compounds of the formula V-2e are the compounds of the formula V-2e-1:

V-2e-1

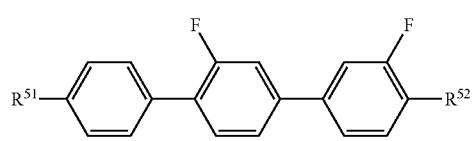

in which
R$^{51}$ has the meaning indicated above and preferably denotes C$_n$H$_{2n+1}$ or CH$_2$=CH—(CH$_2$)$_Z$, and
R$^{52}$ has the meaning indicated above and preferably denotes C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combination of (R$^{51}$ and R$^{52}$) here is, in particular, (C$_n$H$_{2n+1}$ and O—C$_m$H$_{2m+1}$).

Preferred compounds of the formula V-2f are the compounds of the formula V-2f-1:

V-2f-1

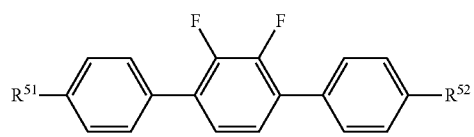

in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

Preferred compounds of the formula V-2g are the compounds of the formula V-2g-1:

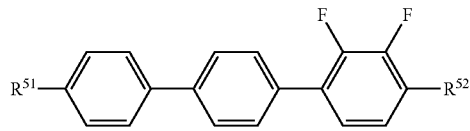

V-2g-1 in which

R$^{51}$ has the meaning indicated above and preferably denotes C$_n$H$_{2n+1}$ or CH$_2$=CH—(CH$_2$)$_z$, and R$^{52}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{51}$ and R$^{52}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and O—C$_m$H$_{2m+1}$).

The compounds of the formula VI are preferably selected from the group of the compounds of the formulae VI-1 to VI-4, more preferably these compounds of the formula VI predominantly consist, even more preferably essentially consist and very particularly preferably completely consist thereof:

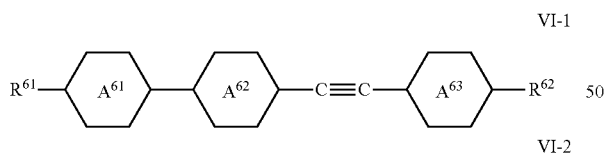

VI-1

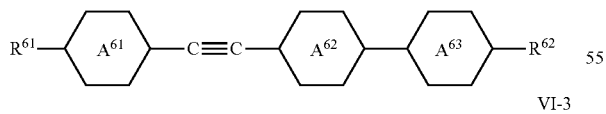

VI-2

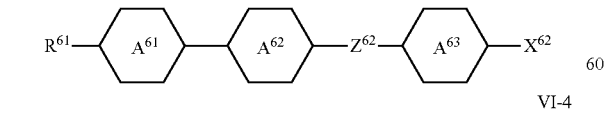

VI-3

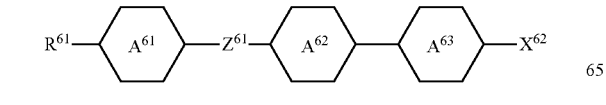

VI-4 in which

Z$^{61}$ and Z$^{62}$ denote trans-CH=CH— or trans-CF=CF—, preferably trans-CH=CH—, and the other parameters have the meaning given above under formula VI and preferably R$^{61}$ and R$^{62}$, independently of one another, denote H, unfluorinated alkyl or alkoxy having 1 to 7 C atoms or unfluorinated alkenyl having 2 to 7 C atoms, X$^{62}$ denotes F, Cl, —CN or —NCS, preferably —NCS, and one of

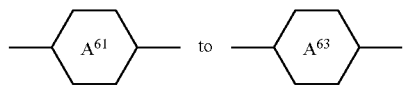

denotes

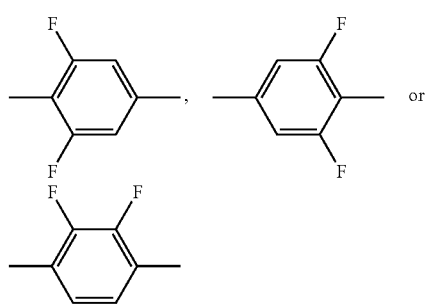

and the others, independently of one another, denote

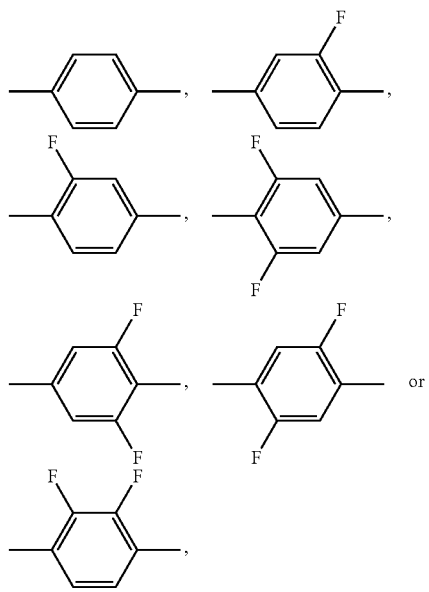

preferably

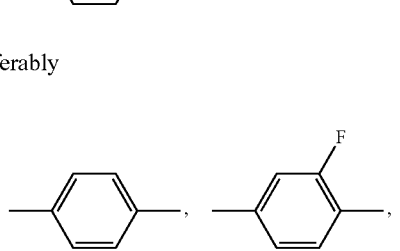

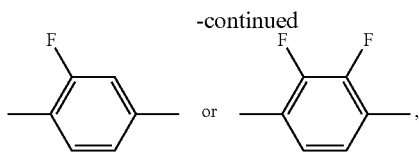

and preferably

R$^{61}$ denotes C$_n$H$_{2n+1}$ or CH$_2$=CH—(CH$_2$)$_z$, and

R$^{62}$ denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula VI-1 are preferably selected from the group of the compounds of the formulae VI-1a and VI-1b, preferably selected from compounds of the formula VI-1a, more preferably these compounds of the formula VI predominantly consist, even more preferably essentially consist and very particularly preferably completely consist thereof:

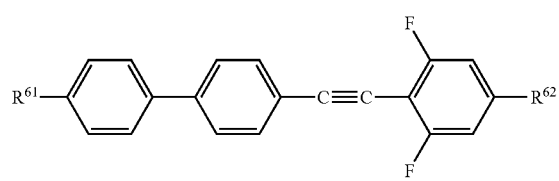

VI-1a

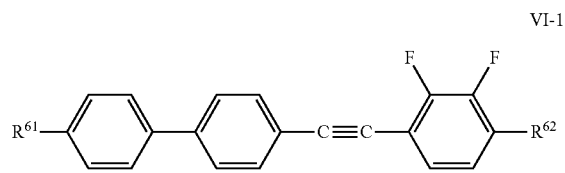

VI-1b in which

R$^{61}$ has the meaning indicated above and preferably denotes C$_n$H$_{2n+1}$ or CH$_2$=CH—(CH$_2$)$_z$, and R$^{62}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{61}$ and R$^{62}$) here are, in particular, (C$_n$H$_{2n+1}$ and C$_m$H$_{2m+1}$) and (C$_n$H$_{2n+1}$ and O—C$_m$H$_{2m+1}$), in the case of formula VI-1a particularly preferably (C$_n$H$_{2n+1}$ and C$_m$H$_{2m+1}$) and in the case of formula VI-1b particularly preferably (C$_n$H$_{2n+1}$ and O—C$_m$H$_{2m+1}$).

The compounds of the formula VI-3 are preferably compounds of the formula VI-3a:

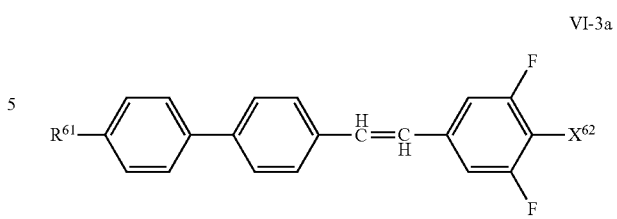

VI-3a in which the parameters have the meaning given above under formula VI-3 and preferably R$^{61}$ has the meaning indicated above and preferably denotes C$_n$H$_{2n+1}$, in which n denotes an integer in the range from 0 to 7, preferably in the range from 1 to 5, and X$^{62}$ denotes —F, —Cl, —OCF$_3$, —CN or —NCS, particularly preferably —NCS.

The compounds of the formula VI-4 are preferably compounds of the formula VI-4a:

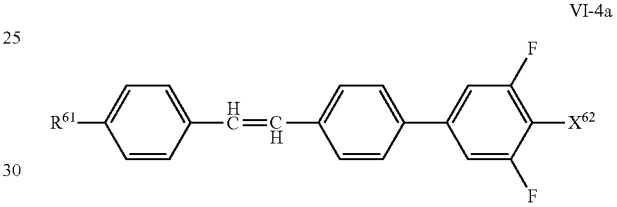

VI-4a in which the parameters have the meaning given above under formula VI-4 and preferably R$^{61}$ has the meaning indicated above and preferably denotes C$_n$H$_{2n+1}$, in which n denotes an integer in the range from 0 to 7, preferably in the range from 1 to 5, and X$^{62}$ denotes F, Cl, OCF$_3$, —CN or —NCS, particularly preferably —NCS.

Further preferred compounds of the formula VI are the compounds of the following formulae:

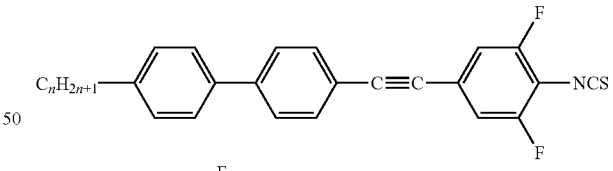

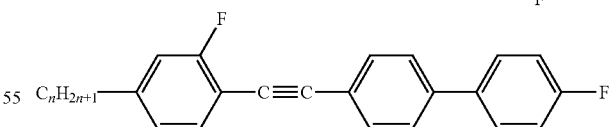

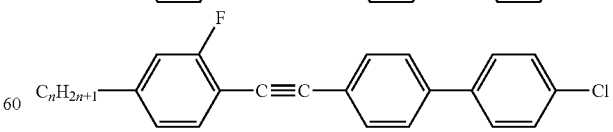

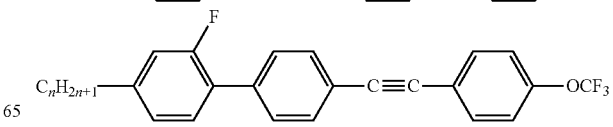

in which n denotes an integer in the range from 0 to 7, preferably in the range from 1 to 5.

The compounds of the formula VII are preferably selected from the group of the compounds of the formulae VII-1 to VII-6, more preferably these compounds of the formula VII predominantly consist, even more preferably essentially consist and very particularly preferably completely consist thereof:

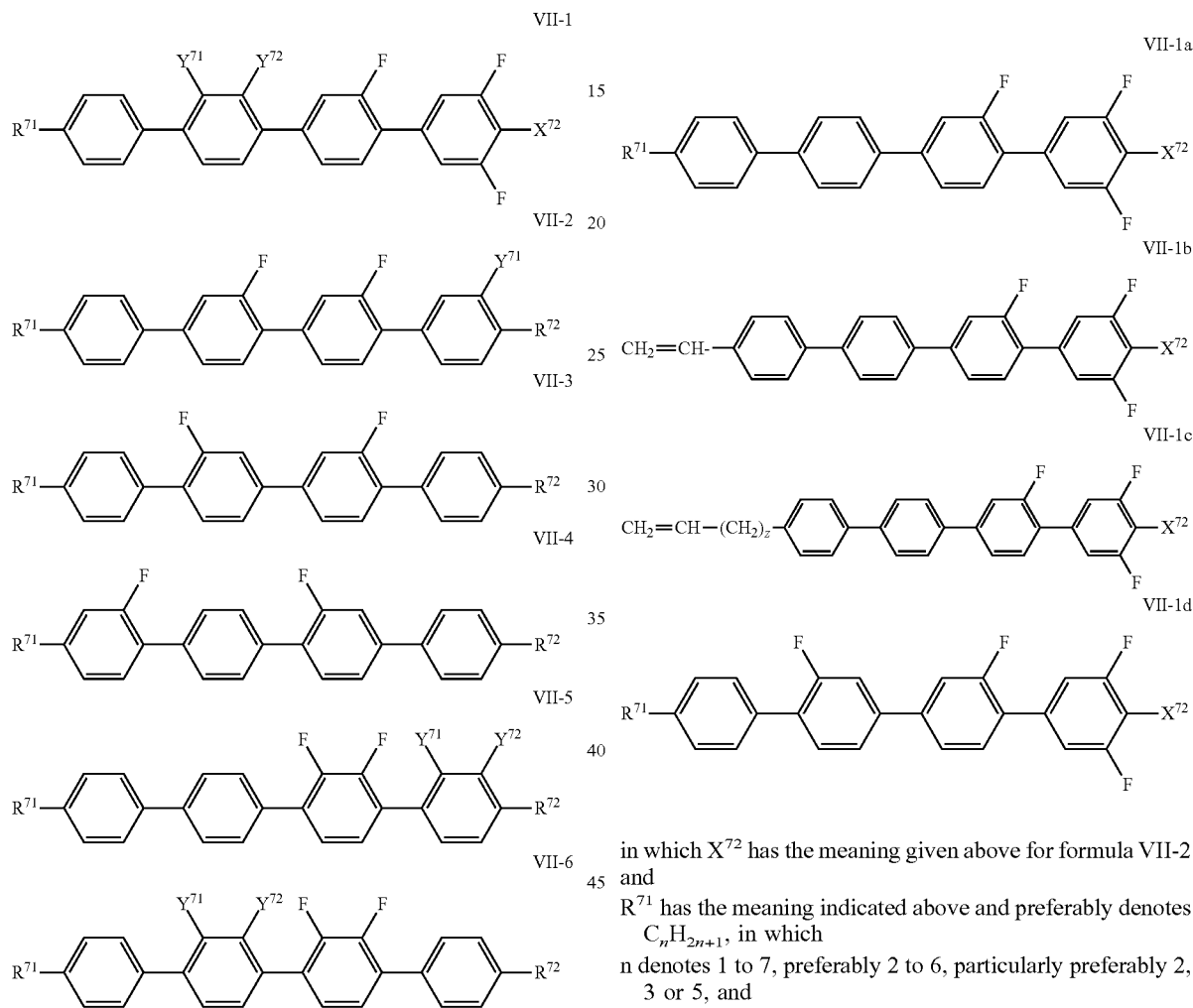

where the compounds of the formula VII-5 are excluded from the compounds of the formula VII-6, and
in which the parameters have the respective meanings indicated above for formula VII, and preferably
$R^{71}$ denotes unfluorinated alkyl or alkoxy, each having 1 to 7 C atoms, or unfluorinated alkenyl having 2 to 7 C atoms,
$R^{72}$ denotes unfluorinated alkyl or alkoxy, each having 1 to 7 C atoms, or unfluorinated alkenyl having 2 to 7 C atoms, and
$X^{72}$ denotes F, Cl or —$OCF_3$, preferably F, and particularly preferably
$R^{71}$ has the meaning indicated above and preferably denotes $C_nH_{2n+1}$ or $CH_2$=CH—$(CH_2)_Z$, and
$R^{72}$ has the meaning indicated above and preferably denotes $C_mH_{2m+1}$ or O—$C_mH_{2m+1}$ or $(CH_2)_Z$—CH=$CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The compounds of the formula VII-1 are preferably selected from the group of the compounds of the formulae VII-1a to VII-1d, more preferably these compounds of the formula VII-1 predominantly consist, even more preferably essentially consist and very particularly preferably completely consist thereof:

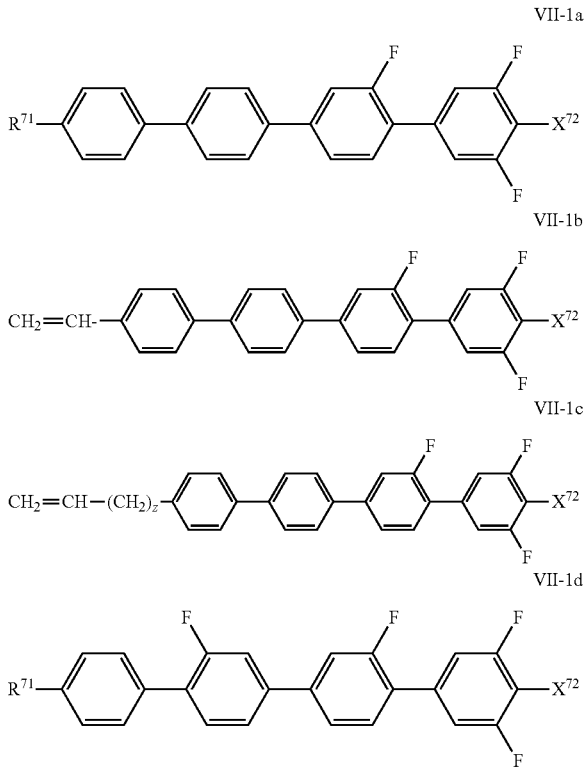

in which $X^{72}$ has the meaning given above for formula VII-2 and $R^{71}$ has the meaning indicated above and preferably denotes $C_nH_{2n+1}$, in which n denotes 1 to 7, preferably 2 to 6, particularly preferably 2, 3 or 5, and z denotes 0, 1, 2, 3 or 4, preferably 0 or 2, and $X^{72}$ preferably denotes F.

The compounds of the formula VII-2 are preferably selected from the group of the compounds of the formulae VII-2a and VII-2b, preferably of the formula VII-2a, more preferably these compounds of the formula VII-2 predominantly consist, even more preferably essentially consist and very particularly preferably completely consist thereof:

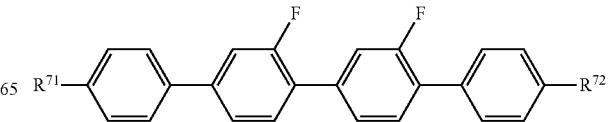

-continued

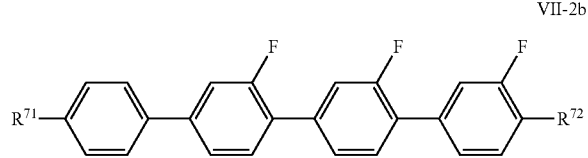
VII-2b in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VII-3 are preferably compounds of the formula VII-3a:

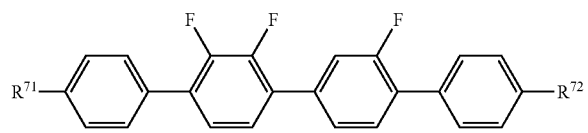
VII-3a in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VII-4 are preferably compounds of the formula VII-4a:

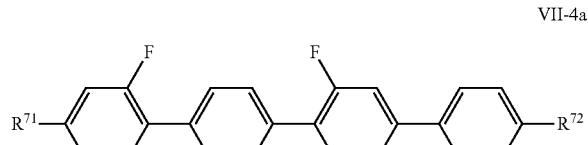
VII-4a in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VII-5 are preferably selected from the group of the compounds of the formulae VII-5a and VII-5b, preferably of the formula VII-5a, more preferably these compounds of the formula VII-5 predominantly consist, even more preferably essentially consist and very particularly preferably completely consist thereof:

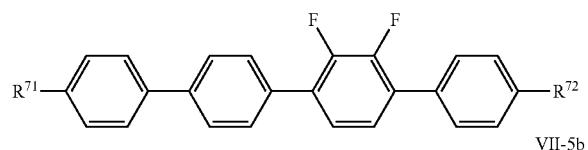
VII-5a

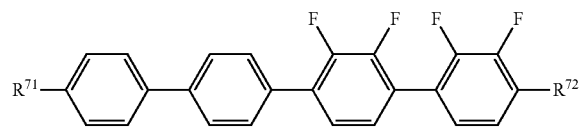
VII-5b in which
R$^{71}$ has the meaning indicated above and preferably denotes
  C$_n$H$_{2n+1}$ or CH$_2$=CH—(CH$_2$)$_z$, and
R$^{72}$ has the meaning indicated above and preferably denotes
  C$_m$H$_{2m+1}$ or O—C$_m$H$_{2m+1}$ or (CH$_2$)$_z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VII-6 are preferably selected from the group of the compounds of the formulae VII-6a and VII-6b, more preferably these compounds of the formula VII-6 predominantly consist, even more preferably essentially consist and very particularly preferably completely consist thereof:

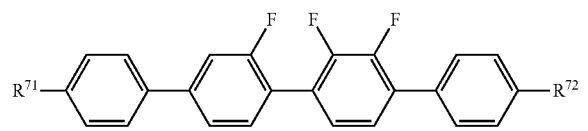
VII-6a

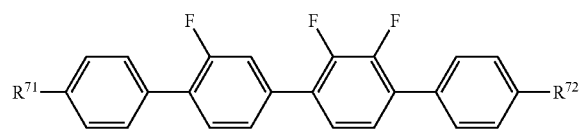
VII-6b in which
R$^{71}$ has the meaning indicated above and preferably denotes
 C$_n$H$_{2n+1}$ or CH$_2$=CH—(CH$_2$)$_Z$, and
R$^{72}$ has the meaning indicated above and preferably denotes
 C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{71}$ and R$^{72}$) here are, in particular, (CH$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The liquid-crystalline media in accordance with the present application preferably comprise in total 0 to 40%, preferably 0 to 30% and particularly preferably 5 to 25%, of compounds of the formula VIII.

The compounds of the formula VIII are preferably selected from the group of the compounds of the formulae VIII-1 to VIII-3, more preferably these compounds of the formula VIII predominantly consist, even more preferably essentially consist and very particularly preferably completely consist thereof:

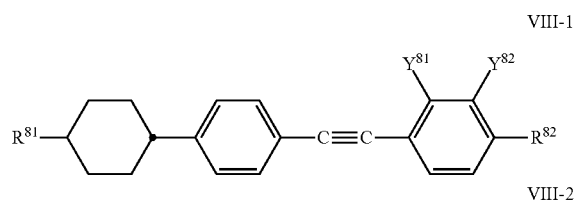

VIII-1

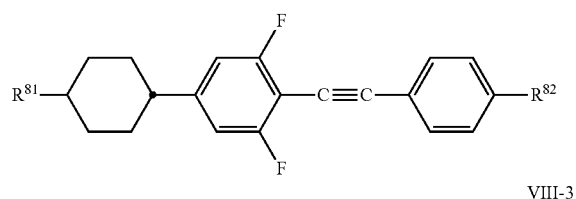

VIII-2

VIII-3 in which
one of
Y$^{81}$ and Y$^{82}$ denotes H and the other denotes H or F, and
R$^{81}$ has the meaning indicated above and preferably denotes
 C$_n$H$_{2n+1}$ or CH$_2$=CH—(CH$_2$)$_Z$, and
R$^{82}$ has the meaning indicated above and preferably denotes
 C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{81}$ and R$^{82}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VIII-1 are preferably selected from the group of the compounds of the formulae VIII-1a to VIII-1c, more preferably these compounds of the formula VIII-1 predominantly consist, even more preferably essentially consist and very particularly preferably completely consist thereof:

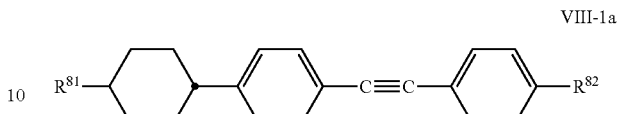

VIII-1a

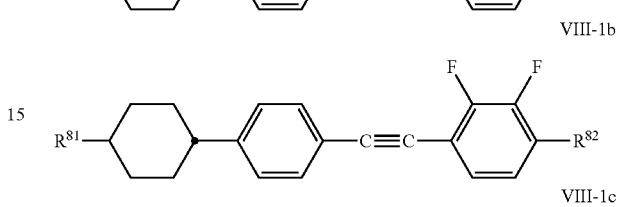

VIII-1b

VIII-1c

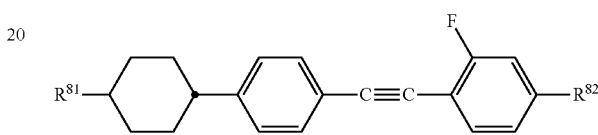

in which
R$^{81}$ has the meaning indicated above and preferably denotes
 C$_n$H$_{2n+1}$ or CH$_2$=CH—(CH$_2$)$_Z$, and
R$^{82}$ has the meaning indicated above and preferably denotes
 C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{81}$ and R$^{82}$) here are, in particular, (C$_n$H$_{2n+1}$ and C$_m$H$_{2m+1}$) and (C$_n$H$_{2n+1}$ and O—C$_m$H$_{2m+1}$), particularly preferably (C$_n$H$_{2n+1}$ and C$_m$H$_{2m+1}$).

The compounds of the formula VIII-2 are preferably compounds of the formula VIII-2a:

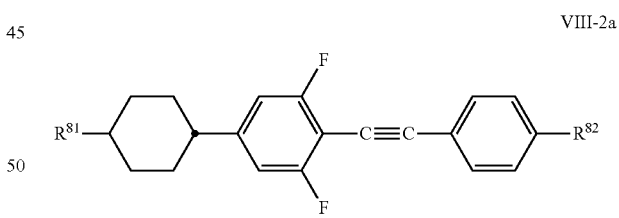

VIII-2a in which
R$^{81}$ has the meaning indicated above and preferably denotes
 C$_n$H$_{2n+1}$ or CH$_2$=CH—(CH$_2$)$_Z$, and
R$^{82}$ has the meaning indicated above and preferably denotes
 C$_m$H$_{2m+1}$ or O—C$_m$H$_{2m+1}$ or (CH$_2$)$_Z$—CH=CH$_2$, and in which
n and m, independently of one another, denote an integer in the range from 0 to 15, preferably in the range from 1 to 7 and particularly preferably 1 to 5, and
z denotes 0, 1, 2, 3 or 4, preferably 0 or 2.

The preferred combinations of (R$^{81}$ and R$^{82}$) here are, in particular, (C$_n$H$_{2n+1}$ and C$_m$H$_{2m+1}$), (C$_n$H$_{2n+1}$ and O—C$_m$H$_{2m+1}$) and (CH$_2$=CH—(CH$_2$)$_Z$ and C$_m$H$_{2m+1}$), particularly preferably (C$_n$H$_{2n+1}$ and C$_m$H$_{2m+1}$).

The compounds of the formula VIII-3 are preferably compounds of the formula VIII-3a:

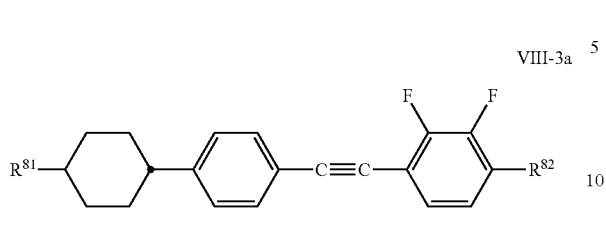

VIII-3a in which

R$^{81}$ has the meaning indicated above and preferably denotes C$_n$H$_{2n+1}$ or CH$_2$=CH—(CH$_2$)$_z$, and R$^{82}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{81}$ and R$^{82}$) here are, in particular, (C$_n$H$_{2n+1}$ and C$_m$H$_{2m+1}$) and (C$_n$H$_{2n+1}$ and O—C$_m$H$_{2m+1}$).

The compounds of the formula IX are preferably selected from the group of the compounds of the formulae IX-1 to IX-3, more preferably these compounds of the formula IX predominantly consist, even more preferably essentially consist and very particularly preferably completely consist thereof:

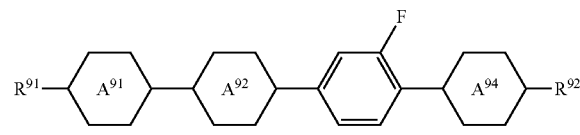

IX-1

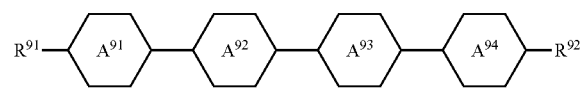

IX-2

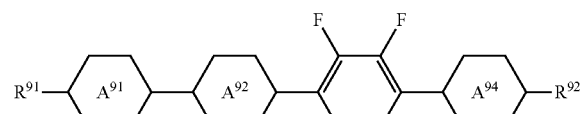

IX-3 in which the parameters have the respective meaning indicated above under formula IX and preferably one of

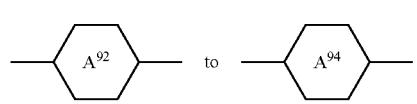

denotes

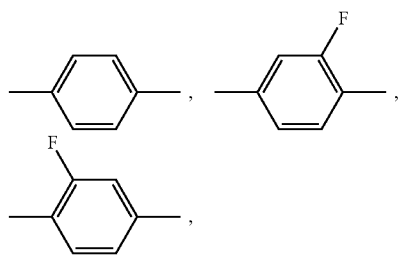

and
in which

R$^{91}$ has the meaning indicated above and preferably denotes C$_n$H$_{2n+1}$ or CH$_2$=CH—(CH$_2$)$_z$, and R$^{92}$ has the meaning indicated above and preferably denotes C$_m$H$_{2m+1}$ or O—C$_m$H$_{2m+1}$ or (CH$_2$)$_z$—CH=CH$_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of (R$^{91}$ and R$^{92}$) here are, in particular, (CH$_{2n+1}$ and C$_m$H$_{2m+1}$) and (C$_n$H$_{2n+1}$ and O—C$_m$H$_{2m+1}$).

The liquid-crystalline media in accordance with the present application preferably comprise in total 5 to 30%, preferably 10 to 25% and particularly preferably 15 to 20%, of compounds of the formula IX.

The compounds of the formula IX-1 are preferably selected from the group of the compounds of the formulae IX-1a to IX-1e, more preferably these compounds of the formula IX-1 predominantly consist, even more preferably essentially consist and very particularly preferably completely consist thereof:

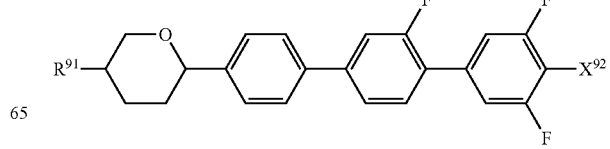

-continued

IX-1e

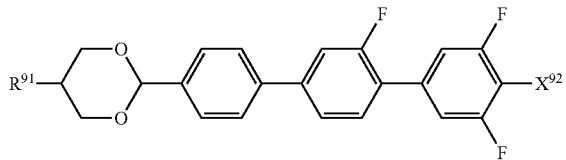

in which the parameters have the meaning given above and preferably $R^{91}$ has the meaning indicated above and preferably denotes $C_nH_{2n+1}$, and n denotes an integer in the range from 0 to 15, preferably in the range from 1 to 7 and particularly preferably 1 to 5, and $X^{92}$ preferably denotes F or Cl.

The compounds of the formula IX-2 are preferably selected from the group of the compounds of the formulae IX-2a and IX-2b, more preferably these compounds of the formula IX-2 predominantly consist, even more preferably essentially consist and very particularly preferably completely consist thereof:

IX-2a

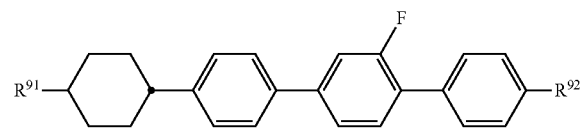

IX-2b

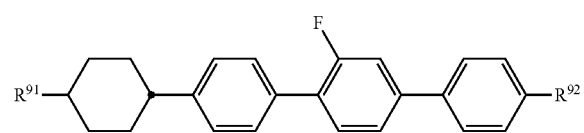

in which $R^{91}$ has the meaning indicated above and preferably denotes $C_nH_{2n+1}$ or $CH_2=CH-(CH_2)_Z$, and $R^{92}$ has the meaning indicated above and preferably denotes $C_mH_{2m+1}$ or $O-C_mH_{2m+1}$ or $(CH_2)_Z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combination of ($R^{91}$ and $R^{92}$) here is, in particular, ($C_nH_{2n+1}$ and $C_mH_{2m+1}$).

The compounds of the formula IX-3 are preferably compounds of the formulae IX-3a and IX-3b:

IX-3a

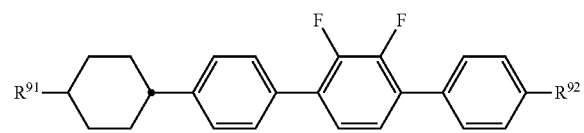

IX-3b

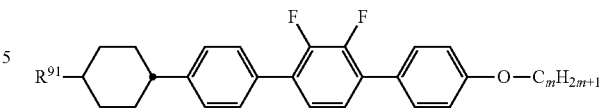

in which $R^{91}$ has the meaning indicated above and preferably denotes $C_nH_{2n+1}$ or $CH_2=CH-(CH_2)_Z$, and $R^{92}$ has the meaning indicated above and preferably denotes $C_mH_{2m+1}$ or $O-C_mH_{2m+1}$ or $(CH_2)_Z-CH=CH_2$, and in which n and m, independently of one another, denote an integer in the range from 0 to 15, preferably in the range from 1 to 7 and particularly preferably 1 to 5, and z denotes 0, 1, 2, 3 or 4, preferably 0 or 2.

The preferred combinations of ($R^{91}$ and $R^{92}$) here are, in particular, ($CH_{2n+1}$ and $C_mH_{2m+1}$) and ($C_nH_{2n+1}$ and $O-C_mH_{2m+1}$), particularly preferably ($C_nH_{2n+1}$ and $O-C_mH_{2m+1}$).

In a preferred embodiment of the present invention, the medium comprises one or more dielectrically positive compounds of the formula V-1 having a dielectric anisotropy of greater than 3.

The liquid-crystalline media in accordance with the present invention preferably comprise 10% or less, preferably 5% or less, particularly preferably 2% or less, very particularly preferably 1% or less, and in particular absolutely no compound having only two or fewer five- and/or six-membered rings.

In a preferred embodiment of the present invention, the medium comprises one or more compounds of the formula VI.

In a further preferred embodiment of the present invention, the medium comprises one or more compounds of the formula VII.

The definitions of the abbreviations (acronyms) used for the compounds in the present application are indicated below in Table E or are evident from Tables A to C.

In a preferred embodiment of the present invention, the liquid-crystal medium, or component A of the liquid-crystal medium, comprises one or more compounds of the formulae I-1 and/or I-2 and/or I-3 and/or I-4.

The liquid-crystal medium, or component A of the liquid-crystal medium, preferably comprises one or more compounds selected from the compounds of the formulae I-1a-1 to I-1a-12, particularly preferably of the formula I-1a-2, very particularly preferably one or more compounds of the formula I-1a-2 and one or more compounds selected from the group of the compounds of the formula I-1a-1 and formulae I-1a-3 to I-1a-12, and one or more compounds of the formulae I-1b-1 to I-1b-12 and/or I-2 and/or I-3 and/or I-4.

In a further preferred embodiment of the present invention, the liquid-crystal medium, or component A of the liquid-crystal medium, comprises one or more compounds selected from the group of the compounds of the formulae I-1b-1 to I-1b-12, particularly preferably selected from the group of the compounds of the formulae I-1b-5 and/or I-1b-7 and/or I-1b-8 and/or I-1b-9 and/or I-1b-10, and one or more compounds selected from the group of the compounds of the formulae I-1a-1 to I-1a-12, preferably of the formula I-1a-2, and/or one or more compounds of the formulae I-2 and/or I-3 and/or I-4.

In a further preferred embodiment of the present invention, the liquid-crystal medium, or component A of the liquid-crystal medium, comprises one or more compounds of the formula I-2 and one or more compounds of the formula I-1, preferably of the formula I-1a, preferably of the formulae I-1a-2, and/or I-1b, and/or one or more compounds of the formulae I-3 and/or I-4.

In a further preferred embodiment of the present invention, the liquid-crystal medium, or component A of the liquid-crystal medium, comprises one or more compounds of the formula I-3 and one or more compounds of the formula I-1, preferably of the formula I-1a, preferably of the formula I-1a-2, and/or I-1b, and/or one or more compounds of the formulae I-2 and/or I-4.

In a further preferred embodiment of the present invention, the liquid-crystal medium, or component A of the liquid-crystal medium, comprises one or more compounds of the formula I-4 and one or more compounds of the formula I-1, preferably of the formula I-1a, preferably of the formula I-1a-2, and/or I-1b, and/or one or more compounds of the formulae I-2 and/or I-3.

The liquid-crystalline media in accordance with the present invention preferably comprise, more preferably predominantly consist of, even more preferably essentially consist of and very particularly preferably completely consist of compounds selected from the group of the compounds of the formulae I, II, IV and V, preferably I, II and IV, or selected from the group of the compounds of the formulae I, III, IV and V, preferably I, III and IV.

In this application, comprise in connection with compositions means that the entity in question, i.e. the medium or the component, comprises the component or components or compound or compounds indicated, preferably in a total concentration of 10% or more and very preferably 20% or more.

In this connection, predominantly consist of means that the entity in question comprises 55% or more, preferably 60% or more and very preferably 70% or more, of the component or components or compound or compounds indicated.

In this connection, essentially consist of means that the entity in question comprises 80% or more, preferably 90% or more and very preferably 95% or more, of the component or components or compound or compounds indicated.

In this connection, completely consist of means that the entity in question comprises 98% or more, preferably 99% or more and very preferably 100.0% of the component or components or compound or compounds indicated.

Other mesogenic compounds which are not explicitly mentioned above can optionally and advantageously also be used in the media in accordance with the present invention. Such compounds are known to the person skilled in the art.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The nematic phase of the media according to the invention preferably extends at least from 20° C. or less to 90° C. or more, preferably up to 100° C. or more, more preferably at least from 0° C. or less to 120° C. or more, very preferably at least from −10° C. or less to 140° C. or more and in particular at least from −20° C. or less to 150° C. or more.

The $\Delta\epsilon$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm (Na$^D$) and 20° C., is preferably in the range from 0.200 or more to 0.90 or less, more preferably in the range from 0.250 or more to 0.90 or less, even more preferably in the range from 0.300 or more to 0.85 or less and very particularly preferably in the range from 0.350 or more to 0.800 or less.

In a preferred embodiment of the present application, the $\Delta n$ of the liquid-crystal media in accordance with the present invention is preferably 0.40 or more, more preferably 0.45 or more.

In accordance with the present invention, the individual compounds of the formula I in the liquid-crystal media are preferably used in a total concentration of 10% to 100%, more preferably 30% to 95%, even more preferably 40% to 90% and very preferably 50% to 90%, of the mixture as a whole.

In the embodiment of the present invention in which the liquid-crystal media comprise one or more compounds selected from the group of the compounds of the formulae IIA and IIB, the further compounds are preferably employed as follows.

The compounds selected from the group of the compounds of the formulae IIA and IIB are preferably used in a total concentration of 1% to 30%, more preferably 2% to 20%, even more preferably 3% to 18% and very preferably 4% to 16%, of the mixture as a whole.

The compounds of the formula IV are preferably used in a total concentration of 1% to 20%, more preferably 2% to 15%, even more preferably 3% to 12% and very preferably 5% to 10%, of the mixture as a whole.

The liquid-crystal media preferably comprise, more preferably predominantly consist of and very preferably completely consist of in total 70% to 100%, more preferably 80% to 100% and very preferably 90% to 100% and in particular 95% to 100%, of the compounds of the formulae I, IIA, IIB and IV to IX, preferably of the formulae I, IIA, IIB and IV.

In the embodiment of the present invention in which the liquid-crystal media comprise one or more compounds selected from the group of the compounds of the formulae IIIA and IIIB, the further compounds are preferably employed as follows.

The compounds selected from the group of the compounds of the formulae IIIA and IIIB are preferably used in a total concentration of 1% to 60%, more preferably 5% to 55%, even more preferably 7% to 50% and very preferably 10% to 45%, of the mixture as a whole.

If the liquid-crystal media comprise only one or more compounds of the formula IIIA, but no compounds of the formula IIIB, the compounds of the formula IIIA are preferably used in a total concentration of 10% to 60%, more preferably 20% to 55%, even more preferably 30% to 50% and very preferably 35% to 45%, of the mixture as a whole.

If the liquid-crystal media comprise only one or more compounds of the formula IIIB, but no compounds of the formula IIIA, the compounds of the formula IIIB are preferably used in a total concentration of 5% to 45%, more preferably 10% to 40%, even more preferably 15% to 35% and very preferably 20% to 30%, of the mixture as a whole.

If the liquid-crystal media comprise both one or more compounds of the formula IIIA and one or more compounds of the formula IIIB, the compounds of the formula IIIA are preferably used in a total concentration of 5% to 50%, more preferably 10% to 45%, even more preferably 15% to 30% and very preferably 20% to 25%, of the mixture as a whole and the compounds of the formula IIIB are preferably used in a total concentration of 1% to 35%, more preferably 5% to 30%, even more preferably 7% to 25% and very preferably 10% to 20%, of the mixture as a whole.

The compounds of the formula IV are preferably used in a total concentration of 1% to 20%, more preferably 2% to 15%, even more preferably 3% to 12% and very preferably 5% to 10%, of the mixture as a whole.

The liquid-crystal media preferably comprise, more preferably predominantly consist of and very preferably completely consist of in total 70% to 100%, more preferably 80% to 100% and very preferably 90% to 100% and in particular 95% to 100%, of the compounds of the formulae I, IIIA, IIIB and IV to IX, preferably of the formulae I, IIIA and/or IIIB and/or [lacuna].

In a particularly preferred embodiment of the present invention, the liquid-crystalline media comprise one or more compounds of the formula V and one or more compounds of the formula VI.

In a further particularly preferred embodiment of the present invention, the liquid-crystalline media comprise one or more compounds of the formula V and one or more compounds of the formula VII.

The liquid-crystalline media in accordance with the present invention likewise preferably comprise one or more compounds of the formula V, one or more compounds of the formula VI and one or more compounds of the formula VIII.

If the liquid-crystalline media in accordance with the present application comprise one or more compounds of the formula V, the concentration of these compounds is preferably in total 10 to 30%, preferably 15 to 25% and particularly preferably 18 to 22%.

If the liquid-crystalline media in accordance with the present application comprise one or more compounds of the formula VI, the concentration of these compounds is preferably in total 15 to 35%, preferably 18 to 30% and particularly preferably 22 to 26%.

If the liquid-crystalline media in accordance with the present application comprise one or more compounds of the formula VII, the concentration of these compounds is preferably in total 4 to 25%, preferably 8 to 20% and particularly preferably 10 to 14%.

If the liquid-crystalline media in accordance with the present application comprise one or more compounds of the formula VIII, the concentration of these compounds is preferably in total 15 to 35%, preferably 18 to 30% and particularly preferably 22 to 26%.

If the liquid-crystalline media in accordance with the present application comprise one or more compounds of the formula IX, the concentration of these compounds is preferably in total 5 to 25%, preferably 10 to 20% and particularly preferably 13 to 17%.

In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. $\Delta\epsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

The following definitions apply here.

$$\Delta\epsilon \equiv (\epsilon_\parallel - \epsilon_\perp) \text{ and}$$

$$\epsilon_{average} \equiv (\epsilon_\parallel + 2\epsilon_\perp)/3.$$

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\epsilon_\parallel$) and polyimide AL-1054 from Japan Synthetic Rubber, Japan, for homogeneous orientation ($\epsilon_\perp$). The capacitances are determined using a Solatron 1260 frequency response analyser using a sine wave with a voltage of 0.3 $V_{rms}$.

The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency region as described in A. Penirschke et al., "Cavity Perturbation Method for Characterisation of Liquid Crystals up to 35 GHz", 34$^{th}$ European Microwave Conference—Amsterdam, pp. 545-548. Compare in this respect also A. Gaebler et al., "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a cylindrical polytetrafluoroethylene (PTFE) or quartz capillary. The capillary has an internal radius of 180 μm and an external radius of 350 μm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the result of the output signal is recorded using a commercial vector network analyser. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 of the above-mentioned publication A. Penirschke et al., "Cavity Perturbation Method for Characterisation of Liquid Crystals up to 35 GHz", 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 160° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a layer thickness of 5 μm for at least 100 hours. At high temperatures, the clearing point is measured in capillaries by conventional methods.

Furthermore, the liquid-crystal media according to the invention are characterised by high optical anisotropies in the visible region. The birefringence at 589 nm is preferably 0.20 or more, particularly preferably 0.25 or more, particularly preferably 0.30 or more, particularly preferably 0.40 or more and very particularly preferably 0.45 or more. In addition, the birefringence is preferably 0.80 or less.

In a preferred embodiment of the present invention, the liquid-crystal media employed have positive dielectric anisotropy (Δ∈). This is preferably 1.8 or more and 15.0 or less, more preferably between 2.0 or more and 10.0 or less, particularly preferably between 3.0 or more and 8.0 or less and very particularly preferably between 3.5 or more and 6.0 or less.

If the liquid-crystal media employed have negative dielectric anisotropy (Δ∈), this is preferably less than or equal to −2.5, particularly preferably less than or equal to −4.0 and very particularly preferably less than or equal to −5.0.

In this preferred embodiment of the present invention, in which the liquid-crystal media employed have negative dielectric anisotropy (Δ∈), the value thereof is preferably between 1.5 or more and 15.0 or less, particularly preferably between 1.8 or more and 12.0 or less and very particularly preferably between 2.0 or more and 10.0 or less.

Furthermore, the liquid-crystal media according to the invention are characterised by high anisotropies in the microwave region and/or millimeter wave region. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The dielectric anisotropy in the microwave region is defined as $$\Delta\epsilon_r \equiv (\epsilon_{r,\parallel} - \epsilon_{r,\perp}).$$

The tuneability (τ) is defined as $$\tau \equiv (\Delta\epsilon_r / \epsilon_{r,\parallel}).$$

The material quality (η) is defined as $$\eta \equiv (\tau / \tan \delta_{\epsilon_r,max.}), \text{ where}$$

the maximum dielectric loss is $$\tan \delta_{\epsilon_r,max.} \equiv \max.\{\tan \delta_{\epsilon_r,\perp}; \tan \delta_{\epsilon_r,\parallel}\}.$$

The material quality (η) of the preferred liquid-crystal materials is 6 or more, preferably 8 or more, preferably 10 or more, preferably 15 or more, preferably 17 or more, preferably 20 or more, particularly preferably 25 or more, very particularly preferably 30 and in particular 40 or more or even 50 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, it is also possible to use liquid crystals having a negative value of the dielectric anisotropy.

The liquid crystals employed are either individual substances or mixtures. They preferably have a nematic phase.

The term "alkyl" preferably encompasses straight-chain and branched alkyl groups, as well as cycloalkyl groups, each having 1 to 15 carbon atoms, in particular the straight-chain groups methyl, ethyl, propyl, butyl, pentyl, hexyl and heptyl, as well as cyclopropyl and cyclohexyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluoro-butyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote an integer from 1 to 10. Preferably, n here is 1 and m is 1 to 6.

Compounds containing a vinyl end group and compounds containing a methyl end group have low rotational viscosity.

In the present application, both high-frequency technology and hyper-frequency technology denote applications having frequencies in the range from 1 MHz to 100 THz, preferably from 1 GHz to 30 THz, more preferably 2 GHz to 10 THz, particularly preferably from about 5 GHz to 5 THz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

The liquid-crystal media according to the invention consist of a plurality of compounds, preferably 3 to 30, more preferably 4 to 20 and very preferably 4 to 15 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, having n, m and l C atoms respectively, where n, m and l, independently of one another, denote an integer from 1 to 9, preferably 1 to 7, or from 2 to 9, preferably 2 to 7, respectively. $C_oH_{2o+1}$ denotes straight-chain alkyl having 1 to 7, preferably 1 to 4, C atoms, or branched alkyl having 1 to 7, preferably 1 to 4, C atoms.

Table A lists the codes used for the ring elements of the core structures of the compounds, while Table C shows the linking groups. Table C gives the meanings of the codes for the left-hand or right-hand end groups. Table D shows illustrative structures of compounds with their respective abbreviations.

TABLE A

| Ring elements | | | |
|---|---|---|---|
| C |  | P | 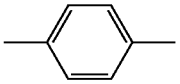 |
| D | 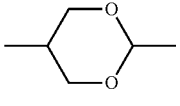 | DI | 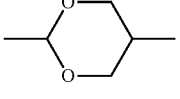 |
| A | 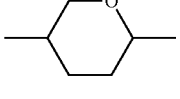 | AI | 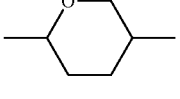 |
| G | 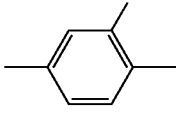 | GI | 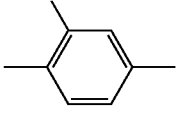 |
| U | 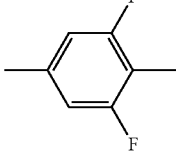 | UI | 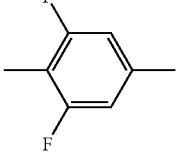 |

TABLE A-continued
Ring elements
| | | | |
|---|---|---|---|
| Y | 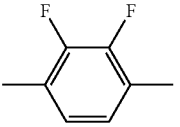 | | |
| fX | 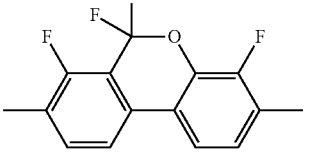 | fXI | 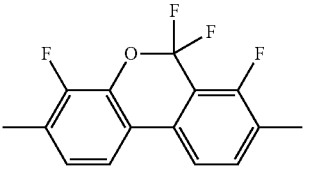 |
| M | 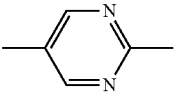 | MI | 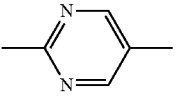 |
| N | 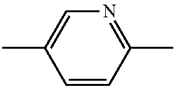 | NI | 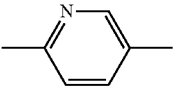 |
| fN | 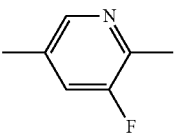 | fNI | 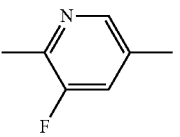 |
| dH | 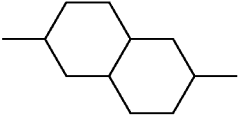 | N(2,6) | 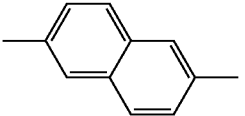 |
| N(1,4) | 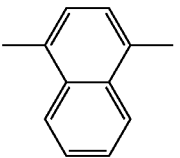 | | |
| N3f | 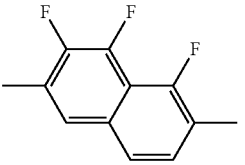 | N3fI | 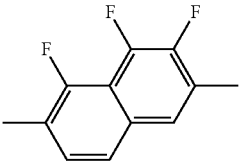 |
| tH | 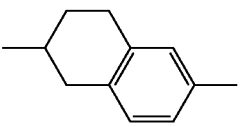 | tHI | 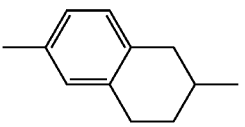 |
| tH2f | 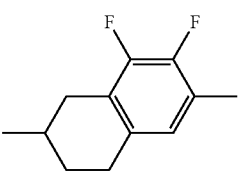 | tH2fI | 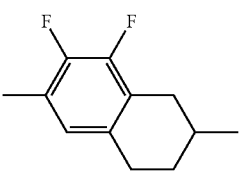 |

TABLE A-continued

| Ring elements | | | |
|---|---|---|---|
| K | (structure) | KI | (structure) |
| L | (structure) | LI | (structure) |
| F | (structure) | FI | (structure) |
| P(o) | $C_oH_{2o+1}$ (structure) | PI(o) | $C_oH_{2o+1}$ (structure) |
| P(i3) | (structure) | PI(c3) | (structure) |
| P(t4) | (structure) | PI(t4) | (structure) |
| P(c3) | (structure) | PI(c3) | (structure) |
| P(c4) | (structure) | PI(c4) | (structure) |
| P(c5) | (structure) | PI(c5) | (structure) |

TABLE A-continued
| Ring elements | | | |
|---|---|---|---|
| P(e5) | 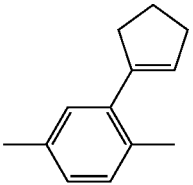 | PI(e5) | 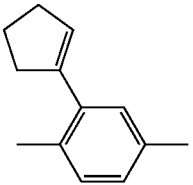 |
| P(c6) | 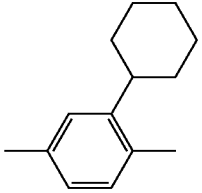 | PI(c6) | 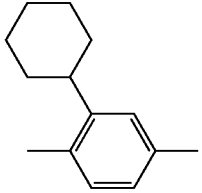 |
| P(e6) | 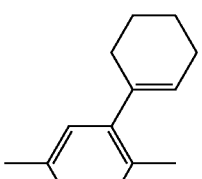 | PI(e6) | 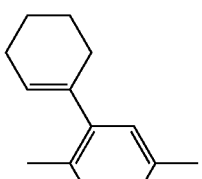 |
| GI(o) | 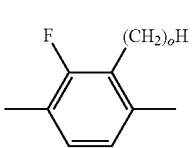<br>o ∈ {1; 2; 3; 4; 5; 6} | G(o) | 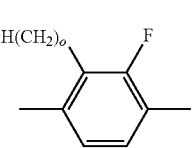<br>o ∈ {1; 2; 3; 4; 5; 6} |
| GI(i3) | 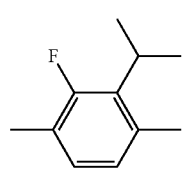 | G(i3) | 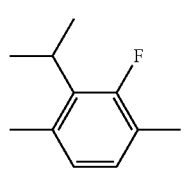 |
| GI(t4) | 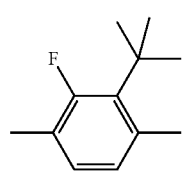 | G(t4) | 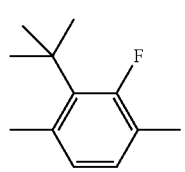 |
| GI(c3) | 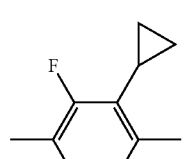 | G(c3) | 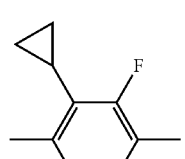 |
| GI(c4) | 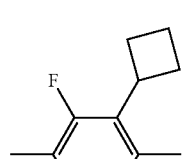 | G(c4) | 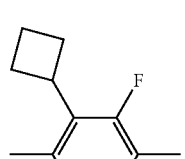 |

TABLE A-continued

Ring elements

GI(c5): 2-fluoro-3,6-disubstituted phenyl with cyclopentyl group  
G(c5): 3-fluoro-2,5-disubstituted phenyl with cyclopentyl group GI(e5): 2-fluoro-3,6-disubstituted phenyl with cyclopentenyl group  
G(e5): 3-fluoro-2,5-disubstituted phenyl with cyclopentenyl group GI(c6): 2-fluoro-3,6-disubstituted phenyl with cyclohexyl group  
G(c6): 3-fluoro-2,5-disubstituted phenyl with cyclohexyl group GI(e6): 2-fluoro-3,6-disubstituted phenyl with cyclohexenyl group  
G(e6): 3-fluoro-2,5-disubstituted phenyl with cyclohexenyl group

TABLE B

Linking groups

| | | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CF$_2$CF$_2$— | | |

TABLE C

End groups

| Left-hand side | | Right-hand side | |
|---|---|---|---|
| Use alone | | | |
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n+1}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -OXF- | CF$_2$=CH—O— | -OXF | —O—CH=CF$_2$ |
| -A- | H—C≡C— | -A | —C≡C—H |

TABLE C-continued

| End groups | | | |
|---|---|---|---|
| Left-hand side | | Right-hand side | |
| -nA- | $C_nH_{2n+1}$—C≡C— | -An | —C≡C—$C_nH_{2n+1}$ |
| -NA- | N≡C—C≡C— | -AN | —C≡C—C≡N |
| Use together with others | | | |
| -...A...- | —C≡C— | -...A... | —C≡C— |
| -...V...- | CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots " . . . " are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

The illustrative structures show compounds which are particularly preferably employed.

Examples of compounds of component A

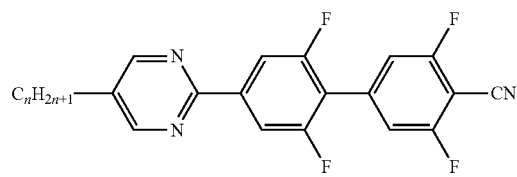

MUU-n-N

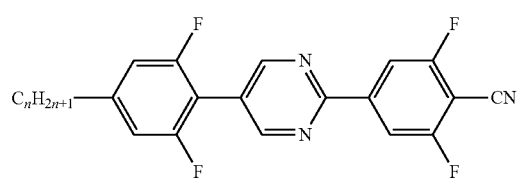

UMU-n-N

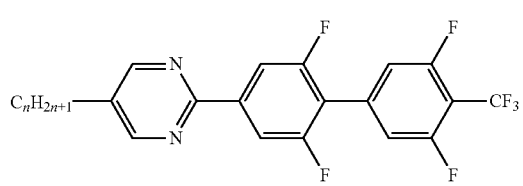

MUU-n-T

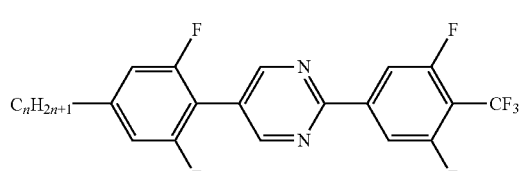

UMU-n-T

TABLE D-continued
Illustrative structures
Examples of compounds of component B
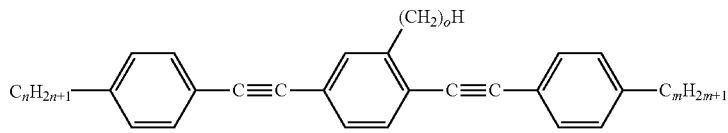
PTP(o)TP-n-m, o ∈ {1; 2; 3; 4; 5; 6}
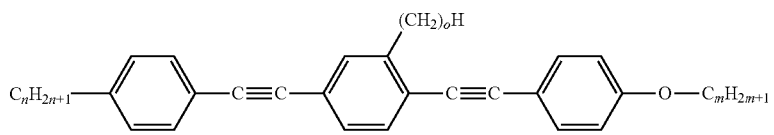
PTP(o)TP-n-Om, o ∈ {1; 2; 3; 4; 5; 6}
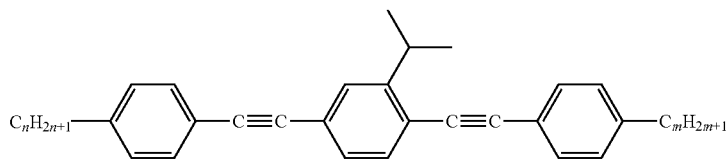
PTP(i3)TP-n-m
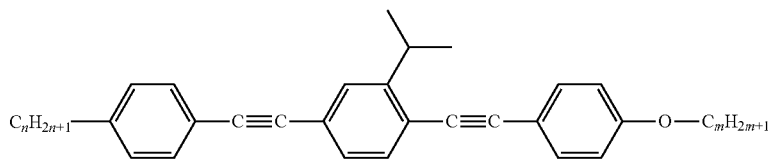
PTP(i3)TP-n-Om
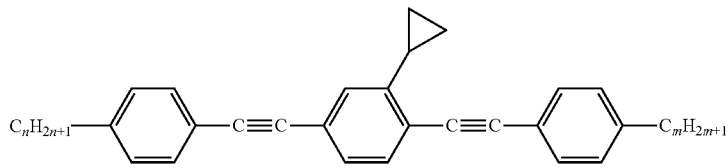
PTP(c3)TP-n-m
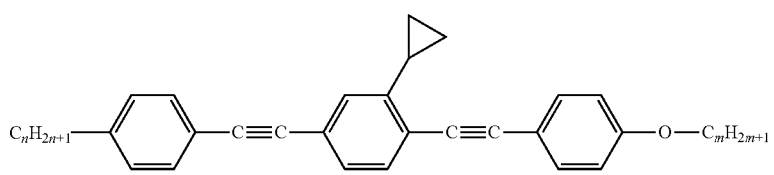
PTP(c3)TP-n-Om
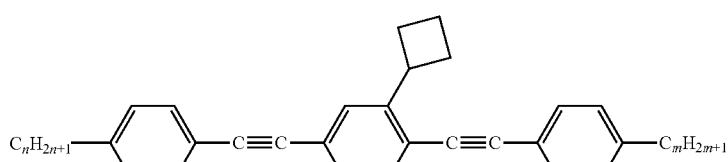
PTP(c4)TP-n-m TABLE D-continued
Illustrative structures
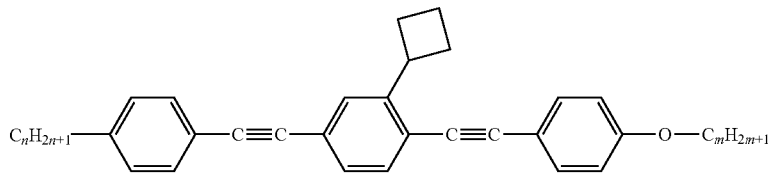
PTP(c4)TP-n-Om
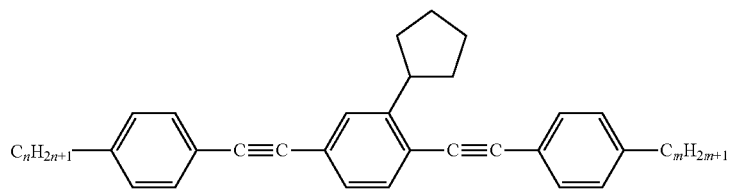
PTP(c5)TP-n-m
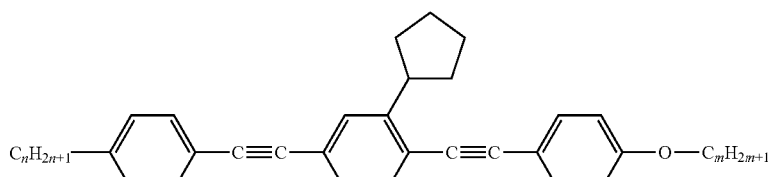
PTP(c5)TP-n-Om
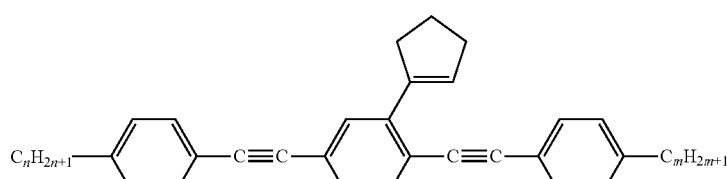
PTP(e5)TP-n-m
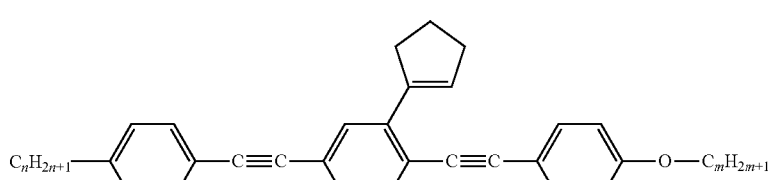
PTP(e5)TP-n-Om
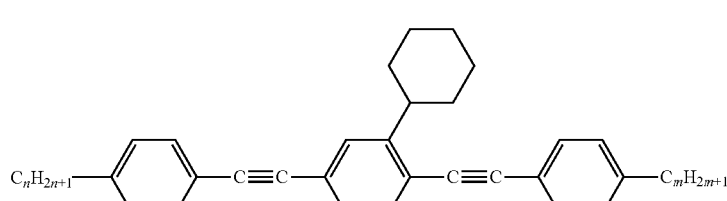
PTP(c6)TP-n-m TABLE D-continued
Illustrative structures
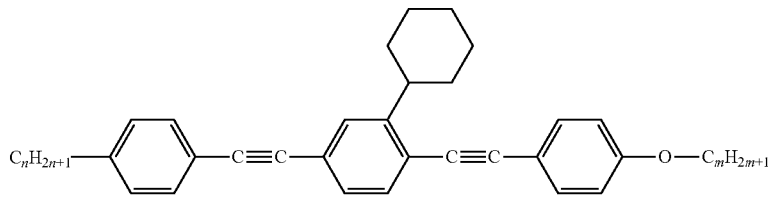
PTP(c6)TP-n-Om
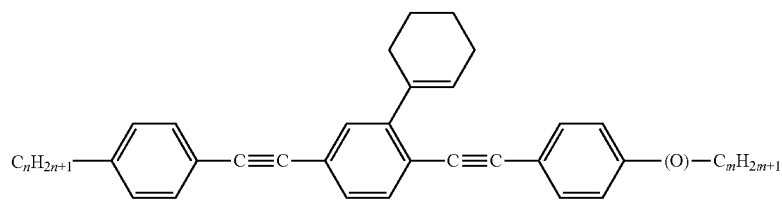
PTP(e6)TP-n-(O)m
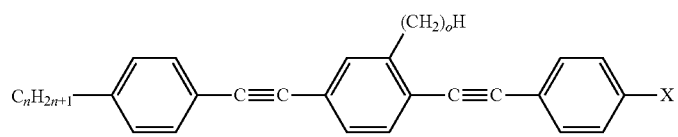
PTP(o)TP-n-X, X = F, Cl, o ∈ {1; 2; 3; 4; 5; 6}
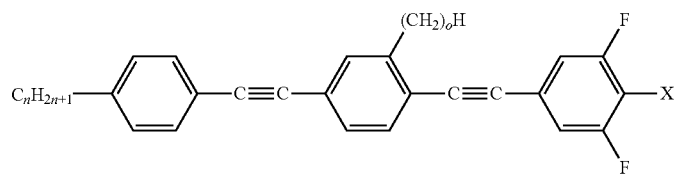
PTP(o)TU-n-X, X = F, Cl, o ∈ {1; 2; 3; 4; 5; 6}
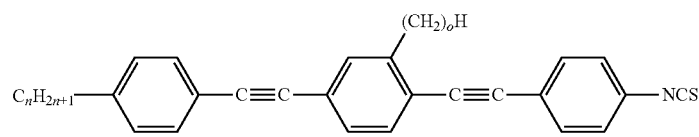
PTP(o)TP-n-S o ∈ {1; 2; 3; 4; 5; 6}
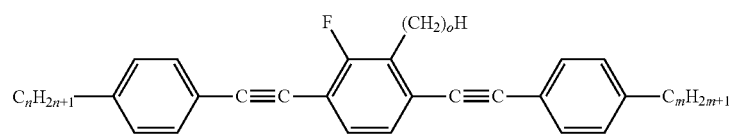
PTGI(o)TP-n-m, o ∈ {1; 2; 3; 4; 5; 6}
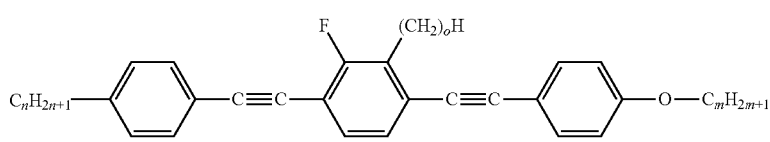
PTGI(o)TP-n-Om, o ∈ {1; 2; 3; 4; 5; 6}

TABLE D-continued
Illustrative structures
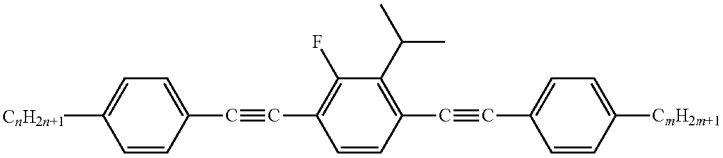
PTGI(i3)TP-n-m
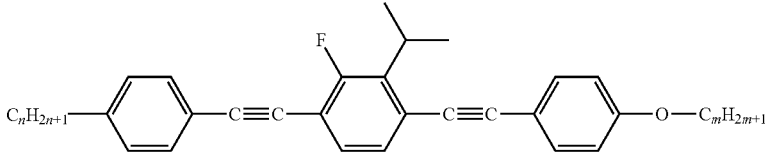
PTGI(i3)TP-n-Om
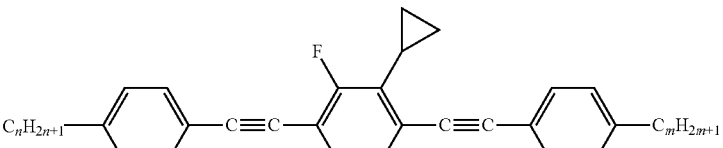
PTGI(c3)TP-n-m
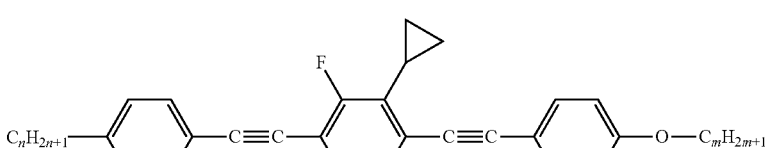
PTGI(c3)TP-n-Om
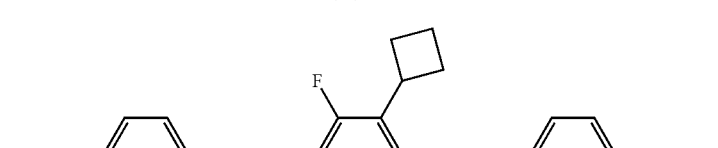
PTGI(c4)TP-n-m
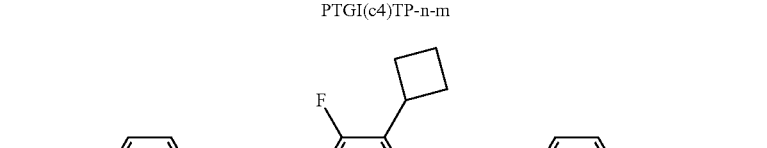
PTGI(c4)TP-n-Om
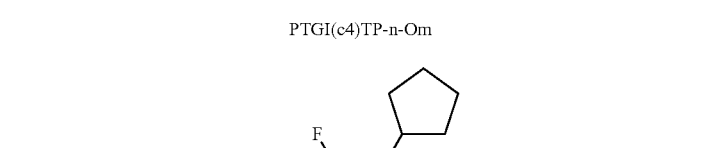
PTGI(c5)TP-n-m TABLE D-continued
Illustrative structures
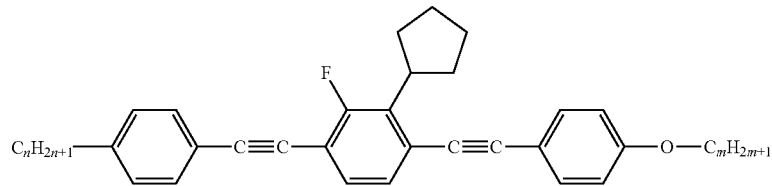
PTGI(c5)TP-n-Om
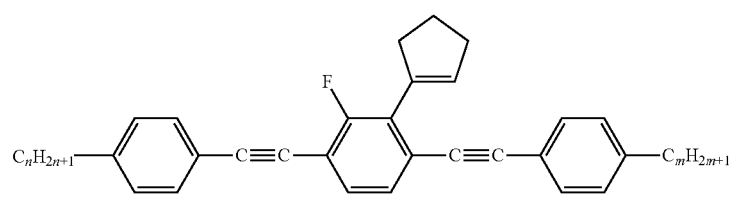
PTGI(e5)TP-n-m
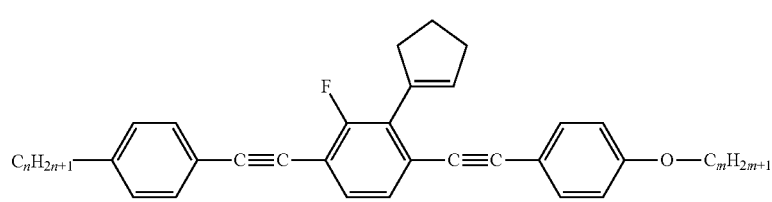
PTGI(e5)TP-n-Om
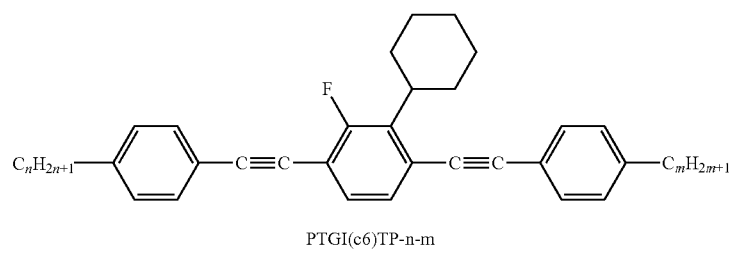
PTGI(c6)TP-n-m
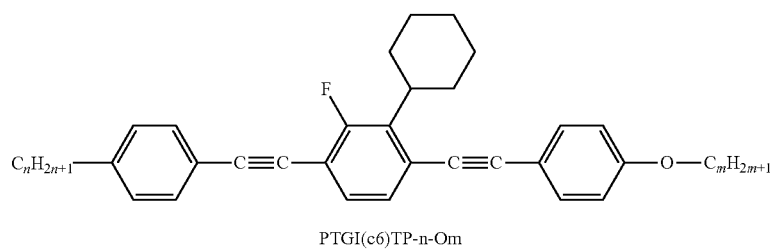
PTGI(c6)TP-n-Om
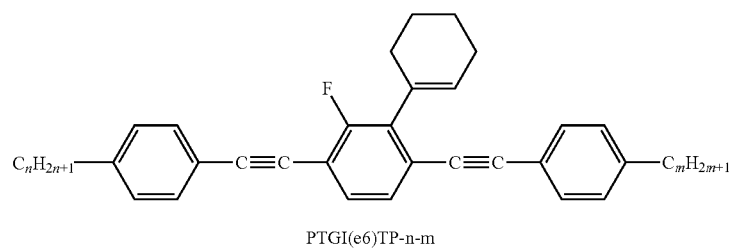
PTGI(e6)TP-n-m TABLE D-continued
Illustrative structures
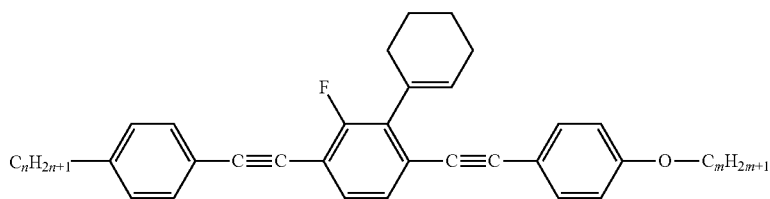
PTGI(e6)TP-n-Om
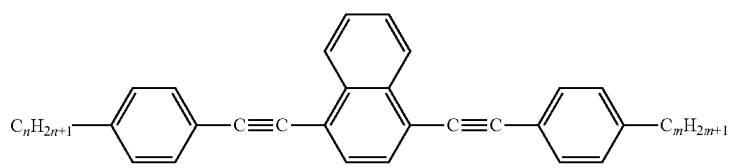
PTN(1,4)TP-n-m
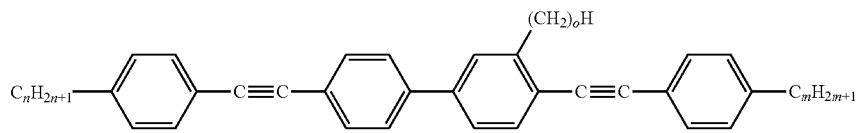
PTPP(o)TP-n-m, o ∈ {1; 2; 3; 4; 5; 6}
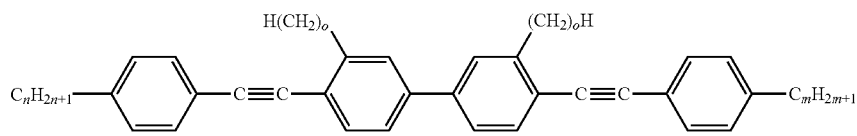
PTPI(o)P(o)TP-n-m, o ∈ {1; 2; 3; 4; 5; 6}
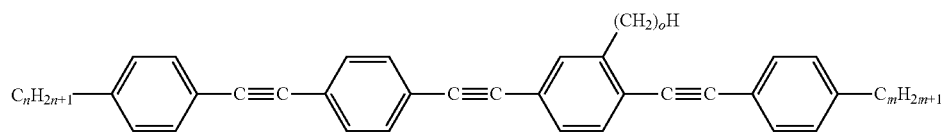
PTPTP(o)P-n-m, o ∈ {1; 2; 3; 4; 5; 6}
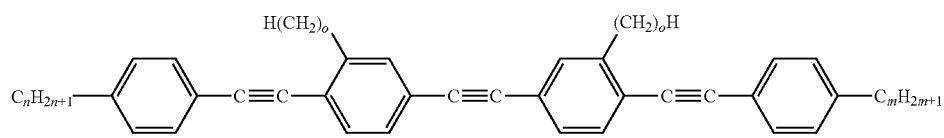
PTPI(o)TP(o)P-n-m, o ∈ {1; 2; 3; 4; 5; 6}
(n ∈ {1; 2; 3; 4; 5; 6; 7} and m ∈ {1; 2; 3; 4; 5; 6; 7})
Examples of compounds of component C
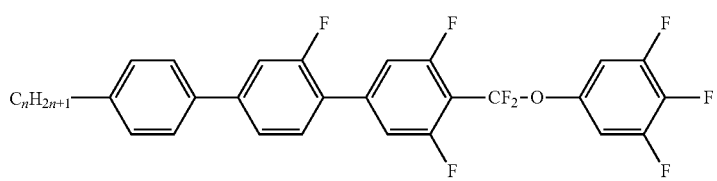
PGUQU-n-F TABLE D-continued
Illustrative structures
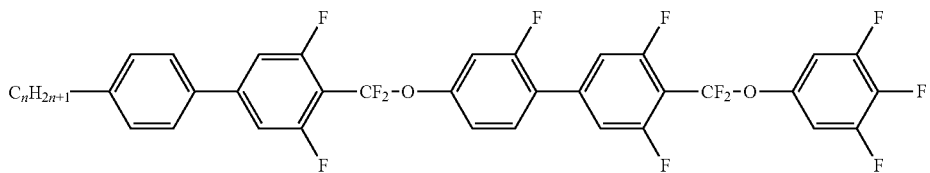
PUQGUQU-n-F
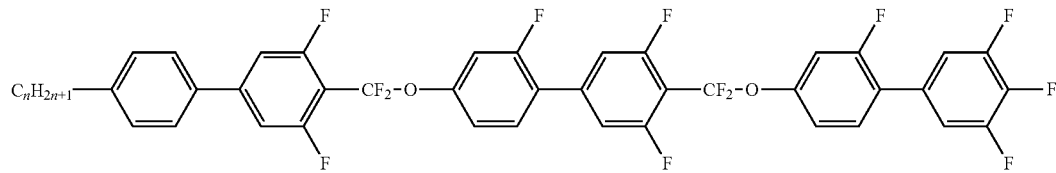
PUQGUQGU-n-F = PU[QGU]$_2$-n-F
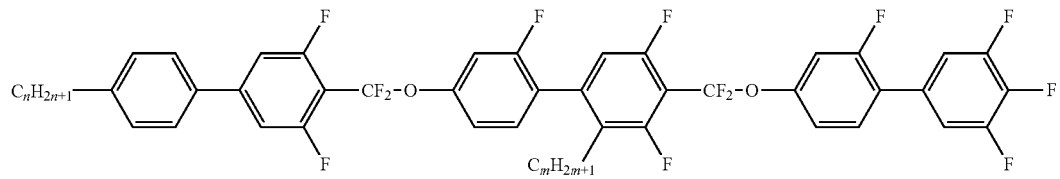
PUQGU(m)QGU-n-F = PU[GQU]$_2^{(m)}$-n-F
(n ⇥ {1; 2; 3; 4; 5; 6; 7} and m ⇥ {1; 2; 3; 4;})
Examples of compounds of component D
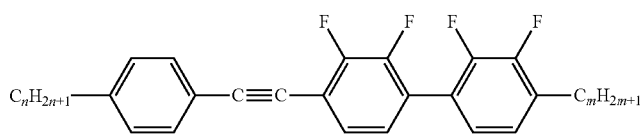
PTYY-n-m
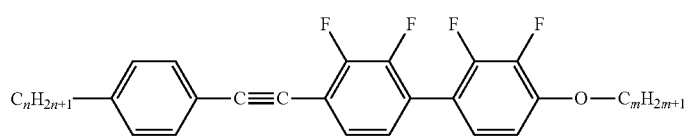
PTYY-n-Om
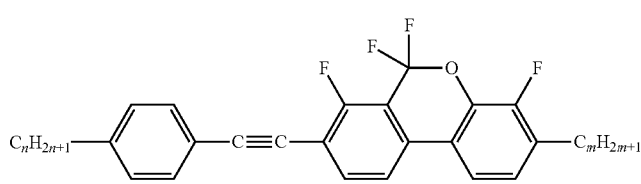
PfX-n-m
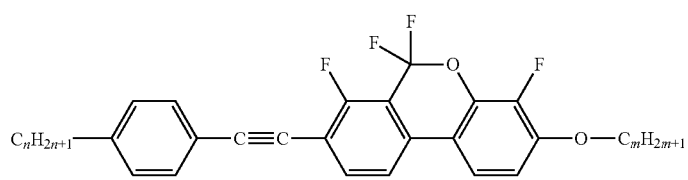
PfX-n-Om
(n ⇥ {1; 2; 3; 4; 5; 6; 7} and m ⇥ {1; 2; 3; 4; 5; 6; 7})

TABLE D-continued
Illustrative structures
Examples of compounds of component E
Compounds having three 6-membered rings
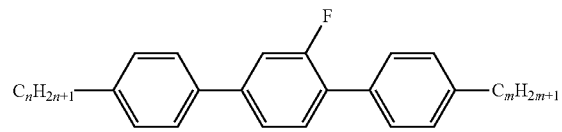
PGP-n-m
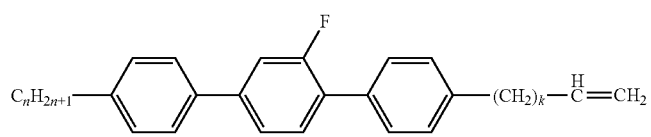
PGP-n-kV
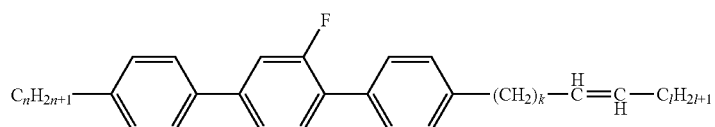
PGP-n-kVI
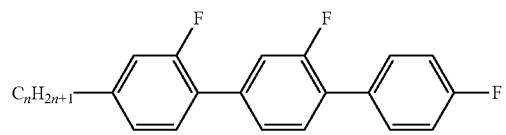
GGP-n-F
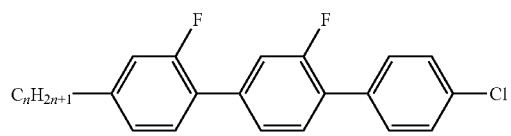
GGP-n-CL
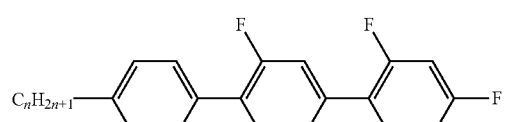
PGIGI-n-F
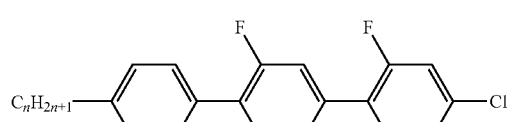
PGIGI-n-CL
(n ⇒ {1; 2; 3; 4; 5; 6; 7}, m ⇒ {1; 2; 3; 4; 5; 6; 7}, and k ⇒ {1; 2; 3; 4}, preferably 0 or 2, and l ⇒ {1; 2; 3})
Compounds having four 6-membered rings
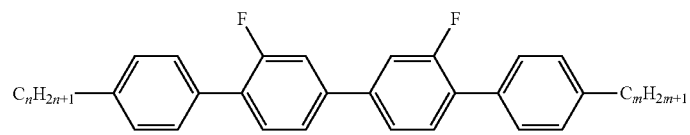
PGIGP-n-m TABLE D-continued
Illustrative structures
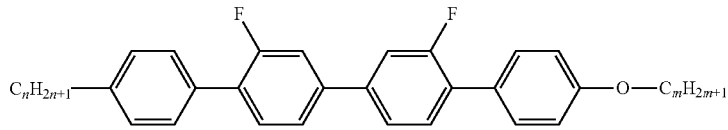
PGIGP-n-Om
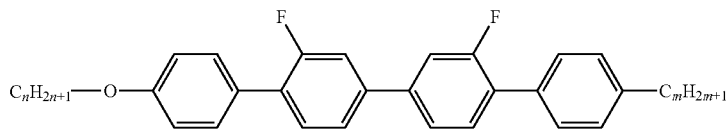
PGIGP-nO-Om
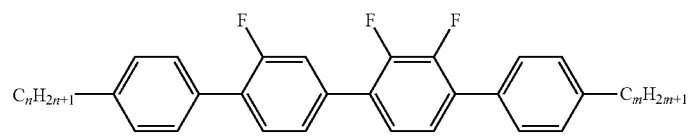
PGIYP-n-m
(n → {1; 2; 3; 4; 5; 6; 7} and m → {1; 2; 3; 4; 5; 6; 7})
Illustrative structures of polar compounds employed:
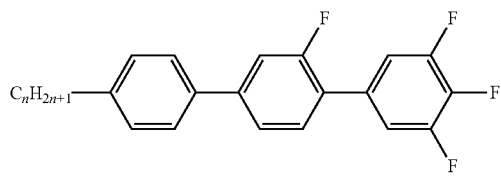
PGU-n-F
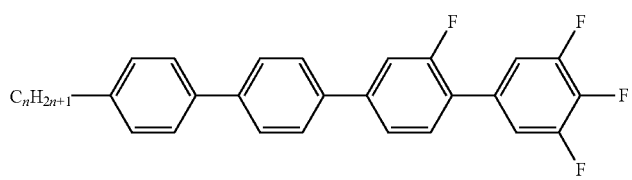
PPGU-n-F
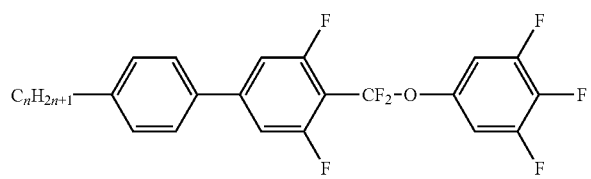
PUQU-n-F
(n → {1; 2; 3; 4; 5; 6; 7})
Illustrative structures of further neutral compounds preferably employed:
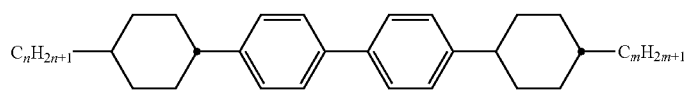
CPPC-n-m TABLE D-continued
Illustrative structures
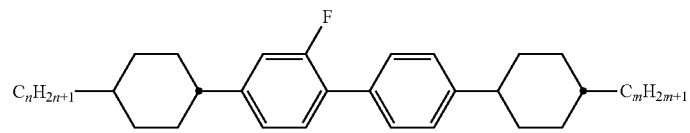
CGPC-n-m
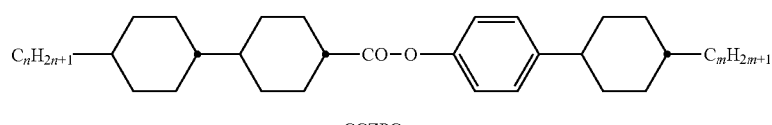
CCZPC-n-m
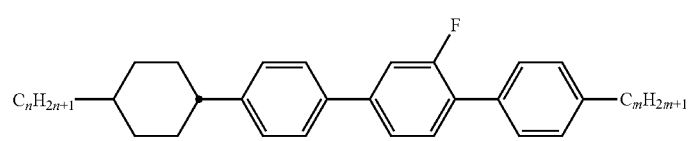
CPGP-n-m
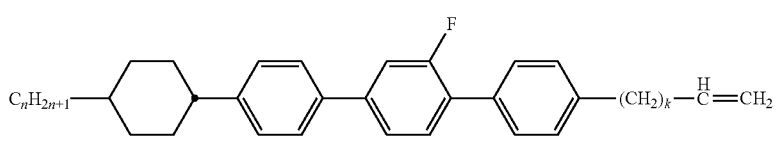
CPGP-n-kV
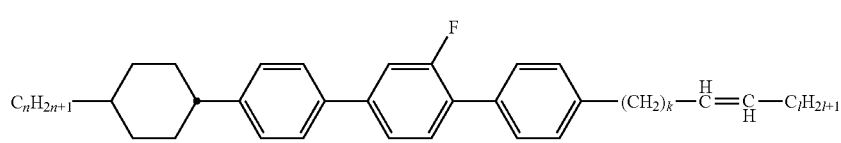
CPGP-n-kVI
(n → {1; 2; 3; 4; 5; 6; 7}, m → {1; 2; 3; 4; 5; 6; 7}, and k → {1; 2; 3; 4}, preferably 0 or 2,
and l → {1; 2; 3})
Illustrative structures of further polar compounds employed:
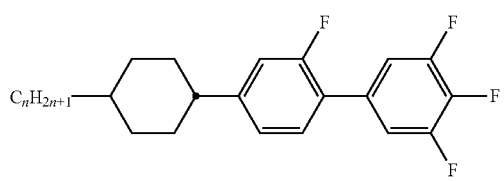
CGU-n-F
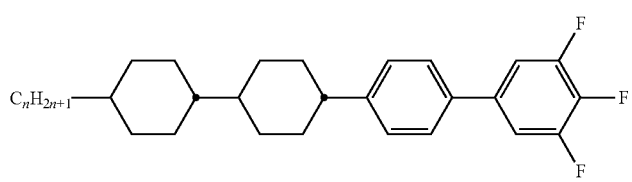
CCPU-n-F
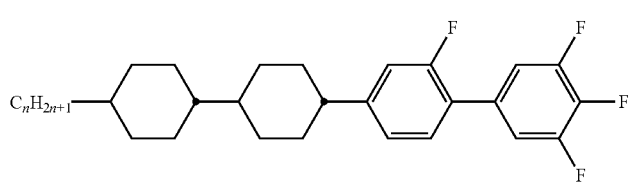
CCGU-n-F TABLE D-continued
Illustrative structures
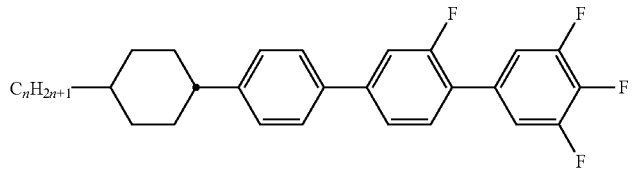
CPGU-n-F
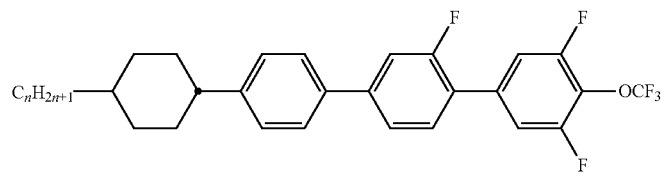
CPGU-n-OT
CC-n-V
(n → {1; 2; 3; 4; 5; 6; 7})
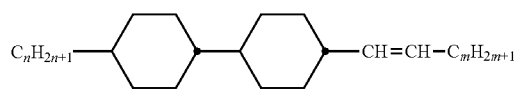
CC-n-Vm
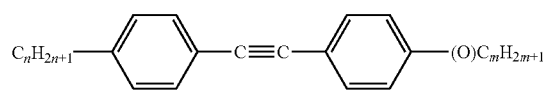
PTP-n-(O)m
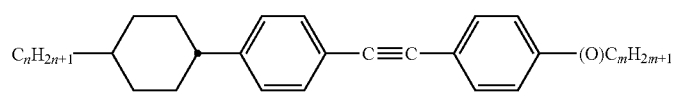
CPTP-n-(O)m
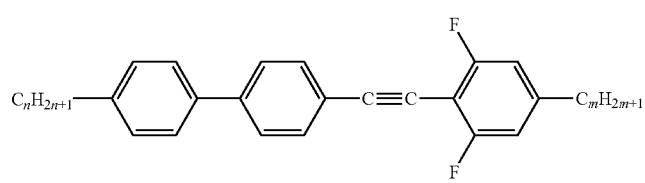
PPTUI-n-m
(n → {1; 2; 3; 4; 5; 6; 7}; m → {1; 2; 3; 4; 5; 6; 7})

The following table, Table E, shows illustrative compounds which can be used as stabiliser in the mesogenic media in accordance with the present invention. The total concentration of these and similar compounds in the media is preferably 5% or less.
TABLE E
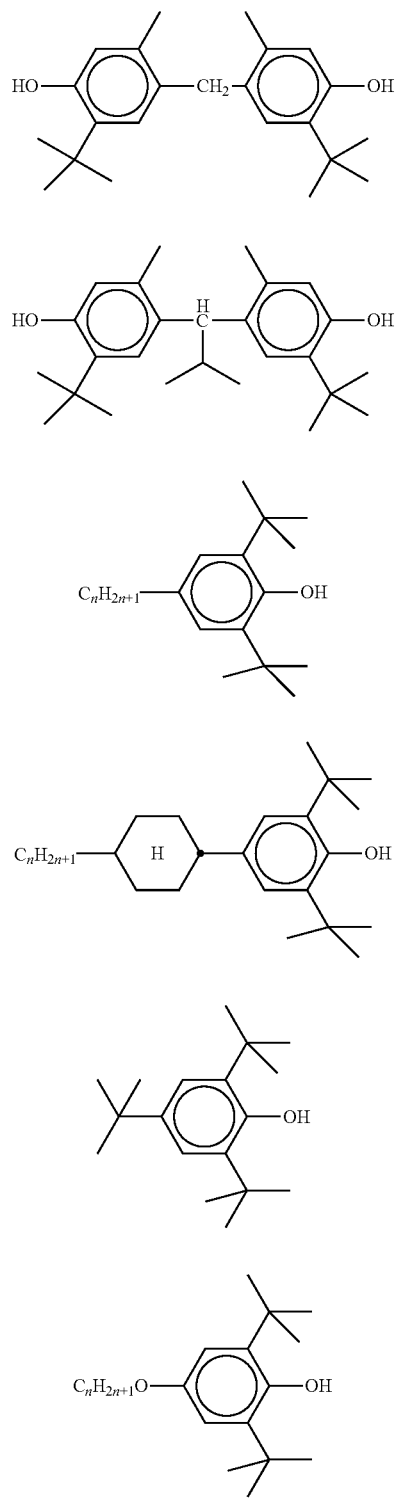
TABLE E-continued
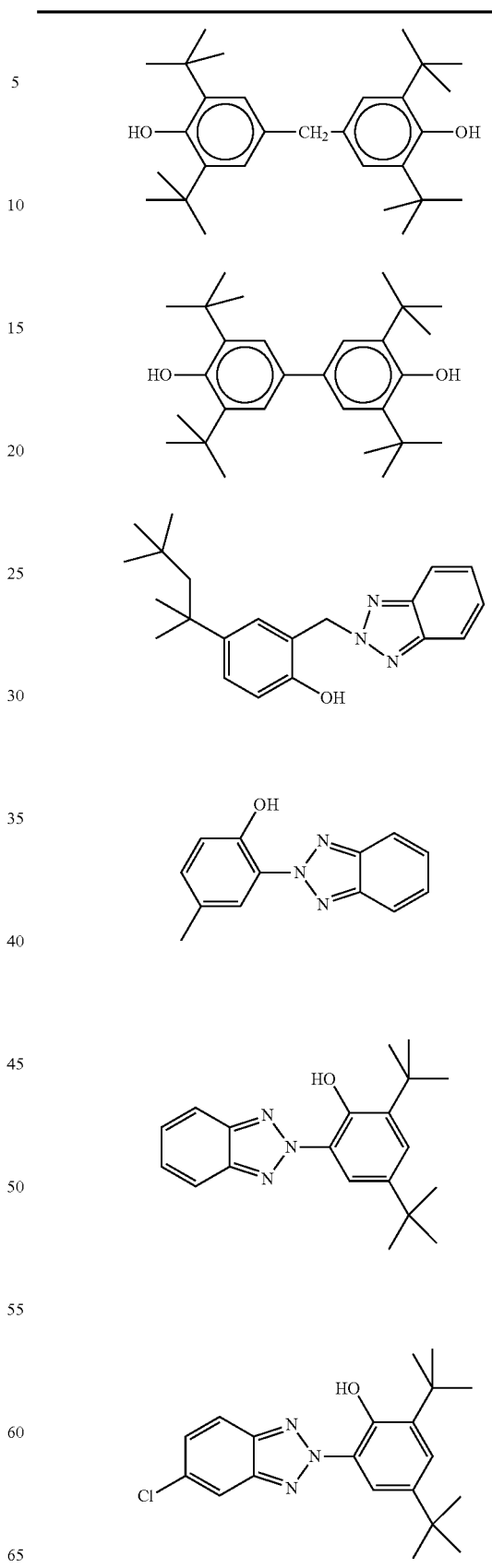

TABLE E-continued
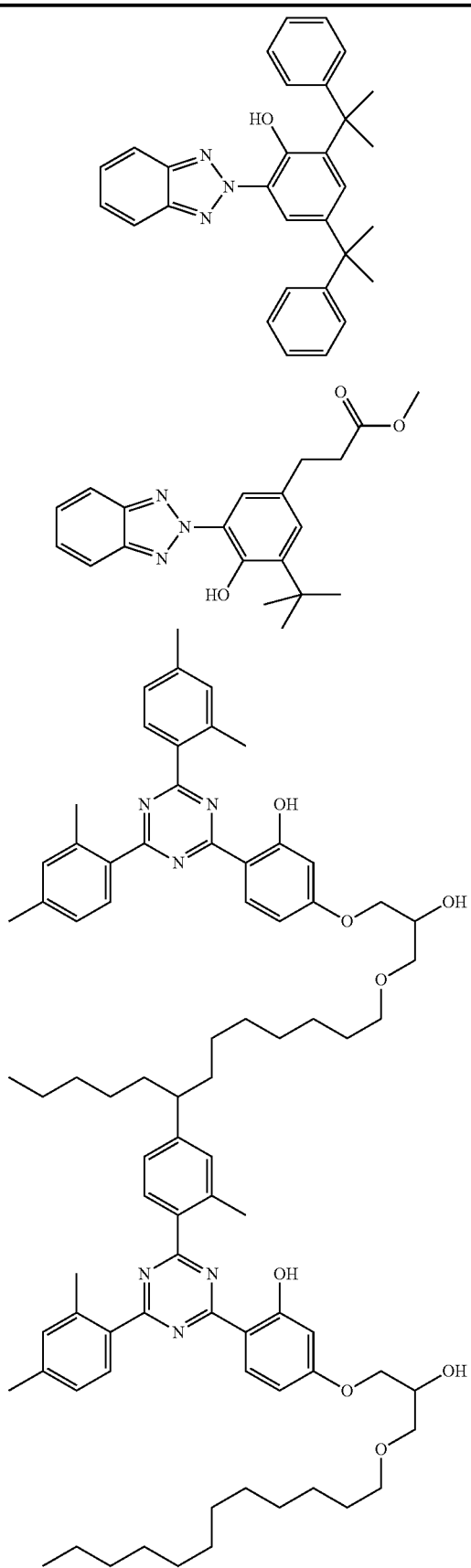
TABLE E-continued
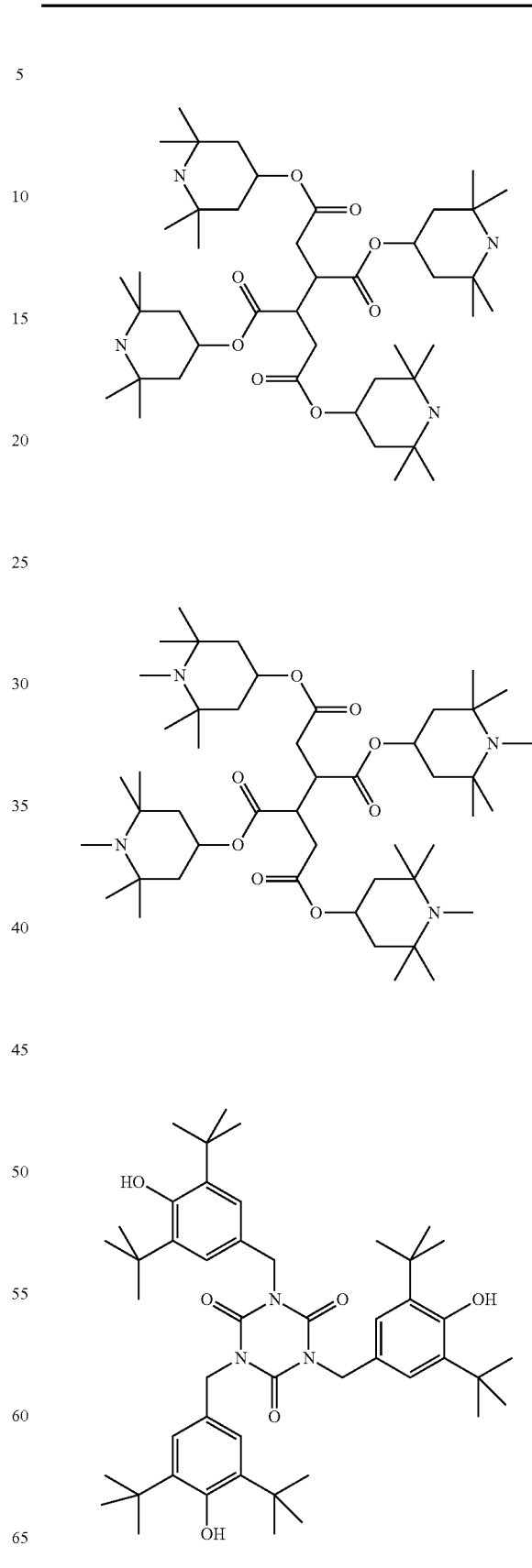

TABLE E-continued

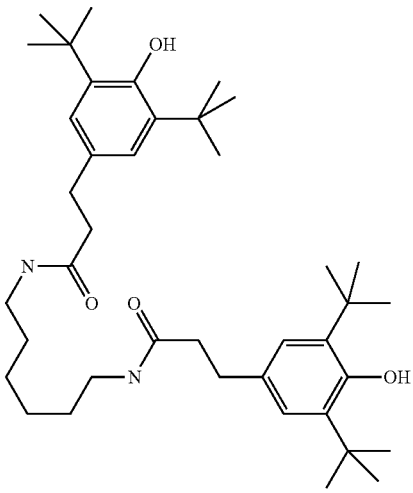 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

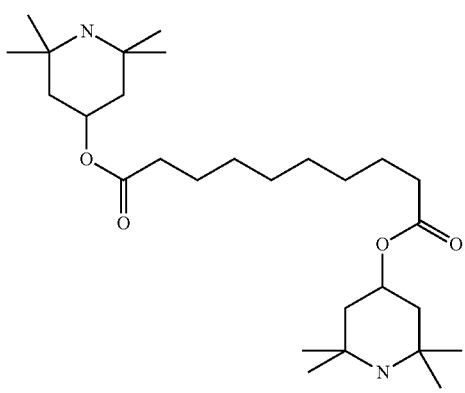

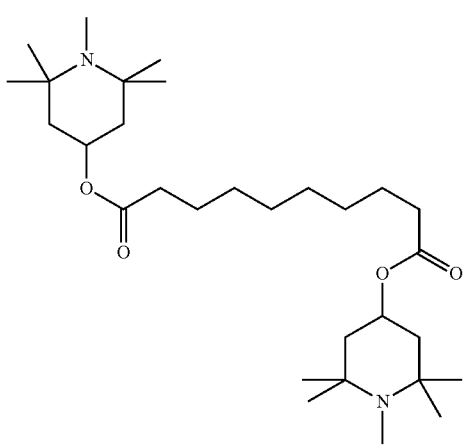

TABLE E-continued

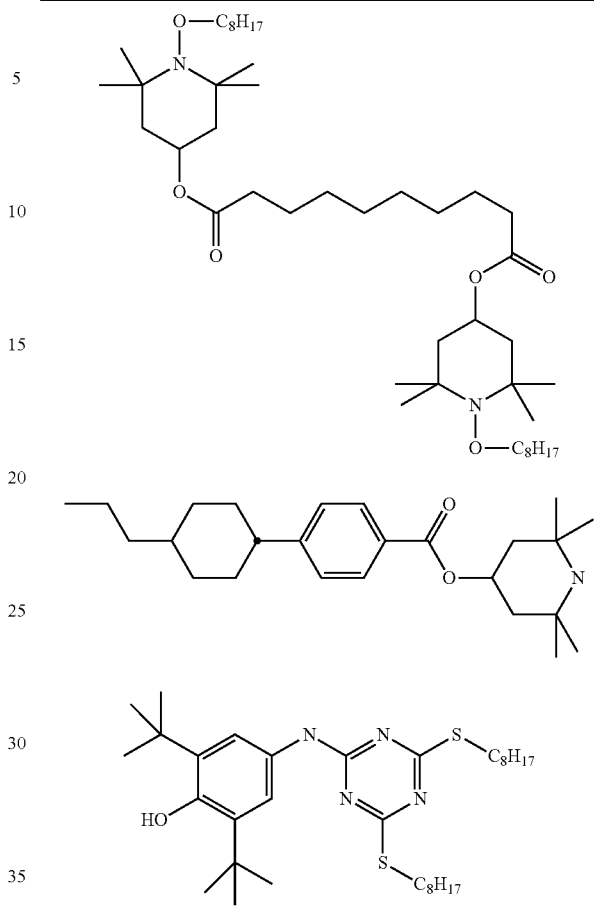

In a preferred embodiment of the present invention, the mesogenic media comprise one or more compounds selected from the group of the compounds from Table E.

The mesogenic media in accordance with the present application preferably comprise two or more, preferably four or more, compounds selected from the group consisting of the compounds from the above tables.

The liquid-crystal media in accordance with the present invention preferably comprise seven or more, preferably eight or more, compounds, preferably compounds having three or more, preferably four or more, different formulae, selected from the group of the compounds from Table D.

EXAMPLES

The following examples illustrate the present invention without limiting it in any way. However, it becomes clear to the person skilled in the art from the physical properties what properties can be achieved and in what ranges they can be modified. In particular, the combination of the various properties which can preferably be achieved is thus well defined for the person skilled in the art.

The acetylenes employed, if not commercially available, are synthesised in accordance with standard laboratory procedures.

Example Compounds of the Formulae I-M and I-U for Component A

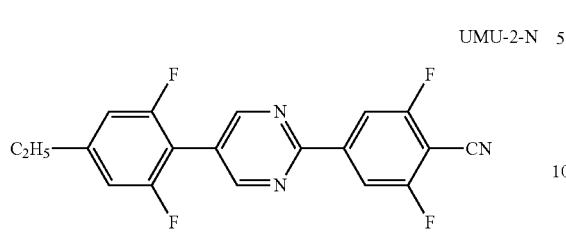
UMU-2-N

Phase sequence: K 174° C. I.

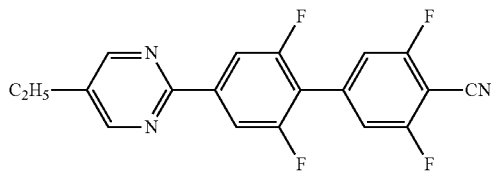
MUU-2-N

Phase sequence: K 170° C. I.

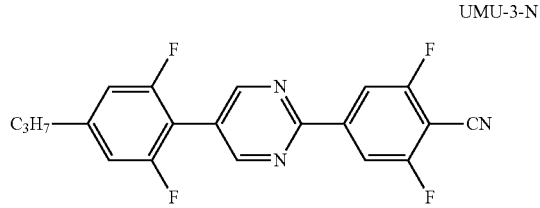
UMU-3-N

Phase sequence: K 131° C. I.

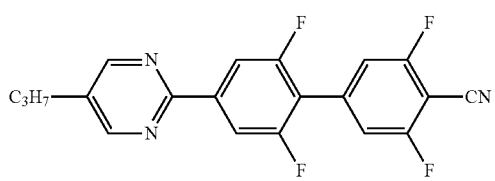
MUU-3-N

Phase sequence: K 123° C. N (103.4° C.) I. $\Delta n=0.2391$ and $\Delta \epsilon =79$.

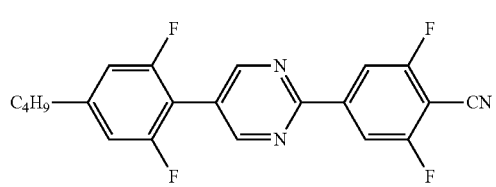
UMU-4-N

Phase sequence: K 86° C. N (75.6° C.) I. $\Delta n=0.2281$ and $\Delta \epsilon =78$.

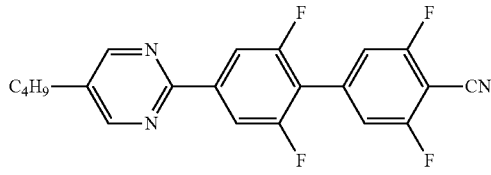
MUU-4-N

Phase sequence: K 72° C. N 89° C. I. $\Delta n=0.2321$ and $\Delta \epsilon =76$.

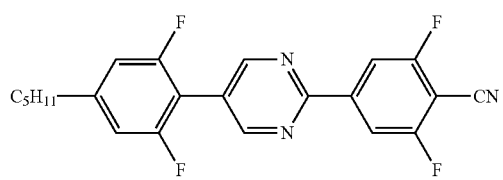
UMU-5-N

Phase sequence: K 85° C. N (78° C.) I. $\Delta n=0.2321$ and $\Delta \epsilon =73$.

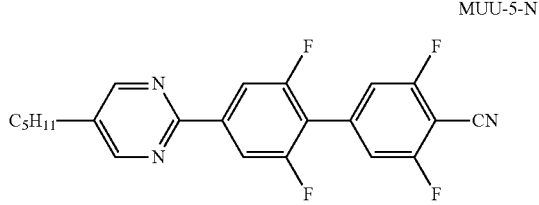
MUU-5-N

Phase sequence: K 81° C. N 92° C. I. $\Delta n=0.2341$ and $\Delta \epsilon =73$.

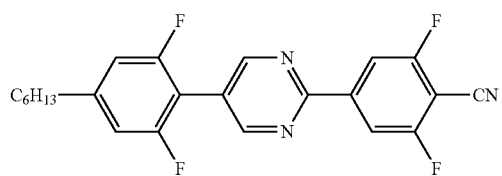
UMU-6-N

Phase sequence: K 67° C. N (68.2° C.) I. $\Delta n=0.2112$ and $\Delta \epsilon =67$.

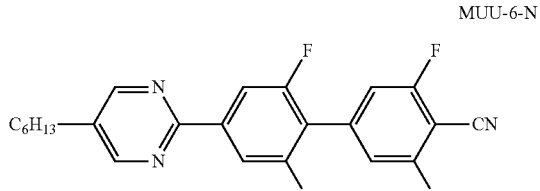
MUU-6-N

Phase sequence: $T_g$ to be determined K 62° C. N 82.2° C. I. $\Delta n=0.2183$ and $\Delta \epsilon =69$.

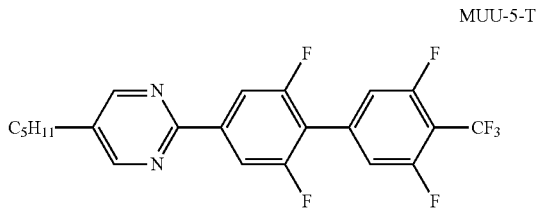

MUU-5-T

Phase sequence: K 100° C. I. Δn=0.1674 and Δε=43.

Use Examples

Comparative Example 0

A liquid-crystalline substance having the abbreviation PTP(2)TP-6-3 is prepared by the method of Hsu, C. S., Shyu, K. F., Chuang, Y. Y. and Wu, S.-T., Liq. Cryst., 27 (2), (2000), pp. 283-287, and investigated with respect to its physical properties, in particular in the microwave region. The compound has a nematic phase and a clearing point (T(N,I)) of 114.5° C. Further physical properties at 20° C. are: $n_e$(589.3 nm)=1.8563; Δn(589.3 nm)=0.3250; $\epsilon_{\parallel}$(1 kHz)=4.3; Δε(1 kHz)=1.8 and $\gamma_1$=2.100 mPa·s. The compound is suitable for applications in the microwave region and/or millimeter wave region, in particular for phase shifters.

TABLE 1a

Properties of the compound PTP(2)TP-6-3 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.35 | 2.42 | 0.278 | 0.0029 | 0.0061 | 45.2 |

Example 0

A binary liquid-crystal mixture M-0, having the composition and properties as indicated in the following table, is prepared.

| Composition | | |
|---|---|---|
| Compound | | |
| No. | Abbreviation | |
| 1 | PTP(2)TP-6-3 | 23.75 |
| 2 | MUU-4-N | 5.00 |
| Σ | | 100.00 |

Physical properties

T (N, I) = 113° C.
$n_o$ (20° C., 589.3 nm) = 1.5407
Δn (20° C., 589.3 nm) = t.b.d.
$\epsilon_{\parallel}$ (20° C., 1 kHz) = 11.1
Δε (20° C., 1 kHz) = 7.8
$k_{11}$ (20° C.) = 12.4 pN
$k_{33}$ (20° C.) = 27.2 pN
$V_0$ (20° C.) = 1.33 V
$\gamma_1$ (20° C.) = t.b.d. mPa · s Remark: t.b.d.: to be determined.

This mixture is suitable for applications in the microwave region and/or millimeter wave region, in particular for phase shifters.

TABLE 1b

Properties of mixture M-0 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | t.b.d. | t.b.d. | t.b.d. | t.b.d. | t.b.d. | t.b.d. |

Remark: t.b.d.: to be determined.

Comparative Example 1

A liquid-crystal mixture CM-1 having the composition and properties as indicated in the following table is prepared.

| Composition | | |
|---|---|---|
| Compound | | |
| No. | Abbreviation | |
| 1 | PTGI(c3)TP-3-4 | 25.0 |
| 2 | PTGI(c4)TP-4-4 | 25.0 |
| 3 | PTP(c3)TP-6-3 | 25.0 |
| 4 | PTP(1, c3)TP-4-4 | 25.0 |
| Σ | | 100.0 |

Physical properties

T (N, I) = 140° C.
$n_o$ (20° C., 589.3 nm) = 1.5407
Δn (20° C., 589.3 nm) = t.b.d.
$\epsilon_{\parallel}$ (20° C., 1 kHz) = 3.5
Δε (20° C., 1 kHz) = 0.8
$k_{11}$ (20° C.) = 9.7 pN
$k_{33}$ (20° C.) = 51.6 pN
$V_0$ (20° C.) = 3.66 V
$\gamma_1$ (20° C.) = 2,220 mPa · s

TABLE 2

Properties of the CM-1 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.26 | 2.37 | 0.273 | 0.0020 | 0.0059 | 46.3 |

TABLE 3

Comparison of the properties of the various examples at 19 GHz and 20° C.

| Example | LC | $\epsilon_{r,\parallel}$ | $\epsilon_{r,\perp}$ | τ | tan $\delta_{\epsilon\ max.}$ | η |
|---|---|---|---|---|---|---|
| C-0 | P2-6-3* | 3.35 | 2.42 | 0.278 | 0.0061 | 45.2 |
| C-0§ | P2-6-3*§ | 3.28§ | 2.41§ | 0.264§ | 0.0070§ | 37.8§ |
| 0 | M-0 | t.b.d. | t.b.d. | t.b.d. | t.b.d. | t.b.d. |
| C-1 | CM-1 | 3.26 | 2.37 | 0.273 | 0.0059 | 46.3 |
| 1-1 | M-1-1 | 3.24 | 2.38 | 0.266 | 0.0062 | 42.7 |
| 1-2 | M-1-2 | 3.25 | 2.41 | 0.259 | 0.0074 | 35.3 |
| C-2 | CM-2 | 3.19 | 2.41 | 0.244 | 0.0143 | 17.2 |
| 2 | M-2 | 3.06 | 2.37 | 0.223 | 0.0114 | 19.8 |
| 3 | M-3 | 2.92 | 2.34 | 0.202 | 0.0116 | 17.5 |
| 4 | M-4 | 3.04 | 2.37 | 0.219 | 0.0119 | 18.3 |
| 5 | M-5 | 3.05 | 2.37 | 0.223 | 0.0121 | 18.4 |
| 6 | M-6§ | 3.11§ | 2.44§ | 0.216§ | 0.0127§ | 16.9§ |
| 7 | M-7§ | 3.11§ | 2.44§ | 0.216§ | 0.0121§ | 17.8§ |
| 8 | M-8 | 3.00 | 2.36 | 0.211 | 0.0140 | 15.0 |
| 9 | M-9 | 3.07 | 2.38 | 0.223 | 0.121 | 18.5 |
| 10 | M-10 | 2.99 | 2.38 | 0.205 | 0.0105 | 19.6 |
| 11 | M-11 | 3.00 | 2.39 | 0.203 | 0.0108 | 18.8 |

TABLE 3-continued

Comparison of the properties of the various examples at 19 GHz and 20° C.

| Example | LC | $\epsilon_{r,\|\|}$ | $\epsilon_{r,\perp}$ | $\tau$ | tan $\delta_{\epsilon\ max.}$ | $\eta$ |
|---|---|---|---|---|---|---|
| 12 | M-12 | 3.00 | 2.39 | 0.205 | 0.0107 | 19.3 |
| 13 | M-13 | 2.98 | 2.38 | 0.202 | 0.0107 | 19.0 |

Notes:
*P2-6-3: PTP(2)TP-6-3,
LC: liquid crystal,
§at 12 GHz and
t.b.d.: to be determined.

Example 1-1

A liquid-crystal mixture M-1-1 having the composition and properties as indicated in the following table is prepared.

| Composition | | |
|---|---|---|
| Compound | | |
| No. | Abbreviation | |
| 1 | PTGI(c3)TP-3-4 | 23.75 |
| 2 | PTGI(c4)TP-4-4 | 23.75 |
| 3 | PTP(c3)TP-6-3 | 23.75 |
| 4 | PTP(1,c3)TP-4-4 | 23.75 |
| 5 | UMU-6-N | 5.00 |
| Σ | | 100.00 |
| Physical properties | | |
| T(N, I) = | | 138° C. |
| $n_o$ (20° C., 589.3 nm) = | | 1.5386 |
| Δn (20° C., 589.3 nm) = | | t.b.d. |
| $\epsilon_{\|\|}$ (20° C., 1 kHz) = | | 7.0 |
| Δ∈ (20° C., 1 kHz) = | | 4.0 |
| $k_{11}$ (20° C.) = | | 10.7 pN |
| $k_{33}$ (20° C.) = | | 31.2 pN |
| $V_0$ (20° C.) = | | 1.73 V |
| $\gamma_1$ (20° C.) = | | 3,216 mPa · s |

Remark: t.b.d.: to be determined.

This mixture is very highly suitable for applications in the microwave region and/or millimeter wave region, in particular for phase shifters.

TABLE 4a

Properties of mixture M-1-1 at 19 GHz

| T/° C. | $\epsilon_{r,\|\|}$ | $\epsilon_{r,\perp}$ | $\tau$ | tan $\delta_{\epsilon,r,\|\|}$ | tan $\delta_{\epsilon,r,\perp}$ | $\eta$ |
|---|---|---|---|---|---|---|
| 20 | 3.24 | 2.38 | 0.266 | 0.0021 | 0.0062 | 42.7 |

The use of 5% of a compound of formula I-U (here UMU-6-N) leads to a very strong increase of Δ∈ at low frequency (1 kHz) and consequently to a drastic reduction of the response time for switching the device on (i.e. $\tau_{on}$) compared to comparative example 2 (CM-1). At the same time the loss in tunability and the increase of the dielectric loss, which leads to a smaller figure of merit ($\eta$) are rather small and thus tolerable for many applications.

Example 1-2

A liquid-crystal mixture M-1-2 having the composition and properties as indicated in the following table is prepared.

| Composition | | |
|---|---|---|
| Compound | | |
| No. | Abbreviation | |
| 1 | PTGI(c3)TP-3-4 | 22.25 |
| 2 | PTGI(c4)TP-4-4 | 22.25 |
| 3 | PTP(c3)TP-6-3 | 22.25 |
| 4 | PTP(1,c3)TP-4-4 | 22.25 |
| 5 | MUU-4-N | 10.00 |
| Σ | | 100.00 |
| Physical properties | | |
| T(N, I) = | | 132° C. |
| $n_o$ (20° C., 589.3 nm) = | | 1.5406 |
| Δn (20° C., 589.3 nm) = | | t.b.d. |
| $\epsilon_{\|\|}$ (20° C., 1 kHz) = | | 11.6.0 |
| Δ∈ (20° C., 1 kHz) = | | 8.1 |
| $k_{11}$ (20° C.) = | | 12.2 pN |
| $k_{33}$ (20° C.) = | | 14.0 pN |
| $V_0$ (20° C.) = | | 1.30 V |
| $\gamma_1$ (20° C.) = | | 3,152 mPa · s |

Remark: t.b.d.: to be determined.

This mixture is very highly suitable for applications in the microwave region and/or millimeter wave region, in particular for phase shifters.

TABLE 4b

Properties of mixture M-1-2 at 19 GHz

| T/° C. | $\epsilon_{r,\|\|}$ | $\epsilon_{r,\perp}$ | $\tau$ | tan $\delta_{\epsilon,r,\|\|}$ | tan $\delta_{\epsilon,r,\perp}$ | $\eta$ |
|---|---|---|---|---|---|---|
| 20 | 3.25 | 2.41 | 0.259 | 0.0025 | 0.0074 | 35.3 |

The use of 10% of a compound of formula I-M (here MUU-4-N) leads to a very strong increase of Δ∈ at low frequency (1 kHz) and consequently to a drastic reduction of the response time for switching the device on (i.e. $\tau_{on}$) compared to comparative example 2 (CM-1). At the same time the loss in tunability and the increase of the dielectric loss, which leads to a smaller figure of merit ($\eta$) are rather small and thus tolerable for many applications.

Comparative Example 2

A liquid-crystal mixture C-2 having the composition and properties as indicated in the following table is prepared.

| Composition | | |
|---|---|---|
| Compound | | |
| No. | Abbreviation | |
| 1 | GGP-3-CL | 10.0 |
| 2 | GGP-5-CL | 20.0 |
| 3 | PPTUI-3-2 | 20.0 |
| 4 | PPTUI-3-4 | 36.0 |
| 5 | CPGP-5-2 | 7.0 |
| 6 | CPGP-5-3 | 7.0 |
| Σ | | 100.0 |

-continued

| Physical properties | |
|---|---|
| T(N, I) = | 173° C. |
| $n_e$ (20° C., 589.3 nm) = | 1.9549 |
| Δn (20° C., 589.3 nm) = | 0.3348 |
| $\epsilon_\parallel$ (20° C., 1 kHz) = | 8.1 |
| Δ∈ (20° C., 1 kHz) = | 4.6 |
| $k_{11}$ (20° C.) = | 24.0 pN |
| $k_{33}$ (20° C.) = | 34.5 pN |
| $V_0$ (20° C.) = | 2.42 V |
| $\gamma_1$ (20° C.) = | 746 mPa·s |

This mixture is suitable for applications in the microwave region and/or millimeter wave region. It has a value of Δ∈, which is comparable to that of the mixture of example 1, however, its figure of merit is way smaller than that of said mixture.

TABLE 5

Properties of mixture C-2 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.19 | 2.41 | 0.245 | 0.0035 | 0.0143 | 17.2 |

Example 2

A liquid-crystal mixture M-2 having the composition and properties as indicated in the following table is prepared.

| Composition Compound | | |
|---|---|---|
| No. | Abbreviation | |
| 1 | UMU-6-N | 5.0 |
| 2 | CC-4-V | 10.0 |
| 3 | PPTUI-3-2 | 20.0 |
| 4 | PPTUI-3-4 | 20.0 |
| 5 | PPTUI-4-4 | 31.0 |
| 6 | CPTP-3-2 | 3.0 |
| 7 | CPTP-4-1 | 3.0 |
| 8 | CPGP-5-2 | 4.0 |
| 9 | CPGP-5-3 | 4.0 |
| Σ | | 100.0 |

| Physical properties | |
|---|---|
| T(N, I) = | 157° C. |
| $n_e$ (20° C., 589.3 nm) = | 1.8180 |
| Δn (20° C., 589.3 nm) = | 0.3068 |
| $\epsilon_\parallel$ (20° C., 1 kHz) = | 7.4 |
| Δ∈ (20° C., 1 kHz) = | 4.8 |
| $k_{11}$ (20° C.) = | 19.2 pN |
| $k_{33}$ (20° C.) = | 24.3 pN |
| $V_0$ (20° C.) = | 2.10 V |
| $\gamma_1$ (20° C.) = | 438 mPa·s |

TABLE 5

Properties of mixture M-2 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.06 | 2.37 | 0.223 | 0.0031 | 0.0114 | 19.8 |

This mixture, which is using 5% of a compound of formula I-U (i.e. UMU-6-N), is very well suitable for applications in the microwave region and/or millimeter wave region, in particular for phase shifters. It has a Δ∈ at low frequency (1 kHz) of 4.8, which is slightly higher than that of the mixture of comparative example 3 (CM-2) and consequently has an even further reduced response time for switching the device on (i.e. $\tau_{on}$) compared to comparative example 3. At the same time it shows a significant decrease of the dielectric loss, which leads to a corresponding larger figure of merit (η), while the loss in tuneability is rather small and thus tolerable for most applications.

Example 3

A liquid-crystal mixture M-3 having the composition and properties as indicated in the following table is prepared.

| Composition Compound | | |
|---|---|---|
| No. | Abbreviation | |
| 1 | UMU-4-N | 5.0 |
| 2 | UMU-6-N | 5.0 |
| 3 | CC-4-V | 20.0 |
| 4 | PPTUI-3-2 | 15.0 |
| 5 | PPTUI-3-4 | 15.0 |
| 6 | PPTUI-4-4 | 26.0 |
| 7 | CPTP-3-2 | 3.0 |
| 8 | CPTP-4-1 | 3.0 |
| 9 | CPGP-5-2 | 4.0 |
| 10 | CPGP-5-3 | 4.0 |
| Σ | | 100.0 |

| Physical properties | |
|---|---|
| T(N, I) = | 139° C. |
| $n_e$ (20° C., 589.3 nm) = | 1.7737 |
| Δn (20° C., 589.3 nm) = | 0.2673 |
| $\epsilon_\parallel$ (20° C., 1 kHz) = | 12.2 |
| Δ∈ (20° C., 1 kHz) = | 9.0 |
| $k_{11}$ (20° C.) = | 17.6 pN |
| $k_{33}$ (20° C.) = | 18.6 pN |
| $V_0$ (20° C.) = | 1.48 V |
| $\gamma_1$ (20° C.) = | 297 mPa·s |

TABLE 6

Properties of mixture M-3 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 2.92 | 2.34 | 0.202 | 0.0032 | 0.0116 | 17.5 |

This mixture, which is using a total of 10% of compounds of formula I-U (i.e. 5% each of UMU-4-N and UMU-6-N), is very well suitable for applications in the microwave region and/or millimeter wave region, in particular for phase shifters. It has a Δ∈ at low frequency (1 kHz) of 9.0, which is almost double the value of the mixture of the mixture of comparative example 3 (CM-2) and consequently has an even further reduced response time for switching the device on (i.e. $\tau_{on}$) compared to comparative example 3. At the same time it even shows a significant decrease of the dielectric loss, which leads to a corresponding larger figure of merit (η), while the loss in tuneability is still rather small and thus tolerable for most applications.

Example 4

A liquid-crystal mixture M-4 having the composition and properties as indicated in the following table is prepared.

| Composition | | |
|---|---|---|
| Compound | | |
| No. | Abbreviation | |
| 1 | UMU-4-N | 5.0 |
| 2 | UMU-6-N | 5.0 |
| 3 | CC-4-V | 6.0 |
| 4 | PTP-4-5 | 10.0 |
| 5 | PPTUI-3-2 | 10.0 |
| 6 | PPTUI-3-4 | 20.0 |
| 7 | PPTUI-4-4 | 30.0 |
| 8 | CPTP-3-2 | 3.0 |
| 9 | CPTP-4-1 | 3.0 |
| 10 | CPGP-5-2 | 4.0 |
| 11 | CPGP-5-3 | 4.0 |
| Σ | | 100.0 |

| Physical properties | |
|---|---|
| T(N, I) = | 140.5° C. |
| $n_e$ (20° C., 589.3 nm) = | 1.8115 |
| Δn (20° C., 589.3 nm) = | 0.2984 |
| $\epsilon_\parallel$ (20° C., 1 kHz) = | 12.6 |
| Δ∈ (20° C., 1 kHz) = | 9.4 |
| $k_{11}$ (20° C.) = | 18.2 pN |
| $k_{33}$ (20° C.) = | 18.4 pN |
| $V_0$ (20° C.) = | 1.48 V |
| $\gamma_1$ (20° C.) = | 431 mPa·s |

TABLE 7

Properties of mixture M-4 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.04 | 2.37 | 0.219 | 0.032 | 0.0119 | 18.3 |

This mixture, which is also using a total of 10% of compounds of formula I-U, like the mixture of the previous example, example 3, is also very well suitable for applications in the microwave region and/or millimeter wave region, in particular for phase shifters. It has an even increased value of Δ∈ at low frequency (1 kHz) of 9.4 and, otherwise, it shows properties, which are comparable to those of the mixture of example 3.

Example 5

A liquid-crystal mixture M-5 having the composition and properties as indicated in the following table is prepared.

| Composition | | |
|---|---|---|
| Compound | | |
| No. | Abbreviation | |
| 1 | UMU-4-N | 5.0 |
| 2 | UMU-6-N | 5.0 |
| 3 | CC-4-V | 10.0 |
| 4 | PPTUI-3-2 | 20.0 |
| 5 | PPTUI-3-4 | 20.0 |
| 6 | PPTUI-4-4 | 26.0 |
| 7 | CPTP-3-2 | 3.0 |
| 8 | CPTP-4-1 | 3.0 |
| 9 | CPGP-5-2 | 4.0 |
| 10 | CPGP-5-3 | 4.0 |
| Σ | | 100.0 |

| Physical properties | |
|---|---|
| T(N, I) = | 154° C. |
| $n_e$ (20° C., 589.3 nm) = | 1.8139 |
| Δn (20° C., 589.3 nm) = | 0.3020 |
| $\epsilon_\parallel$ (20° C., 1 kHz) = | 12.8 |
| Δ∈ (20° C., 1 kHz) = | 9.5 |
| $k_{11}$ (20° C.) = | 19.0 pN |
| $k_{33}$ (20° C.) = | 22.0 pN |
| $V_0$ (20° C.) = | 1.49 V |
| $\gamma_1$ (20° C.) = | 441 mPa·s |

This mixture is very highly suitable for applications in the microwave region and/or millimeter wave region, in particular for phase shifters.

TABLE 8

Properties of mixture M-5 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.05 | 2.37 | 0.223 | 0.0033 | 0.0121 | 18.4 |

This mixture, which is also using a total of 10% of compounds of formula I-U, like the mixtures of the two previous examples, examples 3 and 4, is also very well suitable for applications in the microwave region and/or millimeter wave region, in particular for phase shifters. It has an even slightly more increased Δ∈ at low frequency (1 kHz) of 9.5 and, otherwise, it shows properties, which are has comparable to those of the mixture of examples 3 and 4.

Example 6

A liquid-crystal mixture M-6 having the composition and properties as indicated in the following table is prepared.

| Composition | | |
|---|---|---|
| Compound | | |
| No. | Abbreviation | |
| 1 | MUU-4-N | 5.0 |
| 2 | CC-4-V | 10.0 |
| 3 | PPTUI-3-2 | 20.0 |
| 4 | PPTUI-3-4 | 20.0 |
| 5 | PPTUI-4-4 | 31.0 |
| 6 | CPTP-3-2 | 3.0 |
| 7 | CPTP-4-1 | 3.0 |
| 8 | CPGP-5-2 | 4.0 |
| 9 | CPGP-5-3 | 4.0 |
| Σ | | 100.0 |

| Physical properties | |
|---|---|
| T(N, I) = | 158.5° C. |
| $n_e$ (20° C., 589.3 nm) = | 1.8215 |
| Δn (20° C., 589.3 nm) = | 0.3098 |
| $\epsilon_\parallel$ (20° C., 1 kHz) = | 8.0 |
| Δ∈ (20° C., 1 kHz) = | 5.1 |
| $k_{11}$ (20° C.) = | 19.0 pN |
| $k_{33}$ (20° C.) = | 24.6 pN |
| $V_0$ (20° C.) = | 2.04 V |
| $\gamma_1$ (20° C.) = | 458 mPa·s |

This mixture is very highly suitable for applications in the microwave region and/or millimeter wave region, in particular for phase shifters.

TABLE 9

Properties of mixture M-6 at 12 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.11 | 2.44 | 0.216 | 0.0031 | 0.0121 | 17.8 |

This mixture, which is using 5% of a compound of formula I-M with a terminal cyano group, is very well suitable for applications in the microwave region and/or millimeter wave region, in particular for phase shifters.

Example 7

A liquid-crystal mixture M-7 having the composition and properties as indicated in the following table is prepared.

| Composition Compound | | |
|---|---|---|
| No. | Abbreviation | |
| 1 | MUU-5-T | 5.0 |
| 2 | CC-4-V | 10.0 |
| 3 | PPTUI-3-2 | 20.0 |
| 4 | PPTUI-3-4 | 20.0 |
| 5 | PPTUI-4-4 | 31.0 |
| 6 | CPTP-3-2 | 3.0 |
| 7 | CPTP-4-1 | 3.0 |
| 8 | CPGP-5-2 | 4.0 |
| 9 | CPGP-5-3 | 4.0 |
| Σ | | 100.0 |
| Physical properties | | |
| T(N, I) = | | 157° C. |
| $n_e$ (20° C., 589.3 nm) = | | 1.8169 |
| Δn (20° C., 589.3 nm) = | | 0.3070 |
| $\epsilon_{\parallel}$ (20° C., 1 kHz) = | | 6.1 |
| Δ$\epsilon$ (20° C., 1 kHz) = | | 3.3 |
| $k_{11}$ (20° C.) = | | 19.8 pN |
| $k_{33}$ (20° C.) = | | 25.8 pN |
| $V_0$ (20° C.) = | | 2.57 V |
| $\gamma_1$ (20° C.) = | | 445 mPa · s |

This mixture is very highly suitable for applications in the microwave region and/or millimeter wave region, in particular for phase shifters.

TABLE 10

Properties of mixture M-7 at 12 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.11 | 2.44 | 0.216 | 0.0033 | 0.0127 | 16.9 |

This mixture, which is using 5% of a compound of formula I-M with a terminal trifluoromethyl group, is very well suitable for applications in the microwave region and/or millimeter wave region, in particular for phase shifters.

Example 8

A liquid-crystal mixture M-8 having the composition and properties as indicated in the following table is prepared.

| Composition Compound | | |
|---|---|---|
| No. | Abbreviation | |
| 1 | UMU-6-N | 5.0 |
| 2 | CC-4-V | 12.0 |
| 3 | PPTUI-3-2 | 7.0 |
| 4 | PPTUI-3-4 | 10.0 |
| 5 | PPTUI-4-4 | 30.0 |
| 6 | GGP-3-CL | 9.0 |
| 7 | GGP-5-CL | 17.0 |
| 8 | CPGP-5-2 | 5.0 |
| 9 | CPGP-5-3 | 5.0 |
| Σ | | 100.0 |
| Physical properties | | |
| T(N, I) = | | 141° C. |
| $n_e$ (20° C., 589.3 nm) = | | 1.7899 |
| Δn (20° C., 589.3 nm) = | | 0.2773 |
| $\epsilon_{\parallel}$ (20° C., 1 kHz) = | | 11.4 |
| Δ$\epsilon$ (20° C., 1 kHz) = | | 7.9 |
| $k_{11}$ (20° C.) = | | 18.8 pN |
| $k_{33}$ (20° C.) = | | 19.8 pN |
| $V_0$ (20° C.) = | | 1.63 V |
| $\gamma_1$ (20° C.) = | | 372 mPa · s |

This mixture is very highly suitable for applications in the microwave region and/or millimeter wave region, in particular for phase shifters.

TABLE 11

Properties of mixture M-8 at 19 GHz

| T/° C. | $\epsilon_{r,\parallel}$ | $\epsilon_{r,\perp}$ | $\tau$ | $\tan \delta_{\epsilon,r,\parallel}$ | $\tan \delta_{\epsilon,r,\perp}$ | $\eta$ |
|---|---|---|---|---|---|---|
| 20 | 3.00 | 2.37 | 0.211 | 0.0038 | 0.0140 | 15.0 |

This mixture, which is using 5% of a compound of formula I-U with a terminal cyano group, is very well suitable for applications in the microwave region and/or millimeter wave region, in particular for phase shifters.

Example 9

A liquid-crystal mixture M-9 having the composition and properties as indicated in the following table is prepared.

| Composition Compound | | |
|---|---|---|
| No. | Abbreviation | |
| 1 | UMU-6-N | 5.0 |
| 2 | CC-4-V | 10.0 |
| 3 | PPTUI-3-2 | 20.0 |
| 4 | PPTUI-3-4 | 20.0 |
| 5 | PPTUI-4-4 | 31.0 |
| 6 | GGP-3-CL | 3.0 |
| 7 | GGP-5-CL | 3.0 |
| 8 | CPGP-5-2 | 4.0 |
| 9 | CPGP-5-3 | 4.0 |
| Σ | | 100.0 |

-continued

| Physical properties | |
|---|---|
| T(N, I) = | 153° C. |
| $n_e$ (20° C., 589.3 nm) = | 1.8236 |
| Δn (20° C., 589.3 nm) = | 0.3105 |
| $\epsilon_\parallel$ (20° C., 1 kHz) = | 8.7 |
| Δ$\epsilon$ (20° C., 1 kHz) = | 5.7 |
| $k_{11}$ (20° C.) = | 18.6 pN |
| $k_{33}$ (20° C.) = | 24.1 pN |
| $V_0$ (20° C.) = | 1.92 V |
| $\gamma_1$ (20° C.) = | 422 mPa·s |

This mixture is very highly suitable for applications in the microwave region and/or millimeter wave region, in particular for phase shifters.

TABLE 12

Properties of mixture M-9 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.07 | 2.38 | 0.223 | 0.0032 | 0.0121 | 18.5 |

This mixture, which is using 5% of a compound of formula I-U, is very well suitable for applications in the microwave region and/or millimeter wave region, in particular for phase shifters.

Example 10

A liquid-crystal mixture M-10 having the composition and properties as indicated in the following table is prepared.

| Composition Compound | | |
|---|---|---|
| No. | Abbreviation | |
| 1 | UMU-6-N | 4.0 |
| 2 | CC-4-V | 8.0 |
| 3 | PPTUI-3-2 | 10.0 |
| 4 | PPTUI-3-4 | 16.0 |
| 5 | PPTUI-4-4 | 30.0 |
| 6 | PTP-3-5 | 16.0 |
| 7 | PTP-4-5 | 16.0 |
| Σ | | 100.0 |

| Physical properties | |
|---|---|
| T(N, I) = | 94° C. |
| $n_o$ (20° C., 589.3 nm) = | 1.5144 |
| Δn (20° C., 589.3 nm) = | t.b.d. |
| $\epsilon_\parallel$ (20° C., 1 kHz) = | 6.4 |
| Δ$\epsilon$ (20° C., 1 kHz) = | 3.5 |
| $k_{11}$ (20° C.) = | 12.4 pN |
| $k_{33}$ (20° C.) = | 19.0 pN |
| $V_0$ (20° C.) = | 1.98 V |
| $\gamma_1$ (20° C.) = | 234 mPa·s |

Remaks. t.b.d.: to be determined.

This mixture is very highly suitable for applications in the microwave region and/or millimeter wave region, in particular for phase shifters.

TABLE 13

Properties of mixture M-10 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 2.99 | 2.38 | 0.205 | 0.0032 | 0.0105 | 19.6 |

This mixture, which is using 4% of a compound of formula I-U, is very well suitable for applications in the microwave region and/or millimeter wave region, in particular for phase shifters.

Example 11

A liquid-crystal mixture M-11 having the composition and properties as indicated in the following table is prepared.

| Composition Compound | | |
|---|---|---|
| No. | Abbreviation | |
| 1 | UMU-6-N | 4.0 |
| 2 | CC-3-V | 8.0 |
| 3 | PPTUI-3-2 | 10.0 |
| 4 | PPTUI-3-4 | 16.0 |
| 5 | PPTUI-4-4 | 30.0 |
| 6 | PTP-3-5 | 16.0 |
| 7 | PTP-4-5 | 16.0 |
| Σ | | 100.0 |

| Physical properties | |
|---|---|
| T(N, I) = | 95° C. |
| $n_o$ (20° C., 589.3 nm) = | 1.5138 |
| Δn (20° C., 589.3 nm) = | t.b.d. |
| $\epsilon_\parallel$ (20° C., 1 kHz) = | 6.3 |
| Δ$\epsilon$ (20° C., 1 kHz) = | 3.5 |
| $k_{11}$ (20° C.) = | 12.7 pN |
| $k_{33}$ (20° C.) = | 19.0 pN |
| $V_0$ (20° C.) = | 2.01 V |
| $\gamma_1$ (20° C.) = | 227 mPa·s |

Remaks. t.b.d.: to be determined.

This mixture is very highly suitable for applications in the microwave region and/or millimeter wave region, in particular for phase shifters.

TABLE 14

Properties of mixture M-11 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.00 | 2.39 | 0.203 | 0.0034 | 0.0108 | 18.8 |

This mixture, which is using 4% of a compound of formula I-U, is very well suitable for applications in the microwave region and/or millimeter wave region, in particular for phase shifters.

Example 12

A liquid-crystal mixture M-12 having the composition and properties as indicated in the following table is prepared.

| Composition Compound | | |
|---|---|---|
| No. | Abbreviation | |
| 1 | UMU-6-N | 4.0 |
| 2 | CC-4-V | 10.0 |
| 3 | PPTUI-3-2 | 10.0 |
| 4 | PPTUI-3-4 | 18.0 |
| 5 | PPTUI-4-4 | 30.0 |
| 6 | PTP-3-5 | 14.0 |
| 7 | PTP-4-5 | 14.0 |
| Σ | | 100.0 |
| Physical properties | | |
| T(N, I) = | | 98° C. |
| $n_o$ (20° C., 589.3 nm) = | | 1.7878 |
| Δn (20° C., 589.3 nm) = | | 0.2750 |
| $\epsilon_{\parallel}$ (20° C., 1 kHz) = | | 6.4 |
| Δ∈ (20° C., 1 kHz) = | | 3.5 |
| $k_{11}$ (20° C.) = | | 13.1 pN |
| $k_{33}$ (20° C.) = | | 19.5 pN |
| $V_0$ (20° C.) = | | 2.03 V |
| $\gamma_1$ (20° C.) = | | 228 mPa · s |

This mixture is very highly suitable for applications in the microwave region and/or millimeter wave region, in particular for phase shifters.

TABLE 15

Properties of mixture M-12 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 3.00 | 2.38 | 0.205 | 0.0033 | 0.0107 | 19.3 |

This mixture, which is using 4% of a compound of formula I-U, is very well suitable for applications in the microwave region and/or millimeter wave region, in particular for phase shifters.

Example 13

A liquid-crystal mixture M-13 having the composition and properties as indicated in the following table is prepared.

| Composition Compound | | |
|---|---|---|
| No. | Abbreviation | |
| 1 | UMU-6-N | 4.0 |
| 2 | CC-4-V | 6.0 |
| 3 | PPTUI-3-4 | 20.0 |
| 4 | PPTUI-4-4 | 20.0 |
| 5 | PTP-3-5 | 20.0 |
| 6 | PTP-4-5 | 20.0 |
| Σ | | 100.0 |
| Physical properties | | |
| T(N, I) = | | 85° C. |
| $n_o$ (20° C., 589.3 nm) = | | 1.5153 |
| Δn (20° C., 589.3 nm) = | | t.b.d. |
| $\epsilon_{\parallel}$ (20° C., 1 kHz) = | | 6.2 |
| Δ∈ (20° C., 1 kHz) = | | 3.4 |
| $k_{11}$ (20° C.) = | | 11.8 pN |
| $k_{33}$ (20° C.) = | | 18.2 pN |
| $V_0$ (20° C.) = | | 1.99 V |
| $\gamma_1$ (20° C.) = | | 216 mPa · s |

Remaks. t.b.d.: to be determined.

This mixture is very highly suitable for applications in the microwave region and/or millimeter wave region, in particular for phase shifters.

TABLE 16

Properties of mixture M-13 at 19 GHz

| T/° C. | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| 20 | 2.98 | 2.38 | 0.202 | 0.0033 | 0.0107 | 19.0 |

This mixture, which is using 4% of a compound of formula I-U, is very well suitable for applications in the microwave region and/or millimeter wave region, in particular for phase shifters.

The invention claimed is:

1. A liquid-crystal medium, comprising one or more compounds of formulae I-M or I-U,

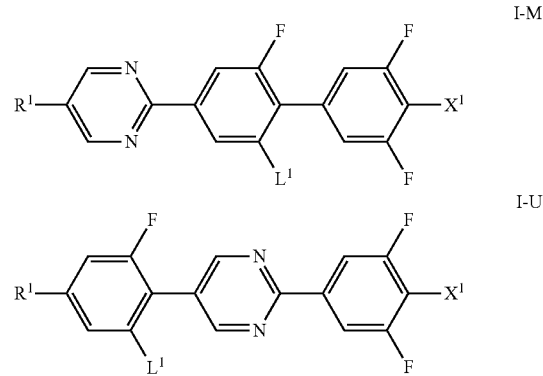

wherein

R$^1$ is alkyl, which is straight chain or branched, is un-substituted, mono- or poly-substituted by F, Cl or CN, and in which one or more CH$_2$ groups are optionally replaced, in each case independently from one another, by —O—, —S—, —NR$^{01}$—, —SiR$^{01}$R$^{02}$—, —CO—, —COO—, —OCO—, —OCO—O—, —S—CO—, —CO—S—, —CY$^{01}$=CY$^{02}$— or —C≡C— in such a manner that O and/or S atoms are not linked directly to one another, L$^1$ is F, X$^1$ is F, CN or CF$_3$, Y$^{01}$ and Y$^{02}$ are, independently of each other, F, Cl or CN, and alternatively one of them may be H, and R$^{01}$ and R$^{02}$ are, independently of each other, H or alkyl with 1 to 12 C-atoms and comprising one or more compounds of formula I

I wherein

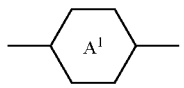

denotes

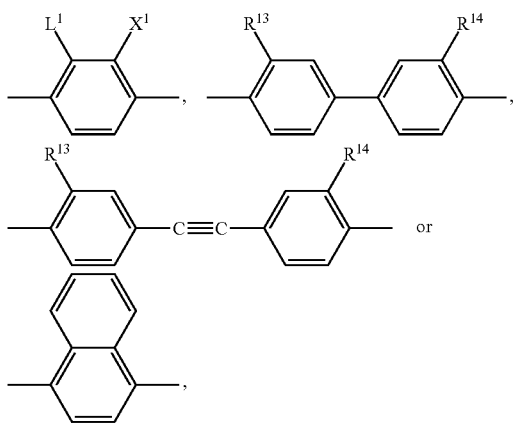

L$^{1'}$ denotes H, alkyl having 1 to 6 C atoms, cycloalkyl having 3 to 6 C atoms or cycloalkenyl having 4 to 6 C atoms, X$^{1'}$ denotes H, alkyl having 1 to 3 C atoms or halogen, R$^{11}$ to R$^{14}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of R$^{13}$ and R$^{14}$ or both also denote H.

2. A liquid-crystal medium according to claim 1, wherein

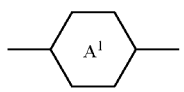

denotes

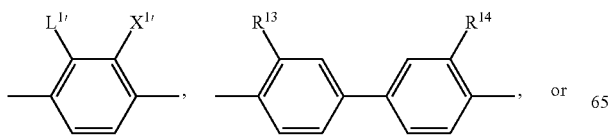

or

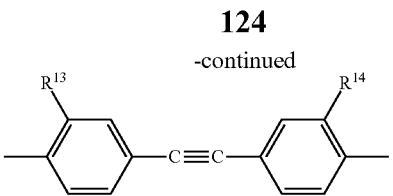

L$^{1'}$ denotes H, alkyl having 1 to 6 C atoms, cycloalkyl having 3 to 6 C atoms or cycloalkenyl having 4 to 6 C atoms, X$^{1'}$ denotes H, alkyl having 1 to 3 C atoms or halogen, R$^{13}$ to R$^{14}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of R$^{13}$ and R$^{14}$ or both also denote H.

3. A liquid-crystal medium according to claim 1, wherein the one or more compounds of formula I comprise one or more compounds of formula I-2

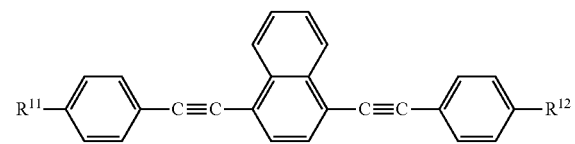
I-2 wherein R$^{11}$ and R$^{12}$ have the respective meanings given in claim 1.

4. A liquid-crystal medium according to claim 1, additionally comprising one or more components C to F:

a strongly dielectrically positive component, component C, which has a dielectric anisotropy of 10 or more at a temperature of 20° C. and a frequency of 1 kHz, a strongly dielectrically negative component, component D, which has a dielectric anisotropy of −5 or less at a temperature of 20° C. and a frequency of 1 kHz, a component, component E, which consists of compounds having seven or more five- or six-membered rings and has a dielectric anisotropy in the range from more than −5.0 to less than 10.0 at a temperature of 20° C. and a frequency of 1 kHz, and a component, component F, which consists of compounds having up to six five- or six-membered rings and also has a dielectric anisotropy in the range from more than −5.0 to less than 10.0 at a temperature of 20° C. and a frequency of 1 kHz.

5. A liquid-crystal medium according to claim 1, further comprising one or more compounds of the formula VI

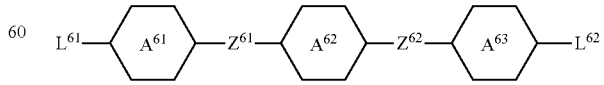
VI in which

L$^{61}$ denotes R$^{61}$ and, in the case where Z$^{61}$ and/or Z$^{62}$ denote trans-CH═CH— or trans-CF═CF—, alternatively also denotes X$^{61}$, $L^{62}$ denotes $R^{62}$ and, in the case where $Z^{61}$ and/or $Z^{62}$ denote trans-CH=CH— or trans-CF=CF—, alternatively also denotes $X^{62}$, $R^{61}$ and $R^{62}$, independently of one another, denote H, unfluorinated alkyl or unfluorinated alkoxy having 1 to 17 C atoms or unfluorinated alkenyl, unfluorinated alkenyloxy or unfluorinated alkoxyalkyl having 2 to 15 C atoms, $X^{61}$ and $X^{62}$, independently of one another, denote F or Cl, —CN, —NCS, —SF$_5$, fluorinated alkyl or alkoxy having 1 to 7 C atoms or fluorinated alkenyl, alkenyloxy or alkoxyalkyl having 2 to 7 C atoms, or —NCS, one of
$Z^{61}$ and $Z^{62}$ denotes trans-CH=CH—, trans-CF=CF— or —C≡C— and the other, independently thereof, denotes trans-CH=CH—, trans-CF=CF— or a single bond, and

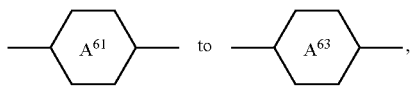

independently of one another, denote

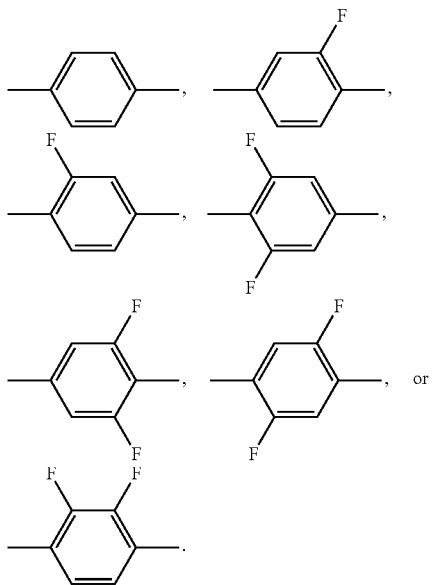

6. A process for the preparation of a liquid-crystal medium according to claim 1, wherein one or more compounds of formula I-M and/or one or more compounds of formula I-U, are mixed with one or more compounds of formula I and/or with one or more additives.

7. A method which comprises including a liquid-crystal medium according to claim 1 in a component for high-frequency technology.

8. A component for high-frequency technology, comprising a liquid-crystal medium according to claim 1.

9. A microwave antenna array, comprising one or more components for high-frequency technology according to claim 8.

10. A process for tuning a microwave antenna array, wherein a component for high-frequency technology according to claim 8 is electrically addressed.

11. A liquid-crystal medium according to claim 1, wherein the compounds of Formula I-M and Formula I-U have $X^1$=CN.

12. A liquid-crystal medium according to claim 1, wherein the compounds of Formula I-M and Formula I-U have $X^1$=CF$_3$.

13. A liquid-crystal medium according to claim 1, comprising compounds of formula I-M.

14. A liquid-crystal medium according to claim 1, comprising compounds of formula I-U.

15. A liquid-crystal medium according to claim 1, wherein

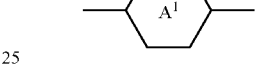

is

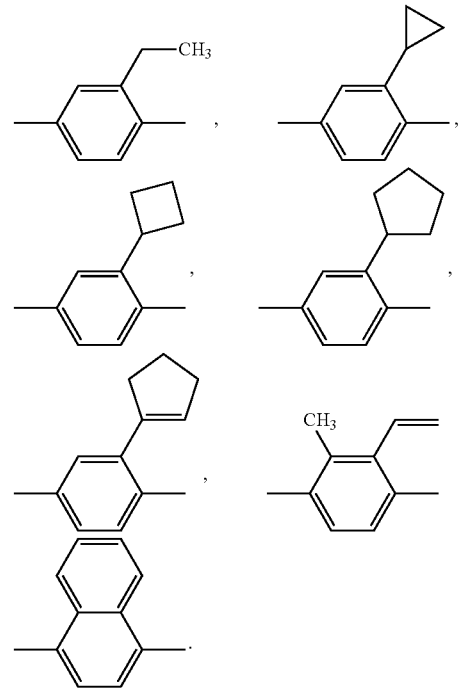

* * * * *